(12) United States Patent
Srivastava et al.

(10) Patent No.: US 7,052,692 B1
(45) Date of Patent: May 30, 2006

(54) ROLE OF TYROSINE PHOSPHORYLATION OF A CELLULAR PROTEIN IN ADENO-ASSOCIATED VIRUS 2-MEDIATED TRANSGENE EXPRESSION

(75) Inventors: Arun Srivastava, Indianapolis, IN (US); Keyun Qing, Indianapolis, IN (US); Xu-Shan Wang, Carmel, IN (US); Selvarangan Ponnazhagan, Birmingham, AL (US); Anil Bajpai, Indianapolis, IN (US)

(73) Assignee: Advanced Research & Technology Institute, Bloomington, IN (US)

( * ) Notice: Subject to any disclaimer, the term of this patent is extended or adjusted under 35 U.S.C. 154(b) by 881 days.

(21) Appl. No.: 09/145,379

(22) Filed: Sep. 1, 1998

Related U.S. Application Data
(60) Provisional application No. 60/056,052, filed on Sep. 2, 1997.

(51) Int. Cl.
*A61K 48/00* (2006.01)
*A61K 39/395* (2006.01)
*C12N 15/864* (2006.01)
*C12N 15/63* (2006.01)
*C07H 21/04* (2006.01)

(52) U.S. Cl. .................. 424/135.1; 424/93.1; 424/93.2; 424/93.6; 424/130.1; 424/134.1; 424/141.1; 424/152.1; 435/5; 435/6; 435/7.1; 435/455; 435/456; 435/457; 435/325; 435/366; 435/320.1; 514/2; 514/44; 536/23.1; 536/23.5

(58) Field of Classification Search .................. 424/93.2, 424/93.6, 93.1, 130.1, 134.1, 135.1, 141.1, 424/152.1; 435/5, 6, 7.1, 455, 456, 457, 325, 435/366, 320.1; 536/23.1, 23.5; 514/2, 44
See application file for complete search history.

(56) References Cited

U.S. PATENT DOCUMENTS

| | | | |
|---|---|---|---|
| 4,933,294 A | 6/1990 | Waterfield et al. | 436/501 |
| 4,943,533 A | 7/1990 | Mendelsohn et al. | 530/388.22 |
| 5,139,941 A | 8/1992 | Muzyczka et al. | 435/456 |
| 5,183,884 A | 2/1993 | Kraus et al. | 536/23.5 |
| 5,378,809 A | 1/1995 | Di Fiore et al. | 530/350 |
| 5,480,968 A | 1/1996 | Kraus et al. | 530/326 |
| 5,487,979 A | 1/1996 | Di Fiore et al. | 435/357 |
| 5,558,864 A | 9/1996 | Bendig et al. | 424/133.1 |
| 5,610,018 A | 3/1997 | Di Fiore et al. | 435/7.1 |
| 5,610,288 A | 3/1997 | Rubenstein | 536/24.5 |
| 5,614,488 A | 3/1997 | Bacha | 514/2 |
| 5,654,307 A | 8/1997 | Bridges et al. | 514/258 |
| 5,674,753 A | 10/1997 | Harvey et al. | 436/501 |
| 5,679,683 A | 10/1997 | Bridges et al. | 514/53 |
| 5,708,156 A | 1/1998 | Ilekis | 536/23.5 |
| 5,717,067 A | 2/1998 | Di Fiore et al. | 530/350 |

OTHER PUBLICATIONS

Ross et al., Human Gene Therapy, vol. 7, pp. 1781–1790, Sep. 10, 1996.*
Kmiec, American Scientist, vol. 87, pp. 240–247, May 1999.*
Verma et al., Nature, vol. 389, pp. 239–242, Sep. 18, 1997.*
W. French Anderson, Nature, vol. 392, pp. 25–20, Apr. 30, 1998.*
Orkin et al., "Report and Recommendations of the Panel to Assess the NIH Investment in Research on Gene Therapy", Dec. 7, 1995.*
R.G. Crystal, Science, vol. 270, pp. 404–410, Oct. 1995.*
J.L. Fox, Nature Biotechnology, vol. 18, pp. 143–144, Feb. 2000.*
Barnes and Peterson, "Biochemical targets of the isoflavone genistein in tumor cell lines", *Soc. Exp. Biol. Med.*, 280:103–108, 1995.
Carter, "Adeno–associated virus vectors", *Curr. Opin. Biotechnol.*, 3:533–539, 1992.
Flotte and Carter, "Adeno–associated virus vectors for gene therapy", *Gene Ther.*, 2:357–362, 1995.
Kearns et al., "Recombinant adeno–associated virus (AAV–CFTR) vectors do not integrate in a site–specific fashion in an immortalized epithelial cell line, " *Gene Ther.*, 3:748–755, 1996.
Ping et al., "Altered β–adrenergic receptor signaling in heart failure, in vivo gene transfer via adeno and adeno–associated virus, " *Microcirculation*, 3:225–228, 1996.
Akiyama et al., "Genistein, a specific inhibitor of tyrosine–specific protein kinases," *J. Biol. Chem.*, 262(12):5592–5595, 1987.
Alexander et al., "Effects of gamma irradiation on the transduction of dividing and nondividing cells in brain and muscle of rats by adeno–associated virus vectors," *Hum. Gene Ther.*, 7:841–850, 1996.
Berns and Bohenzky, "Adeno–Associated Viruses: An Update," *Adv. Virus Res.*, 32:243–307, 1987.
Berns and Giraud, "Adeno–Associated Virus (AAV) Vectors in Gene Therapy: Biology of Adeno–Associated Virus," *Curr. Top. Microbiol. Immunol.*, 218:1–23, 1996.
Bertran et al., "Recombinant Adeno–Associated Virus–Mediated High–Efficiency, Transient Expression of the Murine Cationic Amino Acid Transporter (Ecotropic Retroviral Receptor) Permits Stable Transduction of Human HeLa Cells by Ecotropic Retroviral Vectors," *J. Virol.*, 70 (10) 6759–6766, 1996.

(Continued)

*Primary Examiner*—David Guzo
(74) *Attorney, Agent, or Firm*—Fulbright & Jaworski

(57) ABSTRACT

The present invention identifies a protein, designated the D-sequence-binding protein (D-BP), is phosphorylated at tyrosine residues and blocks AAV-mediated transgene expression in infected cells by inhibiting the leading strand viral DNA synthesis. More particularly, the present invention demonstrates that D-BP is phosphorylated by EGF-R protein tyrosine kinase. Methods of increasing transcription and promoting replication of transgenes exploiting this information are disclosed herein.

35 Claims, 26 Drawing Sheets

OTHER PUBLICATIONS

Boonstra et al., "The Epidermal Growth Factor," *Cell Biol. Intl.*, 19:413–430, 1995.

Carlo–Stella et al., "Effect of the Protein Tyrosine Kinase Inhibitor Genistein on Normal and Leukaemic Haemopoietic Progenitor Cells," *Br. J. Haematol.*, 93:551–557, 1996.

Carter and Flotte, "Adeno–Associated Virus (AAV) Vectors in Gene Therapy: Development of Adeno–Associated Virus Vectors for Gene Therapy of Cystic Fibrosis," *Curr. Top. Microbiol. Immunol.*, 218:119–144, 1996.

Chatterjee and Wong Jr., "Adeno–Associated Virus (AAV) Vectors in Gene Therapy: Adeno–Associated Virus Vectors for Gene Therapy of the Hematopoietic System," *Curr. Top. Microbiol. Immunol.*, 218:61–73, 1996.

Chatterjee et al., "Strategies for efficient gene transfer into hematopoietic cells: The use of adeno–associated virus vectors in gene therapy," *Ann. N.Y. Acad. Sci.*, 770:79–90, 1995.

Constantinou and Huberman, "Genistein as an Inducer of Tumor Cell Differentiation: Possible Mechanisms of Action," *Soc. Exp. Biol. Med.*, 208:109–115, 1995.

Couldwell et al., "Protein Kinase C Inhibitors Induce Apoptosis in Human Malignant Glioma Cell Lines," *FEBS Lett.*, 345:43–46, 1994.

Dudek et al., "Regulation of neruonal survival by the serine–threonine protein kinase Akt," *Science*, 275:661–664, 1996.

Faaland et al., "Rapid Uptake of Tyrphostin into A431 Human Epidermoid Cells Is Followed by Delayed Inhibition of Epidermal Growth Factor (EGF)–Stimulated EGF Receptor Tyrosine Kinase Activity," *Mol. Cell Biol.*, 11(5):2697–2703, 1991.

Fabricant et al., "Nerve Growth Factor Receptors on Human Melanoma Cells in Culture," *Proc. Natl. Acad. Sci. USA*, 74:565–569, 1977.

Ferrari et al., "Second–strand synthesis is a rate–limiting step for efficient transduction by recombination adeno–associated virus vectors," *J. Virol.*, 70(5):3227–3234, 1996.

Fisher et al., "Recombinant Adeno–Associated Virus for Muscle Directed Gene Therapy," *Nat. Med.*, 3:306–312, 1997.

Fisher et al., "Transduction with recombinant adeno–associated virus for gene therapy is limited by leading–strand synthesis," *J. Virol.*, 70:520–532, 1996.

Flotte et al., "Stable in vivo expression of the cystic fibrosis transmembrane conductance regulator with an adeno–associated virus victor," *Proc. Natl. Acad. Sci. USA*, 90:10613–10617, 1993.

Fukazawa et al., "Specific Inhibition of Cytoplasmic Protein Tyrosine Kinases by Herbimycin A In Vitro," *Biochem. Pharmacol.*, 42:1661–1671, 1991.

Gamou et al., "Molecular Evidence for the Lack of Epidermal Growth Factor Receptor Gene Expression in Small Cell Lung Carcinoma Cells," *Cancer Res.*, 47:2668–2673, 1987.

Gazit et al., "Tyrphostins I: Synthesis and Biological Activity of Protein Tyrosine Kinase Inhibitors," *J. Med. Chem.*, 32:2344–2352, 1989.

Ghiringhelli and Romanowski, "Quick Methylene Blue Staining for Visualizing Virus Plaques in Titration Experiments," *Biotechniques*, 17:464–465, 1994.

Giard et al., "In Vitro Cultivation of Human Tumors: Establishment of Cell Lines Derived from a Series of Solid Tumors," *J. Natl. Cancer Inst.*, 51:1417–1423, 1973.

Goodman et al., "Recombinant adeno–associated virus–mediated gene transfer into hematopoietic progenitor cells," *Blood*, 84(5):1492–1500, 1994.

Kaplitt et al., "Long–term gene expression and phenotypic correction using adeno–associated virus vectors in the mammalian brain," *Nat. Genet.*, 8:148–153, 1994.

Kessler et al., "Gene delivery to skeletal muscle results in sustained expression and systemic delivery of a therapeutic protein," *Proc. Natl. Acad. Sci. USA*, 93:14082–14087, 1996.

Koeberl et al., "Persistent Expression of Human Clotting Factor IX from Mouse Liver After Intravenous Injection of Adeno–Associated Virus Vectors," *Proc. Natl. Acad. Sci. USA*, 94:1426–1431, 1997.

Kotin et al., "Prospects for the Use of Adeno–Associated Virus as a Vector for Human Gene Therapy," *Human Gene Therapy*, 5:793–801, 1994.

Kotin et al., "Mapping and direct visualization of a region–specific viral DNA integration site on chromosome 19q13–qter," *Genomics*, 10:831–834, 1991.

Kotin et al., "Site–specific integration by adeno–associated virus," *Proc. Natl. Acad. Sci. USA*, 87:2211–2215, 1990.

Kube and Srivastava, "Quantitative DNA slot blot analysis: inhibition of DNA binding to membranes by magnesium ions," *Nucl. Acids Res.*, 25(16):3375–3376, 1997.

Kube et al., "Encapsidation of adeno–associated virus type 2 rep proteins in wild–type and recombinant progeny virions: rep–mediated growth inhibition of primary human cells," *J. Virol.*, 71(10):7361–7371, 1997.

Kumagai and Dunphy, "Purification and molecular cloning of Plx1, a Cdc25–regulatory kinase from *Xenopus* egg extracts," *Science*, 273:1377–1380, 1996.

Kuo and Yang, "Reversion of v–H–rasTransformed NIH 3T3 Cells by Apigenin Through Inhibiting Mitogen Activated Protein Kinase and its Downstream Oncogenes," *Biochem. Biophys. Res. Comm.*, 212:767–75, 1995.

Levitzki et al., "Inhibition of Portein–Tyrosine Kinases by Tyrphostins," *Meth. Enzymol.*, 201:347–361. 1991.

Levitzki, "Tyrphostins–Potential Antiproliferative Agents and Novel Molecular Tools," *Biochem. Pharmacol.*, 40:913–918, 1990.

Lim and Hauschka, "A Rapid Decrease in Epidermal Growth Factor–Binding Capacity Accompanies the Terminal Differentiation of Mouse Myoblasts In Vitro," *J. Cell. Biol.*, 98:739–747, 1984.

Livneh et al., "Reconstitution of Human Epidermal Growth Factor Receptors and Its Deletion Mutants in Cultured Hamster Cells," *J. Biol. Chem.*, 261:12490–12497, 1986.

Lyall et al., "Tyrphostins Inhibit Epidermal Growth Factor (EGF)–Receptor Tyrosine Kinase Activity in Living Cells and EGF–Stimulated Cell Proliferation," *J. Biol. Chem.*, 264:14503–14509, 1989.

McCown et al., "Differential and Persistent Expression Patterns of CNS Gene Transfer by an Adeno–Associated Virus (AAV) Vector," *Brain Res.*, 713:99–107, 1996.

Miller et al., "Emergence of MCF–7 cells overexpressing a transfected epidermal growth factor receptor (EGFR) under estrogen–depleted conditions: evidence for a role of EGFR in breast cancer growth and progression, " *Cell Growth Diff.*, 5:1263–1274, 1994.

Mizukami et al., "Adeno–associated virus type 2 binds to a 150–kilodalton cell membrane glycoprotein," *Virology*, 217:124–130, 1996.

Muzyczka, "Use of Adeno–Associated Virus as a General Transduction Vector for Mammalian Cells," *Curr. Top. Microbiol. Immunol.*, 158:97–129, 1992.

Nahreini et al., "Versatile adeno–associated virus 2–based vectors for constructing recombinant virions," *Gene*, 124:257–262, 1993.

Novogrodsky et al., "Prevention of Lipopolysaccharide–Induced Lethal Toxicity by Tyrosine Kinase Inhibitors," *Science*, 264:1319–1322, 1994.

Okada et al., "Blockage of Chemotactic Peptide–Induced Stimulation of Neutrophils by Wortmannin as a Result of Selective Inhibition of Phosphatidylinositol 3–Kinase," *J. Biol. Chem.*, 269:3563–3567, 1994.

Ponnazhagan et al., "Adenos–associated virus 2–mediated gene transfer in vivo: organ–tropism and expression of transduced sequences in mice," *Gene*, 190:203–210, 1997.

Ponnazhagan et al., "Adeno–associated virus type 2–mediated transduction in primary human bone marrow–derived $CD34^+$ hematopoietic progenitor cells: donor variation and correlation of transgene expression with cellular differentiation," *J. Virol.*, 71(11):8262–8267, 1997.

Ponnazhagan et al., "Lack of site–specific integration of the recombinant adeno–associated virus 2 genomes in human cells," *Hum. Gene Ther.*, 8:275–284. 1997.

Ponnazhagan et al., "Adeno–associated virus type 2–mediated transduction of murine hematopoietic cells with long––term repopulating ability and sustained expression of a human globin gene in vivo," *J. Virol.*, 71(4):3098–3104, 1997.

Ponnazhagan et al., "Differential expression in human cells from the p6 promoter of human parvovirus B19 following plasmid transfection and recombinant adeno–associated virus 2 (AAV) infection: human megakaryocytic leukaemia cells are non–permissive for AAV infection," *J. Gen. Virol.*, 77:1111–1122, 1996.

Qing et al., "Adeno–associated virus type 2–mediated gene transfer: correlation of tyrosine phosphorylation of the cellular single–stranded D sequence–binding protein with transgene expression in human cells in vitro and murine tissues in vivo," *J. Virol.*, 72(2):1593–1599, 1998.

Qing et al., "Adeno–associated virus type 2–mediated transfer of ecotropic retrovirus receptor cDNA allows ecotropic retroviral transduction of established and primary human cells," *J. Virol.*, 71(7):5663–5667, 1997.

Qing et al., "Role of tyrosine phosphorylation of a cellular protein in adeno–associated virus 2–mediated transgene expression," *Proc. Natl. Acad. Sci. USA*, 94:10879–10884, 1997.

Ross et al., "Gene Therapy in the United States: A Five–Year Status Report," *Human Gene Therapy*, 7:1781–1790, 1996.

Russell et al., "Adeno–associated virus vectors preferentially transduce cells in S phase," *Proc. Natl. Acad. Sci. USA*, 91:8915–8919, 1994.

Russell et al., "DNA synthesis and topoisomerase inhibitors increase transduction by adeno–associated virus vectors," *Proc. Natl. Acad. Sci. USA*, 92:5719–5723, 1995.

Samulski et al., "Helper–free stocks of recombinant adeno–associated viruses: normal integration does not require viral gene expression," *J. Virol.*, 63(9):3822–3828, 1989.

Samulski et al., "Targeted integration of adeno–associated virus (AAV) into human chromosome 19," *EMBO J.*, 10(12):3941–3950, 1991.

Samulski et al., "A recombinant plasmid from which an infectious adeno–associated virus genome can be excised in vitro and its use to study viral replication," *J. Virol.* 61(10):3096–3101, 1987.

Srivastava et al., "Adeno–Associated Virus (AAV) Vectors in Gene Therapy: Adeno–Associated Virus 2–Mediated Transduction and Erythroid Lineage–Specific Expression in Human Hematopoietic Progenitor Cells," *Curr. Top. Microbiol. Immunol.*, 218:93–117, 1996.

Srivastava et al., "KRAS2 Oncogene Overexpression in Myelodysplastic Syndrome with Translocation," *Cancer Genet Cytogenet.*, 35:(1)61–71, 1988.

Srivastava et al., "Nucleotide Sequence and Organization of the Adeno–Associated Virus 2 Genome," *J. Virol.*, 45:555–564, 1983.

Styren et al., "Epidermal Growth Factor Receptor Expression in Demented Elderly: Localization to Vascular Endothelial Cells of the Brain, Pituitary and Skin," *Brain Res.*, 615:181–190, 1993.

Vlahos et al., "A Specific Inhibitor of Phosphatidylinositol 3–Kinase, 2–(4–Morpholinyl)–8–Phenyl–4H–1–Benzopyran–4–One (LY294002)," *J. Biol. Chem.*, 269:5241–5248, 1994.

Walsh et al., "Phenotypic correction of fanconi anemia in human hematopoietic cells with a recombinant adeno–associated virus vector," *J. Clin. Invest.*, 94:1440–1448, 1994.

Wang et al., Characterization of wild–type adeno–associated virus type 2–like particles generated during recombinant viral vector production and strategies for their elimination, *J. Virol.*, 72(7):5472–5480, 1998.

Wang et al., "Adeno–associated virus type 2 DNA replication in vivo: mutation analyses of the D sequence in viral inverted terminal repeats," *J. Virol.*, 71(4)3077–3082, 1997.

Wang et al., "Rescue and replication of adeno–associated virus type 2 as well as vector DNA sequences from recombinant plasmids containing deletions in the viral inverted terminal repeats: selective encapsidation of viral genomes in progeny virions," *J. Virol.*, 70(3):1668–1677, 1996.

Wang et al., "Rescue and replication signals of the adeno–associated virus 2 genome," *J. Mol. Biol.*, 250:573–580, 1995.

Xiao et al., "Efficient long–term gene transfer into muscle tissue of immunocompetent mice by adeno–associated virus vector," *J. Virol.*, 70(11):8098–8108, 1996.

Yaish et al., "Blocking of EGF–Dependent Cell Proliferation by EGF Receptor Kinase Inhibitors," *Science*, 242:933–935, 1988.

Yang et al., "Characterization of Cell Lines That Inducibly Express the Adeno–Associated Virus Rep Proteins," *J. Virol.*, 68(8):4847–4856, 1994.

Zhou et al., "Adeno–associated virus 2–mediated transduction and erythroid cell–specific expression of a human β–globin gene," *Gene Ther.*, 3:223–229, 1996.

* cited by examiner

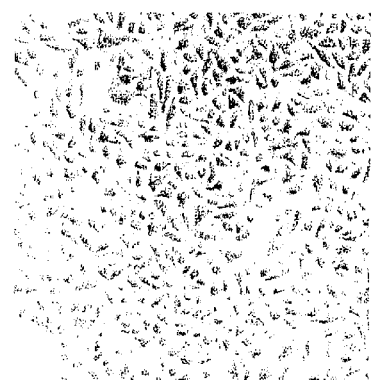
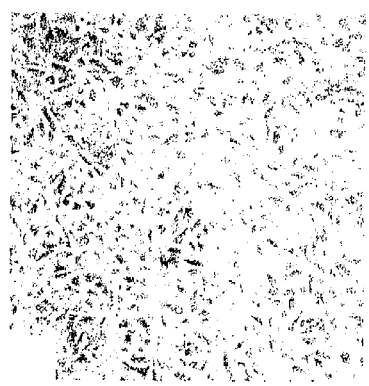
FIG.17A    FIG.17B
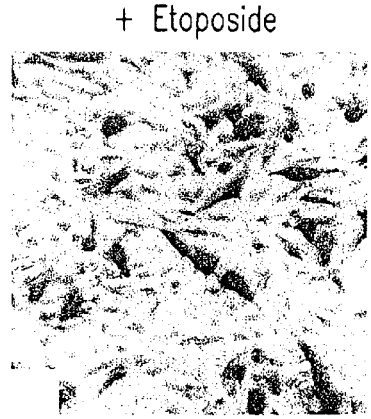
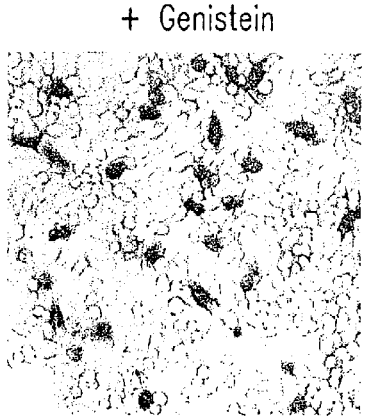
FIG.17C    FIG.17D
FIG.17E    FIG.17F

SEQUENCE LISTING

```
<160> NUMBER OF SEQ ID NOS: 5

<210> SEQ ID NO 1
<211> LENGTH: 20
<212> TYPE: DNA
<213> ORGANISM: adeno-associated virus 2

<400> SEQUENCE: 1
aggaacccct agtgatggag                                                 20

<210> SEQ ID NO 2
<211> LENGTH: 20
<212> TYPE: DNA
<213> ORGANISM: adeno-associated virus 2

<400> SEQUENCE: 2
ctccatcact agggttcct                                                  20

<210> SEQ ID NO 3
<211> LENGTH: 21
<212> TYPE: DNA
```

```
<213> ORGANISM: adeno-associated virus 2

<400> SEQUENCE: 3
ccaatattag atctgatatc a                                      21

<210> SEQ ID NO 4
<211> LENGTH: 21
<212> TYPE: DNA
<213> ORGANISM: adeno-associated virus 2

<400> SEQUENCE: 4
accgtggata ctaatggcgt g                                      21

<210> SEQ ID NO 5
<211> LENGTH: 30
<212> TYPE: PRT
<213> ORGANISM: Homo sapiens

<400> SEQUENCE: 5

Asp Asn Asn Arg Glu Leu Asp Leu Glu Ile Asn Arg Ala Asp Val Leu
 1               5                  10                  15

Ala Gln Tyr Glu Asp Ile Ala Gln Ser Gly Lys Ala Glu Ala
            20                  25                  30
```

ROLE OF TYROSINE PHOSPHORYLATION OF A CELLULAR PROTEIN IN ADENO-ASSOCIATED VIRUS 2-MEDIATED TRANSGENE EXPRESSION

The present application is a continuation-in-part of co-pending U.S. Provisional Patent Application Ser. No. 60/056,052 filed Sep. 2, 1997. The entire text of the above-referenced disclosure is specifically incorporated by reference herein without disclaimer. The government may own rights in the present invention pursuant to grant numbers HL-48342, HL-53586, HL-58881, and DK-49218 from the National Institutes of Health.

BACKGROUND OF THE INVENTION

1. Field of the Invention

The present invention relates generally to the fields of gene therapy. More particularly, it concerns gene transfer using adeno-associated virus and methods of increasing transcription and promoting replication of transgenes.

2. Description of Related Art

Gene therapy protocols involving recombinant viral vectors are gaining wide attention and have immense potential to become the future mode of molecular medicine. Of the different viral vectors attempted to mediate gene transfer, the retrovirus and adenovirus-based vector systems have been extensively investigated over a decade. Recently, adeno-associated virus (AAV) has emerged as a potential alternative to the more commonly used retroviral and adenoviral vectors (Muzyczka, 1992; Carter, 1992; Flotte and Carter, 1995; Chatterjee et al., 1995; Chatterjee and Wong, 1996). While studies with retroviral and adenoviral mediated gene transfer raise concerns over potential oncogenic properties of the former, and immunogenic problems associated with the latter, AAV has not been associated with any such pathological indications (Berns and Bohenzky, 1987; Berns and Giraud, 1996).

In addition, AAV possesses several unique features that make it more desirable than the other vectors. Unlike retroviruses, AAV can infect non-dividing cells; wild-type AAV has been characterized by integration, in a site-specific manner, into chromosome 19 of human cells (Kotin et al., 1990; Kotin et al., 1991; Samulski et al., 1991), and AAV also possesses anti-oncogenic properties (Berns and Giraud, 1996). Recombinant AAV genomes are constructed by molecularly cloning DNA sequences of interest between the AAV ITRs, eliminating the entire coding sequences of the wild-type AAV genome. The AAV vectors thus produced lack any of the coding sequences of wild-type AAV, yet retain the property of stable chromosomal integration and expression of the recombinant genes upon transduction both in vitro and in vivo (Bertran et al., 1996; Kearns et al., 1996; Ponnazhagan et al., 1997a).

Recent studies have suggested that following infection, the leading strand viral DNA synthesis is a rate-limiting step in the efficient transduction by AAV vectors (Fisher et al., 1996; Ferrari et al., 1996). AAV inverted terminal repeats (ITRs) contain 145 nucleotides (nts) each, the terminal 125 nts of which are palindromic and form T-shaped hairpin (HP) structures, and the 3'-HP structure serves as a primer for AAV DNA replication.

The single-stranded nature of the AAV genome significantly impacts upon the transduction efficiency since the second-strand viral DNA synthesis is the rate-limiting step. It is important to elucidate a factor that is capable of circumventing this step so that AAV vectors may be more effectively used Once such a factor is elucidated, it will be possible to increase the transcription and replication from an adeno-associated viral (AAV) vector.

SUMMARY OF THE INVENTION

The present invention for the first time identifies a protein, designated the D-sequence-binding protein (D-BP), which is phosphorylated at tyrosine residues and blocks AAV-mediated transgene expression in infected cells by inhibiting the leading strand viral DNA synthesis. The protein has a molecular weight of 53 kDa.

Thus, in a preferred embodiment, the present invention provides an isolated and purified D sequence binding protein (D-BP) having a molecular weight of about 53 kDa. In more particular embodiments, the present invention may provide a peptide derived from the D-BP binding protein described above. The peptide may be about 10 to about 50 contiguous amino acids of the D-BP described herein. In other embodiments, the peptide may be about 10, 15, 20, 25, 50 or more amino acids of the D-BP described herein.

In other aspects, the present invention provides an isolated and purified nucleic acid encoding a D sequence binding protein (D-BP) having a molecular weight of 53 kDa. In particular embodiments the present invention provides an oligonucleotide of about 15 to about 50 contiguous base pairs of the nucleic acid encoding D-BP, or the complement thereof. The oligonucleotide may be, independently, about 15 base pairs in length, about 20 base pairs in length, about 25 base pairs in length, about 30 base pairs in length, about 50 base pairs in length.

In another aspect, the present invention provides a method for increasing the transcription of a selected nucleic acid from an adeno-associated viral (AAV) vector in a host cell comprising the steps of providing an AAV vector comprising an expression cassette comprising said selected nucleic acid and a promoter active in eukaryotic cells, wherein said selected nucleic acid is operably linked to said promoter; contacting said vector with said host cell under conditions permitting uptake of said vector by said host cell; and inhibiting the function of D sequence binding protein (D-BP) in said host cell, whereby the transcription of said selected nucleic acid is increased relative to the transcription of said selected nucleic acid in a cell where D-BP is not inhibited.

In particular embodiments, the inhibiting may comprise reducing the expression of D-BP in said host cell. In more particular embodiments, reducing the expression of D-BP is achieved by contacting the host cell with an antisense D-BP nucleic acid. In certain embodiments, the antisense D-BP nucleic acid targets a translational start site. In other embodiments, the antisense D-BP nucleic acid targets a splice-junction site. In specific embodiments, the inhibiting comprises reducing the D sequence binding activity of said D-BP in the host cell.

In still other embodiments, reducing the binding activity is achieved by inhibiting the tyrosine phosphorylation of D-BP. More specifically, it is contemplated that inhibiting the phosphorylation may be achieved by contacting said host cell with a D-BP derived peptide containing a tyrosine residue. By "D-BP derived peptide containing a tyrosine residue" it is intended that the D-BP peptide is a mimetic of D-BP that becomes preferentially phosphorylated compared to the wild-type D-BP. In especially preferred embodiments, inhibiting the phosphorylation may be achieved by contacting said host cell with an agent that inhibits tyrosine kinase.

In particular embodiments of the present invention, the tyrosine kinase is an EGF-R tyrosine kinase. In further preferred embodiments, the agent is an inhibitor of EGF-R that reduces the expression of EGF-R protein kinase. More particular embodiments contemplate that the inhibitor of EGF-R protein kinase is an agent that binds to and inactivates EGF-R protein kinase. In alternative preferred embodiments, the inhibitor of EGF-R protein kinase inhibits the interaction of EGF-R with a D-BP. Those embodiments where the agent reduces the expression of EGF-R protein kinase, include those in which the agent is an antisense construct. In those embodiments in which the agent binds to and inactivates EGF-R protein kinase, the agent may be an antibody or a small molecule inhibitor. In specific embodiments, the antibody is a single chain antibody or a monoclonal antibody. In more defined embodiments, the agent that inhibits phosphorylation may be selected from the group consisting of hydroxyurea, genistein, tyrphostin 1, tyrphostin 23, tyrphostin 63, tyrphostin 25, tyrphostin 46, and tyrphostin 47. In other aspects, inhibiting the phosphorylation is achieved by contacting said host cell with a nucleic acid encoding a phosphatase. In other aspects, the inhibition is achieved by contacting said cell with AdE4orf6.

In particular embodiments, reducing the binding activity of D-BP is achieved by contacting the cell with an oligonucleotide that mimics AAV D-sequences. In other embodiments, the host cell may be in a mammal. The mammal may be a human. In other aspects, the host cell may be a tumor cell.

In other aspects, there is provided a monoclonal antibody that binds immunologically to D-BP. In other embodiments, the present invention also provides a polyclonal antisera that binds immunologically to D-BP.

Also contemplated by the present invention is a method for promoting the replication of an adeno-associated viral (AAV) vector in a host cell comprising the steps of providing an AAV vector; contacting said vector with said host cell under conditions permitting uptake of said vector by said host cell; and inhibiting the function of D sequence binding protein (D-BP) in said host cell, whereby the replication of said vector is promoted relative to the replication of said vector in a cell where D-BP is not inhibited. In preferred aspects, the AAV vector may comprise an expression cassette comprising said selected nucleic acid and a promoter active in eukaryotic cells, wherein said selected nucleic acid is operably linked to said promoter. In more particular embodiments, the method may further comprise inhibiting EGF-R protein kinase activity, expression or function.

Yet another aspect of the present invention contemplates a method for increasing the expression of a selected nucleic acid from an adeno-associated viral (AAV) vector in a host cell comprising the steps of providing an AAV vector; contacting the vector with the host cell under conditions permitting uptake of the vector by the host cell; and inhibiting the function of D sequence binding protein (D-BP) in the host cell, whereby the expression of the selected nucleic acid is increased relative to the expression of the selected nucleic acid in a cell where D-BP is not inhibited. More particularly, the AAV vector comprises an expression cassette comprising the selected nucleic acid and a promoter active in eukaryotic cells, wherein the selected nucleic acid is operably linked to the promoter. In other embodiments, the method further comprises inhibiting EGF-R protein kinase activity, expression or function.

In another aspect, the present invention provides a method for treating a disease in a subject comprising the steps of providing an adeno-associated virus (AAV) vector comprising an expression cassette comprising a therapeutic nucleic acid and a promoter active in eukaryotic cells, wherein said therapeutic nucleic acid is operably linked to said promoter; contacting said vector with said host cell under conditions permitting uptake of said vector by said host cell; and inhibiting the function of D sequence binding protein (D-BP) in said host cell, whereby the therapeutic nucleic acid is transcribed in said cell and effects a treatment of said disease. In particular embodiments, the disease is cancer. In other embodiments, the therapeutic nucleic acid encodes a polypeptide. In still other embodiments, the therapeutic nucleic acid encodes an antisense mRNA. The method further may comprise inhibiting EGF-R protein kinase activity, expression or function.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A: WCE prepared from the indicated cell types were used in EMSA with the D(−) probe (lanes 1–4), and the D(±) probe (lanes 5–8) as described in Example 1. FIG. 1B: HeLa cells were treated with either 1 mM NaOV (lanes 1,3), or with 150 μM genistein (lanes 2,4), and equivalent amounts of WCE prepared from these cells were used in EMSA with the D(−) probe (lanes 1,2), and the D(±) probe (lanes 3,4) as described above.

FIG. 17A–FIG. 17G. Effect of tyrosine kinase inhibitors on HeLa cells. FIG. 17A mock infected cells. FIG. 17B HeLa cells infected with vCMVp-LacZ. FIG. 17C HeLa cells infected with vCMVp-LacZ and treated with etoposide. FIG. 17D HeLa cells infected with vCMVp-LacZ and treated with genistein. FIG. 17E HeLa cells infected with vCMVp-LacZ and treated with tyrophostin 1. FIG. 17F HeLa cells infected with vCMVp-LacZ and treated with tyrophostin 23. FIG. 17G Effect of various tyrphostin compositions on HeLa cells infected with vCMVp-LacZ.

DESCRIPTION OF ILLUSTRATIVE EMBODIMENTS

Figure 1A:
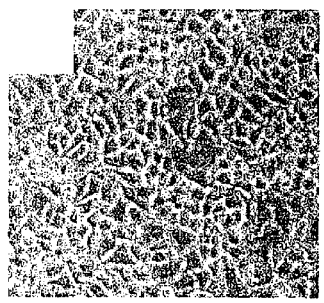
FIG. 1A, FIG. 1B and FIG. 1C. Comparative analyses of transduction efficiency of vCMVp-lacZ in established human cell lines. Approximately equivalent numbers of HeLa (FIG. 1A), KB (FIG. 1B), and 293 (FIG. IC) cells were infected with 4 multiplicity of infection (moi) of vCMVp-lacZ under identical conditions. Forty eight h post-infection, cells were fixed, stained with X-gal; and the number of blue cells were enumerated as described in Example 1. Magnification ×100.

Viral vectors are widely utilized for a variety of gene transfer endeavors. For example, retroviral vectors have been used for a number of years to transform cell lines in vitro for the purpose of expressing exogenous polypeptides. More recently, with advancements in genetic therapies, various other vectors including adenoviruses and herpesviruses, along with retroviruses, and more recently adeno-associated viruses, have been utilized to transfer therapeutic genes into the cells of patients.

While retroviral vectors and adenoviral vectors have been associated with a wide variety of pathological indications, adeno-associated viral (AAV) vectors are considered especially desirable for a number of reasons. In the first instance, AAVs they are not associated with any known pathological indications. Further, AAV can infect non-dividing cells (Kotin et al., 1990; Kotin et al., 1991; Samulski et al., 1991) and also possesses anti-oncogenic properties (Berns and Giraud, 1996). AAV vectors can be produced that lack any of the coding sequences of wild-type AAV, yet retain the property of stable chromosomal integration and expression of the recombinant genes upon transduction both in vitro and in vivo (Bertran et al., 1996; Kearns et al., 1996; Ponnazhagan et al., 1997a).

Although an attractive alternative to other viral vectors, the use AAV as a delivery vector has been limited. Because AAV is a single-stranded DNA-containing virus, a major limitation in AAV-mediated high-efficiency transduction has been the conversion of the single-stranded viral genome to a transcriptionally-active double-stranded intermediate (Ferrari et al., 1996; Fisher et al., 1996). Although a variety of biological, chemical and physical agents, (co-infection of target cells with adenovirus (Ad), or expression of the AdE4orf6 protein (Ferrari et al., 1996; Fisher et al., 1996), treatment with hydroxyurea (HU), or etoposide (Russell et al., 1995), or UV- or X-ray irradiation (Alexander et al., 1996; Ferrari et al., 1996)), can greatly enhance the efficiency of AAV-mediated transduction, presumably by catalyzing the genomic conversion, the precise mechanism(s) by which these agents mediate to facilitate the viral second-strand DNA synthesis still remains unknown.

The present invention, for the first time, provides a clear indication to how second strand replication of AAV is inhibited. Further, the present invention outlines methods of increasing AAV-mediated gene expression and improving the efficacy of virally-mediated gene therapy.

A. The Present Invention (i) D-Sequence Binding Protein

The present inventors have identified a host cellular protein that binds to the D-sequence of adeno-associated viral genome and termed it D-sequence binding protein (D-BP). Furthermore, the inventors have shown that dephosphorylation of the cellular D-BP correlates strongly with AAV transduction efficiency. Dephosphorylation of the D-BP facilitates second-strand synthesis of the AAV genome delivered to target cells as a single-stranded DNA molecule, suggesting that manipulation of phosphorylation state of this protein may be exploitable as one of the strategies for significantly improving transduction efficiency of recombinant AAV vectors. A strong correlation between phosphorylation state of the D-BP and the extent of efficient transduction by AAV in murine organs/tissues in vivo has also been demonstrated, showing this approach of improving transduction efficiency will work, as well as indicating that the D-BP may be evolutionarily conserved.

The mechanism by which dephosphorylation of the D-BP facilitates second-strand viral DNA synthesis remains unclear. One of the possibilities that the D-BP itself may possess a DNA polymerase-like activity currently is being tested. Alternatively, dephosphorylation of the D-BP might activate cellular DNA polymerase(s) necessary for host cell DNA synthesis or DNA-repair pathway, by which the second-strand viral DNA synthesis is accomplished. The inventors' studies with highly purified preparations of the D-BP indicate that this protein undergoes autophosphorylation followed by auto-dephosphorylation, the significance of which is not clear. However, the purified D-BP has been determined to be an approximately 53 kDa protein, but distinct from the p53 tumor suppressor protein, since monoclonal anti-p53 antibody failed to immunoprecipitate the D-BP.

Since the present invention shows that high efficiency of recombinant AAV transduction in a variety of organs is most likely due to the presence of dephosphorylated form of the D-BP, such an approach will also be useful in determining the transduction potential of untested tissues/organs, especially of human origin, by AAV vectors. For example, based on the data shown in Table 4, it would appear that kidney might be an additional organ of choice for AAV-mediated transduction since the ratio of dephosphorylated/phosphorylated D-BPs in these tissues is approximately 1.4, a level consistent with that seen in 293 cells, a cell line derived from human embryonic kidney.

In another aspect, the search for additional specific compounds that mediate dephosphorylation of the D-BP is facilitated by the present invention. The elucidation of such compounds will serve to augment transduction efficiency of recombinant AAV vectors in a wide variety of tissue and organs, including primary hematopoietic stem/progenitor cells, potentially leading to their successful use in gene therapy of specific hematological disorders such as sickle-cell anemia and β-thalassemia (Goodman et al., 1994; Ponnazhagan et al., 1997d; Walsh et al., 1994; Zhou et al., 1996). Examples of mediators of phosphorylation known to those of skill in the art include genistein, tyrphostin A48, tyrphostin 1, tyrphostin 23, tyrphostin 25, tyrphostin 46, tyrphostin 47, tyrphostin 51, tyrphostin 63, tyrphostin AG1478, herbmycin A, LY 294002, wortmannin, staurosporine, tyrphostin AG126, tyrphostin AG1288, tyrphostin 1295, and tyrphostin 1296. As can be seen in FIG. 17A–FIG. 17G, the tyrphostins group of inhibitors are particularly useful in conjunction with the present invention.

The identification of the D-BP, and the availability of the cellular gene that encodes it, will provide an insight into its role in the host cell, and also in the AAV life cycle in general, and AAV-mediated gene transfer in particular. Thus, the elucidation of these relationships will, hopefully, improve the odds of successful use of AAV vectors in human clinical trials.

(ii) Involvement of EGF-R PTK in the Phosphorylation of D-BP

In the present invention, it is documented that treatment of cells with specific inhibitors of the epidermal growth factor receptor protein tyrosine kinase (EGF-R PTK) activity, such as tyrphostin, leads to significant augmentation of AAV transduction efficiency, and phosphorylation of the ssD-BP is mediated by the EGF-R PTK. Treatment of cells with epidermal growth factor (EGF) results in phosphorylation of the ssD-BP, whereas treatment with tyrphostin causes dephosphorylation of the ssD-BP, and consequently, leads to increased expression of the transgene. Furthermore, AAV transduction efficiency inversely correlates with expression of the EGF-R in different cell types, and stable transfection of the EGF-R cDNA causes phosphorylation of the ssD-BP leading to significant inhibition in AAV-mediated transgene expression which can be overcome by the tyrphostin treatment. These data show that the PTK activity of the EGF-R is a crucial determinant in the life cycle of AAV, and that further studies on the interaction between the EGF-R and the ssD-BP may yield new insights not only into its role in the host cell but also in the successful use of AAV vectors in human gene therapy. Methods and compositions for achieving efficient AAV transduction are provided in detail herein below.

B. Adeno-associated Virus and it Use in Gene Therapy (i) Adeno-associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The sequence of AAV is provided in (Srivastava et al., 1983).

The AAV-ITRs also contain an additional domain, designated the D-sequence, a stretch of 20 nts that is not involved in the HP formation (Bems and Bohenzky, 1987; Berns and Giraud, 1996; Srivastava et al., 1983), the inventors hypothesize that one or more cellular protein(s) interact with the D-sequence and prevent the second strand viral DNA synthesis. Thus the identification of such a host protein merits study. Once elucidated it will be possible to increase the transcription and replication from an adeno-associated viral (AAV) vector. Other uses for such a protein will become apparent in the following disclosure.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector of the present invention can be obtained by restriction endonuclease digestion of AAV or a plasmid such as psub201, which contains a modified AAV genome (Samulski et al., 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e. stable and site-specific integration. The ordinarily skilled artisan also can determine which minor modifications of the sequence can be tolerated while maintaining the ability of the terminal repeats to direct stable, site-specific integration.

(ii) Adeno-associated Viral Mediated Gene Therapy

AAV-based vectors have proven to be safe and effective vehicle for gene delivery in vitro, and these vectors are now being developed and tested in pre-clinical and clinical stages for a wide range of applications in potential gene therapy, both ex vivo and in vivo. However, the inventors (Ponnazhagan et al., 1997b; 1997c; 1997d; 1997d) and others (Carter and Flotte, 1996; Chatterjee et al., 1995; Ferrari et al., 1996; Fisher et al., 1996; Flotte et al., 1993; Goodman et al., 1994; Kaplitt et al., 1994; 1996, Kessler et al., 1996; Koeberl et al., 1997; Mizukami et al., 1996; Xiao et al., 1996) have repeatedly observed wide variations in AAV transduction efficiency in different cells and tissues in vitro as well as in vivo.

It would seem reasonable to suggest that AAV transduction efficiency correlates with the number of the putative cell surface receptors, although the identity of this receptor still remains elusive (Mizukami et al., 1996). However, it has become clear from the inventors' present studies that such a correlation most probably does not exist since 293 cells that express relatively the least numbers of these putative receptors are transduced most efficiently, an observation consistent with previously published reports (Ferrari et al., 1996; Fisher et al., 1996).

AAV-mediated efficient gene transfer and expression in the lung has already led to clinical trials for the treatment of cystic fibrosis (Carter and Flotte, 1996; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996). Since the present invention shows that high efficiency of recombinant AAV transduction in these organs or tissues is most likely due to the presence of dephosphorylated form of the D-BP, such an approach will also be useful in determining the transduction potential of untested tissues/organs, especially of human origin, by AAV vectors.

C. EGF-Receptor Tyrosine Kinase

This present invention shows that the D-BP is phosphorylated by EGFR PTK thereby suggesting that EGFR PTK plays a crucial role in the transduction efficiency of AAV. The epidermal growth factor receptor tyrosine kinase family (EGFR) is a family of cell surface receptors that consists of the EGF receptor (also known as Erb-B1), the Erb-B2 receptor, and its constitutively active oncoprotein mutant Neu, the Erb-B3 receptor and the Erb-B4 receptor.

The EGFR has as its two most important ligands Epidermal Growth Factor (EGF) and Transforming Growth Factor alpha (TGFα). The receptors appear to have only minor functions in adult humans, but are apparently implicated in the disease process of a large portion of all cancers, especially colon and breast cancer. The closely related Erb-B2, Erb-B3 and Erb-B4 receptors have a family of Heregulins as their major ligands, and receptor overexpression and mutation have been unequivocally demonstrated as the major risk factor in poor prognosis breast cancer. The skilled artisan is referred to U.S. Pat. No. 5,378,809; U.S. Pat. No. 5,717,067; U.S. Pat. No. 5,708,156; U.S. Pat. No. 5,674,753; U.S. Pat. No. 5,654,307; U.S. Pat. No. 5,614,488; U.S. Pat. No. 5,610,288; U.S. Pat. No. 5,610,018; U.S. Pat. No. 5,558,864; U.S. Pat. No. 5,487,979; U.S. Pat. No. 5,480,968; U.S. Pat. No. 5,183,884; U.S. Pat. No. 4,933,294; U.S. Pat. No. 5,679,683 and U.S. Pat. No. 4,943,533, (each specifically incorporated herein by reference) for specific disclosure of the nature of EGFR and related tyrosine kinases as well as agents that may affect the function of EGFR.

Figure 25:
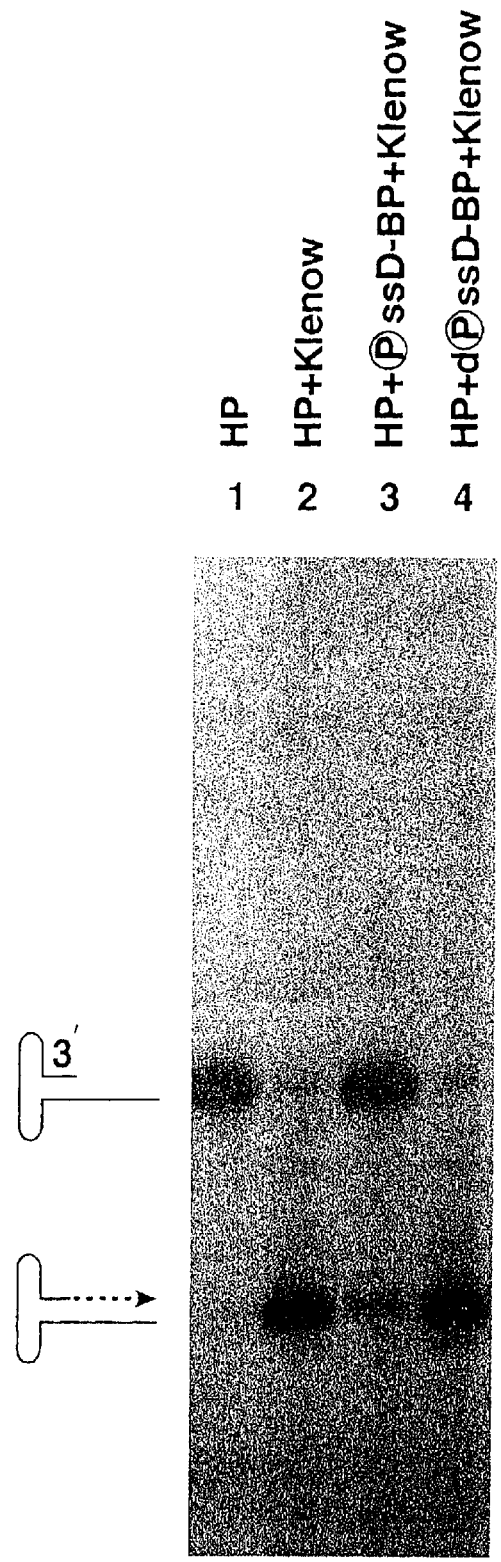
FIG. 25. Effects of phosphorylated and dephosphorylated forms of the ssD-BP on AAV second-strand DNA synthesis in in vitro replication assays. The $^{32}$P-labeled single-stranded AAV DNA with the 3′ hairpin primer (lane 1) was used as a substrate for DNA synthesis with the Klenow fragment of *E. coli* DNA polymerase I and unlabeled dNTPs (lane 2) as well as in the presence of either the phosphorylated ssD-BP (lane 3), or in the presence of the dephosphorylated ssD-BP (lane 4) under identical conditions. DNA samples were fractionated on a 6% polyacrylamide gel and autoradiographed as described in Example 1.

In the present invention, a systematic search for the protein tyrosine kinase responsible for catalyzing the phosphorylation of the ssD-BP led to the identification of the EGF-R PTK since treatment of cells with tyrphostin, the specific inhibitors of the PTK activity of the EGF-R, resulted in a dramatic increase in AAV-mediated transgene expression. In particular, treatment with tyrphostin1 consistently resulted in the greatest increase in AAV transduction efficiency. In accordance with the present invention, (Qing et al., 1997b), the phosphorylated form of the ssD-BP blocks the viral second-strand DNA synthesis since treatment with tyrphostin prevents phosphorylation of the ssD-BP. In fact, this model was experimentally tested in in vitro DNA replication assays in which the effects of both phosphorylated and dephosphorylated forms of affinity column-purified ssD-BPs was examined (FIG. 25). It is remarkable that, consistent with the model of the present invention, the AAV second-strand DNA synthesis is indeed inhibited by the phosphorylated ssD-BP, whereas the dephosphorylated ssD-BP has no significant effect under identical conditions.

The possibility that tyrphostin-treatment augments the promoter activity which leads to increased transgene expression was ruled out by studies in which a double-stranded plasmid DNA containing the same CMV promoter-driven lacZ reporter gene was transfected in tyrphostin-treated cells, and no effect on the extent of transgene expression was observed. Although the precise reason for lack of effect of tyrphostin 51, known to be specific for the EGF-R PTK, on AAV transduction efficiency in HeLa cells remains unclear, this treatment was insufficient to cause dephosphorylation of the ssD-BP. It is possible that each tyrphostin inhibits the EGF-R PTK by different mechanisms. It also is possible that tyrphostin 1 and tyrphostin 23, the two most active compounds, act on downstream target(s) of the EGF-R PTK as well. Interestingly, however, there was a significant increase in the ratio of dephosphorylated to phosphorylated forms of the ssD-BP when the cells were treated with tyrphostin1 and tyrphostin 23. The increase in this ratio, once again, strongly correlated with the efficiency of AAV-mediated transduction. Tyrphostin 51, on the other hand, failed to elicit a significant response. However, since other treatments such as HU, or expression of AdE4orf6 protein, which have been shown to increase AAV transduction efficiency, also result in an increase in the ratio of dephosphorylated to phosphorylated ssD-BP, it is possible that these treatments also involve the inhibition of the EGF-R PTK.

Figure 22A:
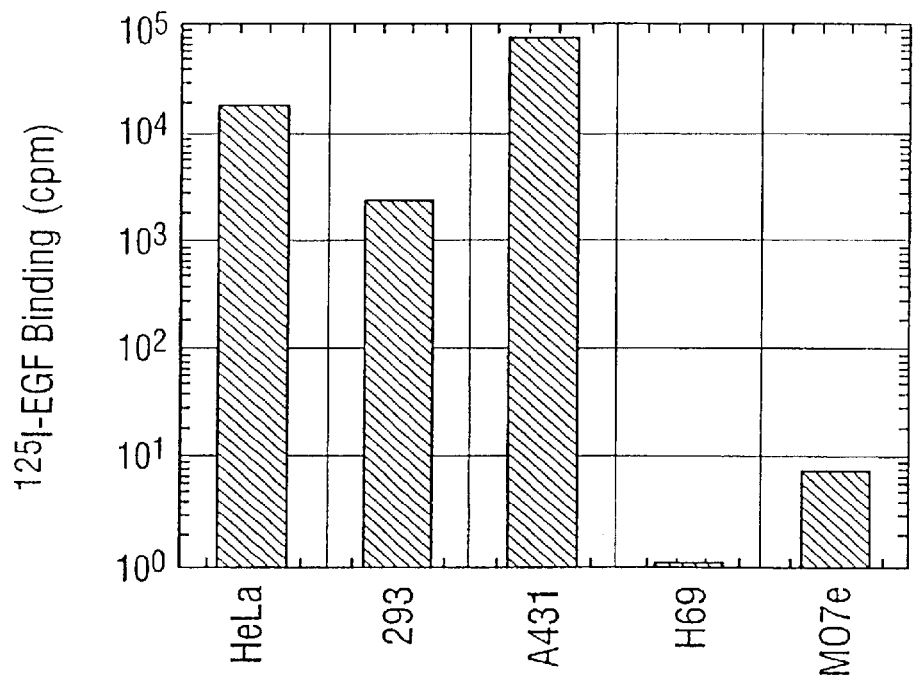
FIG. 22A and FIG. 22B. Analysis of binding of EGF and AAV to different cell types. Equivalent numbers of HeLa, 293, A431, and M07e cells were analyzed in binding assays using either $^{125}$I-EGF (FIG. 22A), or $^{35}$S-AAV (FIG. 22B) as described in Example 1.
Figure 22B:
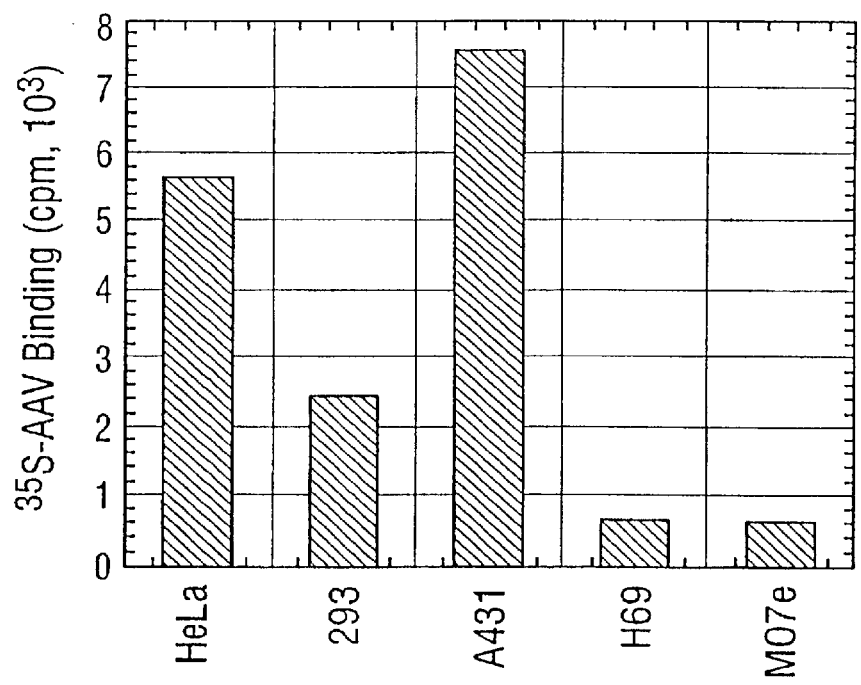
Figure 23:
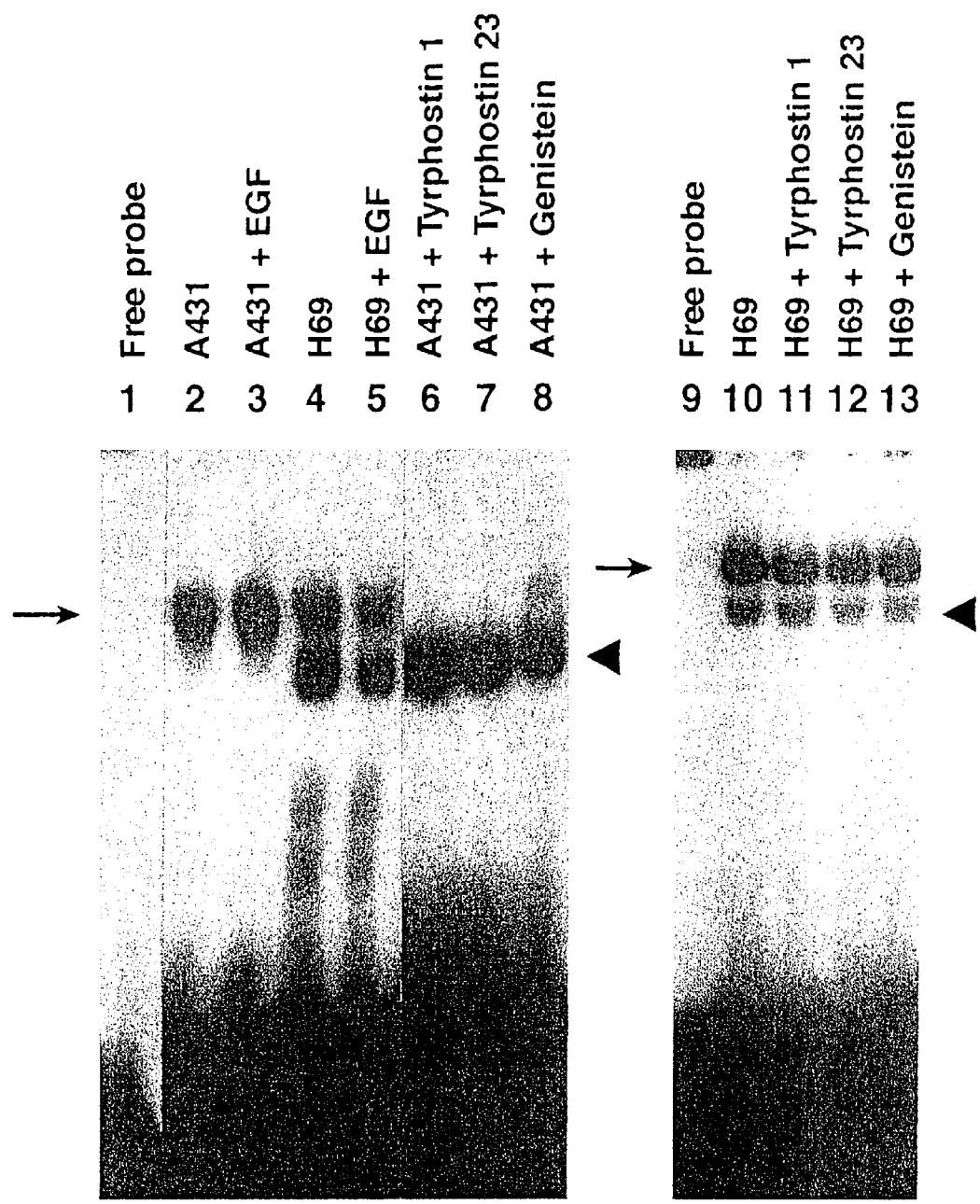
FIG. 23. EMSA with WCE prepared from A431 and H69 cells following treatment with EGF, tyrphostin 1, tyrphostin 23, or genistein. Equivalent amounts of WCEs prepared from mock-treated A431 and H69 cells (lanes 2 and 4), or treated with EGF (lane 3 and 5), and A431 cells (lanes 6–8) and H69 cells (lanes 9–11) treated with tyrphostin 1, tyrphostin 23, and genistein, respectively, were used in EMSA with the D(−) probe as described in Example 1. The phosphorylated and dephosphorylated forms of the ssD-BP are indicated by the arrow and the arrowhead, respectively.

An additional observation was that there appeared to be a strong correlation between the cellular EGF-R numbers and the extent of AAV-binding. For example, A431 cells, which express the highest numbers of the EGF-R, also bound AAV most efficiently, and H69 cells, which do not express these receptors, failed to bind AAV (FIG. 22). It may be that in addition to heparan sulfate proteoglycan for binding, AAV may utilize the EGF-R as a co-receptor for efficient entry. It also is noteworthy that phosphorylated forms of the ssD-BP were detected in H69 cells that apparently lack the EGF-R PTK activity (FIG. 23). Moreover, the pattern of phosphorylation of the ssD-BP in H69 cells was not altered in response to treatment with genistein, tyrphostin 1, and tyrphostin 23. In addition to the phosphorylation by EGF-R PTK, it may be that the ssD-BP is phosphorylated by other protein tyrosine kinases and/or serine/threonine kinases in these cells.

EGF-R PTK can be activated upon EGF ligand binding (Boonstra et al., 1995). Treatment of 293 cells with EGF resulted in an increase in the amount of the phosphorylated form of the ssD-BP, again suggesting the involvement of the EGF-R PTK in the ssD-BP phosphorylation. However, treatment of 293 cells with EGF also resulted in increased transduction with vCMVp-lacZ, an apparent paradox. It is possible that this may be due to EGF pushing cells toward the S-phase of cell cycle (Faaland et al., 1991) since it has been previously reported that AAV vectors transduce cells in S-phase greater than 200 times the frequency than cells that are quiescent (Russell et al., 1994). However, the inventors believe that the rate of dephosphorylation of the ssD-BP in 293 cells may be high enough to negate the transient effect of EGF since WCEs were prepared and analyzed immediately following the EGF-treatment, whereas AAV-mediated transgene expression was evaluated 48 h p.i. Alternatively, it is possible that other factors, in addition to the ssD-BP phosphorylation state, act in concert to influence the AAV transduction efficiency. It is noteworthy, however, that skeletal muscle and brain tissues, which have been shown to be extremely well-transduced by recombinant AAV vectors in vivo (Fisher et al., 1997; Kaplitt et al., 1994; Kessler et al., 1996; McCown et al., 1996; Xiao et al., 1996), express little to no EGF-R (Lim and Hauschka, 1984; Styren et al., 1993).

The toxicity assays demonstrated that both tyrphostin 1 and tyrphostin 23 were much less toxic to cells than other previously published treatments such as genistein or HU. The low toxicity of these compounds as well as their ability to significantly increase recombinant AAV transduction efficiency may prove to be valuable for gene therapy. The inventors have shown that treatment of primary human bone marrow-derived CD34 hematopoietic progenitor cells with tyrphostin 1 and tyrphostin 23 was also less toxic than that with genistein. In vivo studies with high-dose tyrphostin-treatments were compromised due to toxicity of DMSO which was used as a solvent, however, the use of murine model are contemplated to document the efficacy of tyrphostin-treatment in augmenting AAV transduction efficiency.

Thus, the present invention demonstrates that the cellular EGF-R PTK catalyzes phosphorylation of the ssD-BP, a crucial player in AAV-mediated transduction. Given the teachings of the present invention, an understanding of the interactions between EGF-R and the ssD-BP has been established. It may be likely that additional downstream target proteins also are involved. Thus, the teachings of the present invention allow for a better understanding of molecular events involved in high-efficiency AAV transduction which, in turn, will lead to improvements in the optimal use of AAV vectors in human gene therapy.

D. D-Sequence Binding Protein

According to the present invention, there has been identified a D-sequence binding protein which binds the D-sequence of the AAV genome. This molecule is capable of enhancing the transcription of a nucleic acid delivered using an AAV vector. The protein has an apparent molecular weight of 53 kDa. The inventors have identified the partial sequence of D-BP, and postulate that D-BP likely has a sequence of:

DNNRELDLE[I]NRADVLAQYEDIAQ[S][G]KAEA (SEQ ID NO:5; the amino acids within the "[ ]" indicates a weak choice for the major residues at that site)

In addition to the entire D-BP molecule, the present invention also relates to fragments of the polypeptide that may or may not retain the D-sequence binding (or other) activity. Fragments, including the N-terminus of the molecule may be generated by genetic engineering of translation stop sites within the coding region (discussed below). Alternatively, treatment of the D-BP molecule with proteolytic enzymes, known as proteases, can produces a variety of N-terminal, C-terminal and internal fragments. Examples of fragments may include contiguous residues of the D-BP encoding sequence of the full length sequence, ½ of the full length sequence, ⅓ of the full length sequence, ¼ of the full length sequence, ⅕ of the full length sequence, ⅙ of the full length sequence, ⅐ of the full length sequence, ⅛ of the full length sequence, 1/10 of the full length sequence or smaller. Such a fragment may be 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, 400 or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

(i) Structural Features of the Polypeptide

The gene for D-BP encodes a polypeptide that binds to the D-sequence of AAV. In certain preferred embodiments, the D-BP is single stranded D-BP (ssD-BP). In alternative embodiments the D-BP is double stranded D-BP (dsD-BP). The predicted molecular weight of this molecule is 53 kDa. This protein likely is an approximately 400 amino acid protein. Thus, at a minimum, this molecule may be used as a standard in assays where molecular weight and pI are being examined.

(ii) Functional Aspects

When the present application refers to the function of D-BP or "wild-type" activity, it is meant that the molecule in question has the ability to bind or complex the D-sequence of the AAV genome. More specifically, it is desirable that the D-BP activity is able to bind the 3' end of the AAV genome. In so doing, the D-BP will be able to induce AAV DNA replication and augment transgene expression mediated by an AAV vector. Determination of which molecules possess this activity may be achieved using assays familiar to those of skill in the art. For example, transfection of genes encoding D-BP, or variants thereof, into cells that do not have a functional D-BP product, concomitantly with the AAV transgenic constructs to be delivered, will have a greater gene expression than those transfectants that have been transfected with the AAV transgenic construct alone.

Furthermore, dephosphorylation of the cellular D-BP correlates strongly with AAV transduction efficiency. Dephosphorylation of the D-BP facilitates second-strand synthesis of the AAV genome delivered to target cells as a single-stranded DNA molecule, suggesting that manipulation of phosphorylation state of this protein may be exploitable as one of the strategies for significantly improving transduction efficiency of recombinant AAV vectors.

The D-BP is phosphorylated at tyrosine residues, and the phosphorylated form of the D-BP prevents the viral second-strand DNA synthesis and subsequently blocks AAV-mediated transgene expression. Inhibition of cellular protein tyrosine kinases by genistein, a potent inhibitor of protein tyrosine kinases (Akiyama et al., 1987), results in dephosphorylation of the D-BP leading to not only enhancement of transgene expression of recombinant AAV, but also to autonomous replication of wt AAV genome (Qing et al., 1997b). Thus, the host cell D-BP plays a pivotal role in the life cycle of AAV.

(iii) Variants of D-BP

Amino acid sequence variants of the D-BP polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. In preferred embodiments, it may be desirable to produce D-BP proteins that lack tyrosine phosphorylation sites. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those which are within ±1 are particularly preferred, and those within ±0.5 are even more particularly preferred.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0+1); glutamate (+3.0+1); serine (+0.3); asparagine (+0.2); glutamine (+0.2); glycine (0); threonine (−0.4); proline (−0.5+1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within +2 is preferred, those that are within +1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of D-BP, but with altered and even improved characteristics.

(iv) Synthetic Peptides

The present invention also describes smaller D-BP-related peptides for use in various embodiments of the present invention. Because of their relatively small size, the peptides of the invention also can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

(v) Domain Switching

As described in the examples, the present inventors have identified a D-BP gene. These studies are important for at least two reasons. First, they provide a reasonable starting point for searching for homologs, allelic variants and mutants of this gene that may exist in related species, such as rat, rabbit, monkey, gibbon, chimp, ape, baboon, cow, pig, horse, sheep and cat. Upon isolation of these homologs, variants and mutants, and in conjunction with other analyses, certain active or functional domains can be identified. Second, this will provide a starting point for further mutational analysis of the molecule. One way in which this information can be exploited is in "domain switching."

Domain switching involves the generation of chimeric molecules using different but related polypeptides. By comparing the a sequence for D-BP from one species with the D-BP of other species, and with mutants and allelic variants of these polypeptides, one can make predictions as to the functionally significant regions of these molecules. It is possible, then, to switch related domains of these molecules in an effort to determine the criticality of these regions to D-BP function. These molecules may have additional value in that these "chimeras" can be distinguished from natural molecules, while possibly providing the same function.

A structural aspect of D-BP that provides fertile ground for domain switching studies is the putative tyrosine phosphorylation sites. This domain may be substituted for other phosphorylation domains in order to alter the specificity of this function. A further investigation of the homology between D-BP and other proteins containing tyrosine phosphorylation regions is warranted by this observation.

(vi) Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. Fusion to a polypeptide that can be used for purification of the substrate-D-BP complex would serve to isolate and purify the AAV. In another example it will be possible to fuse D-BP to, for example, β-gal, to facilitate affinity purification of AAV genomes.

(vii) Production and Purification of Proteins

It will be desirable to purify D-BP or variants thereof for a variety of reasons including antibody production, and for use in assays to identify molecules that modulate D-BP function as described elsewhere in the application. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

(viii) Antigen Compositions

The present invention also provides for the use of D-BP proteins or peptides as antigens for the immunization of animals relating to the production of antibodies. It is envisioned that either D-BP, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e. pharmaceutically acceptable. Preferred agents are the carriers are keyhole limpet hemocyannin (KLH) or bovine serum albumin (BSA).

E. Nucleic Acids

The present invention also provides, in another embodiment, genes encoding D-BP. The present invention is not limited in scope to these genes, however, as one of ordinary skill in the could, using these nucleic acids, readily identify related homologs in various other species (e.g., rat, rabbit, monkey, gibbon, chimp, ape, baboon, cow, pig, horse, sheep, cat and other species).

In addition, it should be clear that the present invention is not limited to the specific nucleic acids disclosed herein. As discussed below, a "D-BP gene" may contain a variety of different bases and yet still produce a corresponding polypeptide that is functionally indistinguishable, and in some cases structurally distinct, from the D-BP protein disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of D-BP.

(i) Nucleic Acids Encoding D-BP

The present invention describes the D-BP protein. Nucleic acids according to the present invention may encode an entire D-BP gene, a domain of D-BP that expresses a tumor suppressing or phosphatase function, or any other fragment of the D-BP sequences set forth herein. The nucleic acid may be derived from genomic DNA, i.e. cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes."

At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given D-BP from a given species may be represented by natural variants that have slightly different nucleic acid sequences but, nonetheless, encode the same protein (see Table 1 below).

As used in this application, the term "a nucleic acid encoding a D-BP" refers to a nucleic acid molecule that has been isolated free of total cellular nucleic acid. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of the D-BP gene will be sequences that "encode D-BP" Sequences that are essentially the same as those that encode D-BP may also be functionally defined as sequences that are capable of hybridizing to a nucleic acid segment containing the complement of the D-BP encoding gene under standard conditions.

The DNA segments of the present invention include those encoding biologically functional equivalent D-BP proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

(ii) Oligonucleotide Probes and Primers

Naturally, the present invention also encompasses DNA segments that are complementary, or essentially complementary, to the sequence encoding D-BP of the present invention. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of D-BP under relatively stringent conditions such as those described herein. Such sequences may encode the entire D-BP protein or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1200 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C. Formamide and SDS also may be used to alter the hybridization conditions.

One method of using probes and primers of the present invention is in the search for genes related to D-BP or, more particularly, homologs of D-BP from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique usefull in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M 13 phage. These phage vectors are commercially available and their use is generally well known to those skilled in the art. Double stranded plasmids also are routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

(iii) Antisense Constructs

In some cases, it will be necessary to abrogate the function of D-BP. Antisense treatments are one way of addressing this situation. Antisense technology also may be used to "knock-out" function of D-BP in the development of cell lines or transgenic mice for research, diagnostic and screening purposes. Antisense constructs also are contemplated in the context of the heterologous gene being transferred by the AAV vector.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

F. Gene Transfer and Expression (i) Regulatory Elements

In describing both the AAV plasmid, which contains the transgene of interest, and any D-BP containing construct for the purpose of expressing a protein, it should be noted that promoters will be required to drive the transcription of these genes. The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrases "under transcriptional control" or "operably linked" mean that the promoter is in the correct location and orientation in relation to the nucleic acid to control RNA polymerase initiation and expression of the gene.

Within certain embodiments, expression vectors are employed to express the D-BP polypeptide product, which can then be purified and, for example, be used to vaccinate animals to generate antisera or monoclonal antibody with which further studies may be conducted. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products also are provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several elements/promoters which may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

| ENHANCER/PROMOTER |
| --- |
| Immunoglobulin Heavy Chain |
| Immunoglobulin Light Chain |

TABLE 2-continued

ENHANCER/PROMOTER

T-Cell Receptor
HLA DQ α and DQ β
β-Interferon
Interleukin-2
Interleukin-2 Receptor
MHC Class II 5
MHC Class II HLA-DRα
β-Actin
Muscle Creatine Kinase
Prealbumin (Transthyretin)
Elastase I
Metallothionein
Collagenase
Albumin Gene
α-Fetoprotein
τ-Globin
β-Globin
e-fos
c-HA-ras
Insulin
Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 3

| Element | Inducer |
| --- | --- |
| MT II | Phorbol Ester (TPA) |
|  | Heavy metals |
| MMTV (mouse mammary tumor virus) | Glucocorticoids |
| β-Interferon | poly(rI)X |
|  | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

Where a cDNA insert is employed, one typically will desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Transgene Constructs

Transgene expression will be driven by a selected promoter. The promoter selection will depend on the polypeptide to be expressed, the target tissue and the purpose for expression. For example, if the protein is simply to be produced in vitro and purified, a high level promoter will be utilized. If the protein is toxic to the cells, it may be desirable to regulate the expression of the protein such that cells proliferation is maximized prior to polypeptide expression. If the protein's processing or secretion is dependent upon a particular stage in the host cell's cycle, it may be desirable to employ a promoter that is regulated in an appropriate, cell cycle dependent fashion.

(iii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iv) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(v) Delivery of Expression Vectors

The present application proposes the use of AAV expression vectors for delivering a gene to a particular host or target cell. However, as noted above, such host cells express a D-BP that prevents the second strand synthesis of the single-stranded DNA molecule of the AAV genome that is delivered. Thus, in order to increase the efficiency of AAV-mediated gene delivery, it will be desirable to inhibit the action of the D-BP of the host cell. In this embodiment, it may be useful to employ other viruses to deliver the D-BP inhibitory composition. Such viruses may include those that enter cells via receptor-mediated endocytosis, integrate into host cell genome and express viral genes stably and efficiently (Ridgeway, 1988; Nicolas and Rubenstein, 1988; Baichwal and Sugden, 1986; Temin, 1986). These DNA viruses including the papovaviruses (simian virus 40, bovine papilloma virus, and polyoma) (Ridgeway, 1988; Baichwal and Sugden, 1986), adenoviruses (Ridgeway, 1988; Baichwal and Sugden, 1986) and retroviruses (Coffin, 1990; Mann et al., 1983; Nicolas and Rubenstein, 1988; Temin, 1986; Mann et al., 1983). In particular aspects, the D-BP may be inhibited using antisense construct against D-BP which are delivered to the host cell. Furthermore, it is understood that any gene based application in which the above viruses are currently being employed will readily be amenable to delivery mediated by AAV. As such the inhibition of the D-BP of the host cell will prove useful in any such application.

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Although the expression constructs described in the present invention are designed to be encapsulated within an adeno-associated viral vector, it may be desirable that expression constructs for the expression of non-phosphorylated or antisense D-BP be delivered without encapsulation. In such embodiments, non-viral transfer also is contemplated. Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell, the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct containing the D-BP gene may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

In a further embodiment of the invention, the expression construct containing may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

G. Propagation of Vectors and Transformation of Host Cells

Virions can be produced by transfer of the AAV plasmid containing the heterologous gene, followed by inhibition of the D-sequence binding protein. Such inhibition may be achieved by co-transfer with an antisense D-sequence binding protein, or any other agent that will inhibit, eliminate or otherwise abrogate the function of the D-BP. Transfer of the plasmid may be accomplished any standard gene transfer mechanism: calcium phosphate precipitation, lipofection, electroporation, microprojectile bombardment or other suitable means. Following transfer, host cells may further be infected with a helper virus and the virions are isolated and helper virus is inactivated (e.g., heated at 56° C. for one h). The resulting helper free stocks of virions are used to infect appropriate target cells. Mature virions may further be isolated by standard methods, e.g., cesium chloride centrifugation, and to inactivate any contaminating adenovirus.

Function of the vectors of the present invention, i.e. the ability to mediate transfer and expression of the heterologous gene in hematopoietic stem or progenitor cells, can be evaluated by monitoring the expression of the heterologous gene in transduced cells. Obviously, the assay for expression depends upon the nature of the heterologous gene. Expression can be monitored by a variety of methods including immunological, histochemical or activity assays. For example, Northern analysis can be used to assess transcription using appropriate DNA or RNA probes. If antibodies to the polypeptide encoded by the heterologous gene are available, Western blot analysis, immunohistochemistry or other immunological techniques can be used to assess the production of the polypeptide. Appropriate biochemical assays also can be used if the heterologous gene is an enzyme. For example, if the heterologous gene encodes antibiotic resistance, a determination of the resistance of infected cells to the antibiotic can be used to evaluate expression of the antibiotic resistance gene.

Site-specific integration can be assessed, for example, by Southern blot analysis. DNA is isolated from cells transduced by the vectors of the present invention, digested with a variety of restriction enzymes, and analyzed on Southern blots with an AAV-specific probe. A single band of hybridization evidences site-specific integration. Other methods known to the skilled artisan, such as polymerase chain reaction (PCR) analysis of chromosomal DNA can be used to assess stable integration.

H. Methods for Production of Polypeptides In Vitro

In one embodiment, the present invention contemplates the use of AAV vectors to transform cells for the production of mammalian cell cultures. In order for the cells to be kept viable while in vitro and in contact with the expression construct, it is necessary to ensure that the cells are maintained with the correct ratio of oxygen and carbon dioxide and nutrients, but are protected from microbial contamination. Cell culture techniques are well documented and are disclosed herein by reference (Freshner, 1992).

The construct encoding the protein of interest may be transferred by the viral vector, as described above, into appropriate host cells followed by culture of cells under the appropriate conditions. The gene for virtually any polypeptide may be employed in this manner. Examples of useful mammalian cell lines are those that express the appropriate receptor for B19 virus. These include cells derived from bone marrow cells, peripheral blood cells and fetal liver cells.

Bone marrow cells are isolated and enriched for hematopoietic stem cells (HSC), e.g., by fluorescence activated cell sorting as described in Srivastava et al. (1988). HSC are capable of self-renewal as well as initiating long-term hematopoiesis and differentiation into multiple hematopoietic lineages in vitro. HSC are transfected with the vector of the present invention or infected with varying concentrations of virions containing a subject hybrid vector and then assessed for the expression of the heterologous gene. The assay for expression depends upon the nature of the heterologous gene. Expression can be monitored by a variety of methods including immunological, histochemical or activity assays. For example, Northern analysis can be used to assess transcription using appropriate DNA or RNA probes. If antibodies to the polypeptide encoded by the heterologous gene are available, Western blot analysis, immunohistochemistry or other immunological techniques can be used to assess the production of the polypeptide. Appropriate biochemical assays also can be used if the heterologous gene is an enzyme. For example, if the heterologous gene encodes antibiotic resistance, a determination of the resistance of infected cells to the antibiotic can be used to evaluate expression of the antibiotic resistance gene.

An important consideration is the appropriate modification needed for a particular polypeptide. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the protein expressed.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e. a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations. Antibodies are and their uses are discussed further, below.

I. Transgenes

Virtually any transgene may be utilized in the vectors described herein. In a preferred embodiment, the heterologous gene encodes a biologically functional protein, i.e. a polypeptide or protein which affects the cellular mechanism of a cell in which the biologically functional protein is expressed. For example, the biologically functional protein can be a protein which is essential for normal growth of the cell or for maintaining the health of a mammal. The biologically functional protein also can be a protein which improves the health of a mammal by either supplying a missing protein, by providing increased quantities of a protein which is underproduced in the mammal or by providing a protein which inhibits or counteracts an undesired molecule which may be present in the mammal. The biologically functional protein also can be a protein which is a useful protein for investigative studies for developing new gene therapies or for studying cellular mechanisms.

Expression of several proteins that are normally secreted can be engineered into cells. The cDNA's encoding a number of useful human proteins are available. Examples would include soluble CD-4, Factor VIII, Factor IX, von Willebrand Factor, TPA, urokinase, hirudin, interferons, TNF, interleukins, hematopoietic growth factors, antibodies, albumin, leptin, transferin and nerve growth factors.

Expression of non-secreted proteins can be engineered into cells. Two general classes of such proteins can be defined. The first are proteins that, once expressed in cells, stay associated with the cells in a variety of destinations. These destinations include the cytoplasm, nucleus, mitochondria, endoplasmic reticulum, Golgi, membrane of secretory granules and plasma membrane. Non-secreted proteins are both soluble and membrane associated. The second class of proteins are ones that are normally associated with the cell, but have been modified such that they are now secreted by the cell. Modifications would include site-directed mutagenesis or expression of truncations of engineered proteins resulting in their secretion as well as creating novel fusion proteins that result in secretion of a normally non-secreted protein.

p53 currently is recognized as a tumor suppressor gene (Montenarh, 1992). High levels of mutant p53 have been found in many cells transformed by chemical carcinogenesis, ultraviolet radiation, and several viruses, including SV40. The p53 gene is a frequent target of mutational inactivation in a wide variety of human tumors and is already documented to be the most frequently-mutated gene in common human cancers (Mercer, 1992). It is mutated in over 50% of human NSCLC (Hollestein et al., 1991) and in a wide spectrum of other tumors.

The p53 gene encodes a 393-amino-acid phosphoprotein that can form complexes with host proteins such as large-T antigen and E1B. The protein is found in normal tissues and cells, but at concentrations which are generally minute by comparison with transformed cells or tumor tissue.

Interestingly, wild-type p53 appears to be important in regulating cell growth and division. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or directly or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Missense mutations are common for the p53 gene and are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 is not detrimental to normal cells with endogenous wild-type p53. Thus, such constructs might be taken up by normal cells without adverse effects. It is thus proposed that the treatment of p53-associated cancers with wild-type p53 expression constructs will reduce the number of malignant cells or their growth rate. Furthermore, recent studies suggest that some p53 wild-type tumors are also sensitive to the effects of exogenous p53 expression.

The major transitions of the eukaryotic cell cycle are triggered by cyclin-dependent kinases, or CDK's. One CDK, cyclin-dependent kinase 4 (CDK4), regulates progression through the $G_1$ phase. The activity of this enzyme may be to phosphorylate Rb at late $G_1$. The activity of CDK4 is controlled by an activating subunit, D-type cyclin, and by an inhibitory subunit, e.g., p16$^{INK4}$, which has been biochemically characterized as a protein that specifically binds to and inhibits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

p16$^{INK4}$ belongs to a newly described class of CDK-inhibitory proteins that also includes p16$^B$, p21$^{WAF1, CIP1, SDI1}$, and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994a; Kamb et al., 1994b; Mori et al., 1994; Okamoto et al., 1994; Nobori et al., 1995; Orlow et al., 1994; Arap et al., 1995). Restoration of wild-type p16$^{INK4}$ function by transfection with a plasmid expression vector reduced colony formation by some human cancer cell lines (Okamoto, 1994; Arap, 1995).

C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, Cheung et al. (1993a; 1993b and 1993c) demonstrated that the first Ig domain of C-CAM is critical for cell adhesion activity.

Cell adhesion molecules, or CAMs are known to be involved in a complex network of molecular interactions that regulate organ development and cell differentiation (Edelman, 1985). Recent data indicate that aberrant expression of CAMs may be involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. C-CAM now has been shown to suppress tumor growth in vitro and in vivo.

Other tumor suppressors that may be employed according to the present invention include RB, APC, DCC, NF-1, NF-2, WT-1, MEN-I, MEN-II, zac1, p73, BRCA1, VHL, FCC, MMAC1, MCC, p16, p21, p57, C-CAM, p27 and BRCA2. Inducers of apoptosis, such as Bax, Bak, Bcl-X$_s$, Bik, Bid, Harakiri, Ad E1B, Bad and ICE-CED3 proteases, similarly could find use according to the present invention.

Various enzyme genes are of interest according to the present invention. Such enzymes include cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase.

Hormones are another group of gene that may be used in the vectors described herein. Included are growth hormone, prolactin, placental lactogen, luteinizing hormone, follicle-stimulating hormone, chorionic gonadotropin, thyroid-stimulating hormone, leptin, adrenocorticotropin (ACTH), angiotensin I and II, β-endorphin, β-melanocyte stimulating hormone (β-MSH), cholecystokinin, endothelin I, galanin, gastric inhibitory peptide (GIP), glucagon, insulin, lipotropins, neurophysins, somatostatin, calcitonin, calcitonin gene related peptide (CGRP), β-calcitonin gene related peptide, hypercalcemia of malignancy factor (1–40), parathyroid hormone-related protein (107–139) (PTH-rP), parathyroid hormone-related protein (107–111) (PTH-rP), glucagon-like peptide (GLP-1), pancreastatin, pancreatic peptide, peptide YY, PHM, secretin, vasoactive intestinal peptide (VIP), oxytocin, vasopressin (AVP), vasotocin, enkephalinamide, metorphinamide, alpha melanocyte stimulating hormone (alpha-MSH), atrial natriuretic factor (5–28) (ANF), amylin, amyloid P component (SAP-1), corticotropin releasing hormone (CRH), growth hormone releasing factor (GHRH), luteinizing hormone-releasing hormone (LHRH), neuropeptide Y, substance K (neurokinin A), substance P and thyrotropin releasing hormone (TRH). The cDNA's encoding a number of therapeutically useful human proteins are available. Other proteins include protein processing enzymes such as PC2 and PC3, and PAM, transcription factors such as IPF1, and metabolic enzymes such as adenosine deaminase, phenylalanine hydroxylase, glucocerebrosidase.

Other classes of genes that are contemplated to be inserted into the vectors of the present invention include interleukins and cytokines. Interleukin 1 (IL-1), IL-2, IL-3, IL-4, IL-5, IL-6, IL-7, IL-8, IL-9, IL-10, IL-11IL-12, GM-CSF and G-CSF.

Examples of diseases for which the present viral vector would be useful include, but are not limited to, adenosine deaminase deficiency, human blood clotting factor IX deficiency in hemophilia B, and cystic fibrosis, which would involve the replacement of the cystic fibrosis transmembrane receptor gene. The vectors embodied in the present invention could also be used for treatment of hyperproliferative disorders such as rheumatoid arthritis or restenosis by transfer of genes encoding angiogenesis inhibitors or cell cycle inhibitors. Transfer of prodrug activators such as the HSV-TK gene can be also used in the treatment of hyperploiferative disorders, including cancer.

Other therapeutics genes might include genes encoding antigens such as viral antigens, bacterial antigens, fungal antigens or parasitic antigens. Viruses include picornavirus, coronavirus, togavirus, flavirviru, rhabdovirus, paramyxovirus, orthomyxovirus, bunyavirus, arenvirus, reovirus, retrovirus, papovavirus, parvovirus, herpesvirus, poxvirus, hepadnavirus, and spongiform virus. Preferred viral targets include influenza, herpes simplex virus 1 and 2, measles, small pox, polio or HIV. Pathogens include trypanosomes, tapeworms, roundworms, helminths. Also, tumor markers, such as fetal antigen or prostate specific antigen, may be targeted in this manner. Preferred examples include HIV env proteins and hepatitis B surface antigen. Administration of a vector according to the present invention for vaccination purposes would require that the vector-associated antigens be sufficiently non-immunogenic to enable long term expression of the transgene, for which a strong immune response would be desired. Preferably, vaccination of an individual would only be required infrequently, such as yearly or biennially, and provide long term immunologic protection against the infectious agent.

Cells engineered to produce such proteins could be used for either in vitro production of the protein or for in vivo, cell-based therapies. In vitro production would entail purification of the expressed protein from either the cell pellet for proteins remaining associated with the cell or from the conditioned media from cells secreting the engineered protein. In vivo, cell-based therapies would either be based on secretion of the engineered protein or beneficial effects of the cells expressing a non-secreted protein.

Engineering mutated, truncated or fusion proteins into cells also is contemplated. Examples of each type of engineering resulting in secretion of a protein are given (Ferber et al., 1991; Mains et al., 1995). Reviews on the use of such proteins for studying the regulated secretion pathway also are cited (Burgess and Kelly, 1987; Chavez et al., 1994).

J. Generating Antibodies Reactive with D-BP

In another aspect, the present invention contemplates an antibody that is immunoreactive with a D-BP molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to D-BP-related antigen epitopes. Additionally, it is proposed that monoclonal antibodies specific to the particular D-BP of different species may be utilized in other useful applications In general, both polyclonal and monoclonal antibodies against D-BP may be used in a variety of embodiments. For example, they may be employed in antibody cloning protocols to obtain cDNAs or genes encoding other D-BP. They may also be used in inhibition studies to analyze the effects of D-BP related peptides in cells or animals. Anti-D-BP antibodies will also be useful in immunolocalization studies to analyze the distribution of D-BP during various cellular events, for example, to determine the cellular or tissue-specific distribution of D-BP polypeptides under different points in the cell cycle. A particularly usefull application of such antibodies is in purifying native or recombinant D-BP, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin also can be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified D-BP protein, polypeptide or peptide or cell expressing high levels of D-BP. The immunizing composition is administered in a manner effective to stimulate antibody producing cells. Rodents such as mice and rats are preferred animals, however, the use of rabbit, sheep frog cells also is possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods also is appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three wk) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

K. Methods for Screening Active Compounds

The present invention also contemplates the use of D-BP and active fragments, and nucleic acids coding therefor, in the screening of compounds for activity in either stimulating D-BP activity, overcoming the lack of D-BP or blocking the effect of a mutant D-BP molecule. These assays may make use of a variety of different formats and may depend on the kind of "activity" for which the screen is being conducted. Contemplated functional "read-outs" include viral titer, binding to a compound, inhibition of binding to a substrate, ligand, receptor or other binding partner by a compound, phosphorylation of D-BP, dephosphorylation of D-BP, inhibition or stimulation of transgene expression.

(i) In Vitro Assays

In one embodiment, the invention is to be applied for the screening of compounds that bind to the D-BP molecule or fragment thereof. The polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of D-BP to a natural or artificial substrate or binding partner (D-sequence). Competitive binding assays can be performed in which one of the agents (D-BP, binding partner or compound) is labeled. Usually, the polypeptide will be the labeled species. One may measure the amount of free label versus bound label to determine binding or inhibition of binding.

Another technique for high throughput screening of compounds is described in WO 84/03564. Large numbers of small peptide test compounds are synthesized on a solid substrate, such as plastic pins or some other surface. The peptide test compounds are reacted with D-BP and washed. Bound polypeptide is detected by various methods.

Purified D-BP can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the D-BP active region to a solid phase.

Various cell lines containing wild-type or natural or engineered mutations in D-BP can be used to study various functional attributes of D-BP and how a candidate compound affects these attributes. Methods for engineering mutations are described elsewhere in this document. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of D-BP, or related pathways, may be explored. This may involve assays such as those for protein expression, enzyme function, substrate utilization, phosphorylation states of D-BP, mRNA expression (including differential display of whole cell or polyA RNA) and others.

(ii) Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for D-BP or a fragment thereof. This could be accomplished by x-ray crystallography, computer modeling or by a combination of both approaches. An alternative approach, "alanine scan," involves the random replacement of residues throughout molecule with alanine, and the resulting affect on function determined.

It also is possible to isolate a D-BP specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved D-BP activity or which act as stimulators, inhibitors, agonists, antagonists or D-BP or molecules affected by D-BP function. By virtue of the availability of cloned D-BP sequences, sufficient amounts of D-BP can be produced to perform crystallographic studies. In addition, knowledge of the polypeptide sequences permits computer employed predictions of structure-function relationships.

L. Methods of Altering D-BP activity

As stated above, the present invention provides methods for increasing the transduction efficiency of AAV mediated transcription in for example gene therapy. These methods exploit the inventors' observation, described in detail herein, that the phosphorylation of D-BP appears to decrease the efficiency of AAV transduction. Further the inventors have shown that EGF-R PTK is responsible for the phosphorylation of D-BP. At its most basic, this embodiment will function by reducing the in vivo activity of D-BP in a host cell to which an AAV vector comprising an expression cassette has been provided for the purposes of gene delivery. This may be accomplished by one of several different mechanisms. First, one may block the expression of the D-BP. Second, one may directly block the function of the D-BP by providing an agent that binds to, or otherwise inactivates the D-BP protein. And third, one may indirectly block the effect of D-BP by interfering with one or more factors that influence the phosphorylation of D-BP.

(i) Blocking Expression of D-BP

The most direct method for blocking D-BP expression is via antisense technology. Antisense technologies have been described elsewhere in the specification. (ii) Blocking Function of D-BP In another embodiment, it may be desirable to block the function of a D-BP polypeptide rather than inhibit its expression. This can be accomplished by use of organochemical compositions that interfere with the function of D-BP, by use of an antibody that blocks an active site or binding site on D-BP, or by use of a molecule that mimics a D-BP target.

With respect to organochemical inhibitors, such compounds may be identified in standard screening assays. For example, given the knowledge that D-BP is activated as a result of phosphorylation by EGF-R, and it is this activation that produces the upregulation of binding that prevents the AAV transduction, it now is possible to provide an inhibitor of EGF-R in vivo to an appropriate animal, e.g., a mouse, and look for increased transduction efficiency. Once identified, such an inhibitor may be used to inhibit D-BP function in a therapeutic context.

With respect to antibodies, it should be noted that not all antibodies are expected to have the same functional effects on their targets. This stems both from the differing specificities of antibodies and their character, i.e. their isotype. Thus, it will be useful to generate a number of different monoclonal and polyclonal preparations against D-BP. It also may prove useful to generate anti-idiotypic antibodies to anti-D-BP antibodies. These compounds may be used as probes for D-BP putative binding partners.

The methods by which antibodies are generated are well known to those of skill in the art, and are detailed elsewhere in the specification. Again, antibodies that bind to D-BP may be screened for other functional attributes.

A particularly useful antibody for blocking the action of D-BP is a single chain antibody. Methods for the production of single-chain antibodies are well known to those of skill in the art. The skilled artisan is referred to U.S. Pat. No. 5,359,046, (incorporated herein by reference) for such methods. A single chain antibody, preferred for the present invention, is created by fusing together the variable domains of the heavy and light chains using a short peptide linker, thereby reconstituting an antigen binding site on a single molecule.

Single-chain antibody variable fragments (Fvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

With respect to inhibitors that mimic D-BP targets, the use of mimetics provides one example of custom designed molecules. Such molecules may be small molecule inhibitors that specifically inhibit D-BP protein activity or binding to D-sequence. Such molecules may be sterically similar to the actual target compounds, at least in key portions of the target's structure and or organochemical in structure. Alternatively these inhibitors may be peptidyl compounds, these are called peptidomimetics that have been described elsewhere in the application.

(iii) Blocking of D-BP Phosphorylation

D-BP is a cellular phosphorylated protein that binds to the D-sequence of the adeno-associated viral genome and thereby prevent second strand synthesis of the AAV genome that is delivered to target cells as a single-stranded DNA molecule. The present inventors further demonstrated that the D-BP is phosphorylated by the EGF-R family of tyrosine kinases. This observation may be advantageously exploited in gene deliver applications. In order to prevent D-BP from interacting with the D-sequence of AAV, one would inhibit the phosphorylation of D-BP. Such inhibition of the phosphorylation of this protein thus may be exploited as one of the strategies for significantly improving transduction efficiency of recombinant AAV vectors.

One may take a variety of different approaches to effect the inhibition of the phosphorylation of D-BP. For example, one may generate antibodies against the EGF-R and then provide the antibodies to the subject in question, thereby blocking interaction of EGF-R with to the target D-BP molecule.

In yet another embodiment, antisense methodologies directed against EGF-R may be employed in order to inhibit the interaction of EGF-R with its D-BP. In this regard, the skilled artisan is referred to U.S. Pat. No. 5,610,288, which describes antisense polynucleotide inhibition of epidermal human growth factor receptor expression and is specifically incorporated herein by reference. Alternatively, one may design a polypeptide or peptide mimetic that is capable of interacting with the EGF-R protein kinase in the same fashion as D-BP, but without any D-BP-like effect on the target, i.e. without the D-BP being able to interact with the D-sequence.

In a preferred embodiment, the present invention will provide an agent that binds competitively to D-BP. In a more preferred embodiment, the agent will have an even greater affinity for the D-BP than does EGF-R protein kinase does. Affinity for the D-BP can be determined in vitro by performing kinetic studies on binding rates. Specifically, in the present invention it has been shown that agents such as hydroxyurea, genistein (U.S. Pat. No. 5,554,519), tyrphostin 1, tyrphostin 23, tyrphostin 63, tyrphostin 25, tyrphostin 46, and tyrphostin 47 (Dvir et al., 1991) inhibit the kinase activity of EGF-R which phosphorylates D-BP and will therefore increase the efficiency of AAV-mediated transgene expression. The tyrphostin-type inhibitors of tyrosine kinase activity are well known to those of skill in the art, see for example, Faaland et al., 1991; Ohmichi et al., 1993; Kaur, 1994; Markovits, et al., 1994 (each incorporated herien by reference). The artisan skilled in the art is particularly referred to U.S. Pat. No. 5,789,427; U.S. Pat. No. 5,763,198 and U.S. Pat. No. 5,773,476 (each specifically incorporated herien by reference) for additional disclosure regarding methods and compositions relating to inhibitors of EGF-R protein kinases. U.S. Pat. No. 5,587,459 (specifically incorporated herien by reference) provides methods and compositions related to inhibiting receptor associated tyrosine kinases.

Other compounds may be developed based on computer modeling and predicted higher order structure, both of the D-BP molecule, and of the EGF-R kinase molecule. This approach has proved successful in developing inhibitors for a number of receptor-ligand interactions.

M. Methods of Therapy

The vectors of the present invention are useful for gene therapy, the therapy consists of administering vector and abrogating the function of the host cell D-BP. In particularly preferred embodiments, the vectors of the present invention can direct cell-specific expression of a desired gene, and thus are useful in the treatment of hemoglobinopathies. Such maladies include thalassemia, sickle-cell anemia, diabetes, and cancer. The heterologous gene, in this context, can be the normal counterpart of one that is abnormally produced or underproduced in the disease state, for example β-globin for the treatment of sickle-cell anemia, and α-globin, β-globin or γ-globin in the treatment of thalassemia. The heterologous gene can encode antisense RNA as described hereinabove. For example, α-globin is produced in excess over β-globin in β-thalassemia. Accordingly, β-thalassemia can be treated in accordance with the present invention by gene therapy with a vector in which the heterologous gene encodes an antisense RNA. The antisense RNA is selected such that it binds to a target sequence of the α-globin mRNA to prevent translation of α-globin, or to a target sequence of the α-globin DNA such that binding prevents transcription of α-globin DNA. In the treatment of cancer the heterologous gene can be a gene associated with tumor suppression, such as retinoblastoma gene, p53, p16, p21 or the gene encoding tumor necrosis factor.

The use of the vectors of the present invention for the treatment of disease involves, in one embodiment, the transduction of hematopoeitic stems cells or progenitor cells with the claimed vectors in combination with inhibition of the D-BP of the host protein. Transduction is accomplished, following preparation of mature virions containing the AAV vectors, by infection of HSC or progenitor cells therewith. Transduced cells may be located in patients or transduced ex vivo and introduced or reintroduced into patients, e.g., by intravenous transfusion (Rosenberg, 1990).

In ex vivo embodiments, HSC or progenitor cells are provided by obtaining bone marrow cells from patients and optionally enriching the bone marrow cell population for HSC. HSC can be transduced by standard methods of transfection or infected with mature virions for about one to two h at about 37° C. Stable integration of the viral genome is accomplished by incubation of HSC at about 37° C. for about one week to about one month. The stable, site-specific integration and erythroid cell-specific expression is assessed as described above. After the transduced cells have been introduced into a patient, the presence of the heterologous gene product can be monitored or assessed by an appropriate assay for the gene product in the patient, for example in peripheral red blood cells or bone marrow of the patient when expression is erythroid cell-specific. As described above, the specific assay is dependent upon the nature of the heterologous gene product and can readily be determined by one skilled in the art.

In certain embodiments, the present invention provides examples of increasing the transduction efficiency of AAV mediate gene transcription by inhibiting the phosphorylation. More particularly, the present invention contemplate inhibiting tyrosine kinase mediated phosphorylation of EGF-R mediated phosphorylation of D-BP. More specifically the present invention demonstrates that EGF-R mediates phosphorylation of D-BP, thus inhibition of EGF-R alone or in combination with inhibition of D-BP function will result in an advantageous increase in AAV mediated gene transcription.

(i) Combined Therapy

Transduction using AAV vectors is at best inefficient. The present invention has described methods of increasing the efficiency of AAV-mediated gene transcription by providing expression constructs in combination with D-BP inhibition. D-BP transcription inhibiting function of D-BP has been attributed to the phosphorylated form of D-BP. Thus, efficient transcription may be achieved by providing the expression construct containing the transgene in combination with an expression construct containing an antisense D-BP or a D-BP that is phosphorylated. Alternatively, the host D-BP may be inhibited by provision of a phosphorylation inhibitor in combination with the transgene expression construct.

To inhibit D-BP phosphorylation using the methods and compositions of the present invention, one would generally contact a "target" cell with a D-BP antisense expression construct a phosphorylation inhibitor, or D-BP inhibitor as identified above (agent), and the transgenic construct (gene therapy). These compositions would be provided in a combined amount effective to inhibit the D-BP activity of the cell. This process may involve contacting the cells with the gene therapy and the D-BP inhibiting agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the gene therapy or the other agent will be desired. Various combinations may be employed, where the gene therapy is "A" and the other agent is "B", as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. Again, to achieve increased transcription of the gene product, both agents are delivered to a cell in a combined amount effective to increase transcription.

Agents or factors suitable for use in a combined therapy are any chemical compound or treatment method that decreases the D-BP to AAV binding activity. Such agents may be antisense D-BP constructs, non-phosphorylated D-BP constructs or inhibitors of D-BP phosphorylation.

Phosphorylation inhibitors are well known to those of skill in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the regional delivery of vector constructs to patients in need of gene therapy in combination with the D-BP inhibitory agent will be a very efficient method for delivering a therapeutically effective gene to counteract the clinical disease. Similarly, the phosphorylation inhibitor may be directed to a particular, affected region of the subjects body. Alternatively, systemic delivery of expression construct and/or the agent may be appropriate in certain circumstances, for example, where extensive metastasis has occurred.

N. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

O. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 1

Materials and Methods
Cells, Plasmids, and Viruses

Human HeLa (a cervical carcinoma cell line), KB (a nasopharyngeal carcinoma cell line), the human epidermoid carcinoma cell line A431, the human lung small-cell carcinoma cell line H69, the human erythroleukemia cell line K562, and 293 (an adenovirus-transformed embryonic kidney cell line) cells were obtained from the American Type Culture Collection (ATCC, Rockville, Md.). M07e, a human megakaryocytic leukemia cell line, and K562, a human erythroleukemia cell line, were obtained respectively from Hal E. Broxmeyer and Hiremagalur N. Jayaram (Indiana University School of Medicine, Indianapolis, Ind.). Monolayer cultures of HeLa, A431, KB and 293 cells and suspension cultures of H69, M07e and k562 cells were maintained in Iscove's-modified Dulbecco's medium (IMDM) supplemented with 10% fetal bovine serum (FBS) and 1% antibiotics.

Murine Sca-1$^+$, lin$^-$ primitive hematopoietic stem/progenitor cells were isolated from C57B16/EJ mice as previously described (Ponnazhagan et al., 1997c). Human CD34$^+$ primitive hematopoietic stem/progenitor cells were isolated from low-density bone marrow cells obtained from hematologically normal volunteer donors as previously described (Ponnazhagan et al., 1997b). These protocols were approved by the Institutional Laboratory Animals and Human Subjects Committees, respectively. Human AAV and adenovirus type 2 (Ad2) stocks were obtained from Kenneth I. Berns (Cornell University Medical College, New York, N.Y.) and Kenneth H. Fife (Indiana University School of Medicine, Indianapolis, Ind.), respectively.

A recombinant plasmid, pAdE4orf6 (Ferrari et al., 1996), was obtained from Richard J. Samulski (University of North Carolina, Chapel Hill, N.C.). A recombinant plasmid containing a deletion mutation in the E4orf6 gene was constructed by deleting a 130 bp fragment between EcoRV and BbsI sites within the E4orf6 gene followed by re-ligation to generate a plasmid, designated pKY-4, using standard techniques (Sambrook et al., 1989). Recombinant AAV helper plasmid, pAAV/Ad (Samulski et al., 1989). The recombinant plasmid pCHCEGFR containing the human cytomegalovirus immediate-early promoter (CMVp)-driven cDNA for human epidermal growth factor receptor (EGF-R) has also been described previously (Miller et al., 1994), and was generously provided by Francis G. Kern (Georgetown University Medical Center, Washington, D.C.). Recombinant AAV vector constructs, pCMVp-lacZ (containing the β-galactosidase gene under the control of the cytomegalovirus immediate-early promoter) and pWP-8A (containing the herpesvirus thymidine kinase promoter-driven gene for resistance to neomycin) have been described previously (Nahreini et al., 1993). High-titers (~$1\times10^{11}$–$1\times10^{12}$ particles/ml) of each of the recombinant vectors (vCMVp-lacZ and vTc-Neo) were generated and purified on CsCl equilibrium density gradients as previously described (Kube et al., 1997; Ponnazhagan et al., 1997a; 1997b; 1997c; 1996; 1997d; Qing et al., 1997a; Srivastava et al., 1996; Zhou et al., 1996).

In some studies, TRAN 35S-Label (sp. act., 1,206 Ci/mmol, ICN Pharmaceuticals Inc., Irvine, Calif.) was used to generate radiolabeled AAV as previously described (Kube et al., 1997). Briefly, 293 cells were co-infected with wt AAV (200 particles/cell) and adenovirus 2 (10 pfu/cell) and maintained in the presence of the radiolabel (35 μCi/ml) in cysteine and methionine-free Eagle's minimum essential medium (EMEM) supplemented with 10% FBS and 1% L-glutamine. Radiolabeled AAV particles were also purified by CsCl equilibrium density gradients as described above. Physical particle titers of recombinant vector stocks were determined by quantitative DNA slot blot analysis (Kube and Srivastava, 1997). Physical particle:infectious particle ratio (approximately 1000:1), and the contaminating wild-type AAV-like particle titer (approximately 0.01%) in the recombinant vector stocks were determined as previously described (Kube et al., 1997; Wang et al., 1998).

AAV Binding Assays

AAV-binding studies with HeLa, KB, and 293 cells were carried out as described by Mizukami et al. (1996) with the following modifications. Briefly, [$^{35}$S]-methionine-labeled wt AAV ($1\times10$ particles) were mixed with $1\times10$ cells in triplicate in serum-free IMDM containing 1% bovine serum albumin (BSA) and incubated at 4° C. for 1 h. Mock-infected cells were also included in each assay. M07e cells, from a human megakaryocytic leukemia cell line known to be resistant to AAV infection (Ponnazhagan et al., 1996), were used as a negative control under identical conditions. Cells were washed three times with 1×PBS, resuspended in scintillation fluid and the bound radioactive counts were determined using a Beckman LS3801 liquid scintillation counter. In competition studies, a 30-fold excess of unlabeled wt AAV particles were added along with the $^{35}$S-labeled virus and binding assays were performed as described above.

AAV DNA Replication Assays

Approximately $5\times10^5$ HeLa cells were plated in 6 cm dishes for 12 h followed by either no treatment, or treatment with 80 mM HU for 24 h, 150 μM genistein (Aikyama et al., 1987), or 1 mM sodium ortho-vanadate (NaOV) (Kumagai and Dunphy, 1996; Dudek et al., 1996) for 2 h. Cells were then infected with the wt AAV at a multiplicity of infection (moi) of 2. Low $M_r$ DNA samples were isolated at various times post-infection by the procedure described by Hirt (1967), and analyzed on Southern blots using a $^{32}$P-labeled AAV coding sequence-specific DNA probe as previously described (Wang et al., 1996; 1995).

In some studies, the appropriate AAV DNA substrate containing the 3' hairpin structure were prepared and labeled with [γ-$^{32}$P] ATP (3,000 Ci/mmol) by using T4 polynucleotides kinase as described previously (Wang et al., 1997). The labeled substrate was boiled, quickly chilled, and used in DNA replication assay in the presence of all four unlabeled dNTPs and the Klenow fragment of E. coli DNA polymerase I. 20 ng of either the phosphorylated or the dephosphorylated form of the ssD-sequence affinity column-purified ssD-BP was added to the reaction mixture and incubated for 15 min. at 25° C. prior to adding the Klenow enzyme to examine the effect of the ssD-BP on AAV DNA replication (second-strand DNA synthesis). The reaction mixtures were electrophoresed on 6% polyacrylamide gels. Gels were dried in vacuuo and autoradiographed at −70° C.

Cellular Kinase Inhibitors and Treatment Conditions.

Genistein, apigenin, tyrphostin 1, 23, 25, 46, 47, 51, 63, AG126, AG1288, AG1295, AG1296, and AG1478 were obtained from Sigma Chemical Co. (St. Louis, Mo.). Staurosporine, LY294002, wortmannin, and tyrphostin A48 were obtained from CalBiochem (La Jolla, Calif.). Herbimycin A was obtained from Gibco-BRL, Life Technologies (Grand Island, N.Y.). Stock solutions of genistein (150 mM), tyrphostin A48 (500 mM), staurosporine (1 mM), wortmannin (10 mM), herbimycin A (1 mM), LY294002 (200 mM) in dimethyl sulfoxide (DMSO), and hydroxyurea (HU) (1M) in phosphate-buffered saline (PBS) were stored at −20° C. and diluted into IMDM for use in studies. Stock solutions of apigenin (500 mM), tyrphostin 1, 23, 25, 46, 47, 51, 63, AG126, AG1288, AG1295, AG1296, and AG1478 (500 mM) in DMSO were stored at 4° C. and diluted into IMDM for use in studies. Cells were either mock-treated or treated with various concentrations of genistein, apigenin, wortmannin, staurosporine, herbimycin A, LY294002, and tyrphostin separately for 2 h at 37° C. Chemical treatment with HU was for 16 h at 37° C. Following treatments, cells were washed twice with PBS and were either mock-infected or infected with the recombinant AAV as described below.

Recombinant AAV Infection, and Analysis of AAV-mediated Transduced Gene Expression Recombinant AAV vectors were used to infect cells at various multiplicity of infection (moi) ranging between 4–20 (~$2 \times 10^{-1 \times 10^5}$ particles/cell). Briefly, cells were incubated with the virus in a volume of 100 µl serum-free IMDM for 2 h at 37° C. Expression of the transduced lacZ gene was analyzed 24–48 h post-infection (p.i.) by X-gal staining and enumerating blue cells under a Nikon inverted light microscope as previously described (Ponnazhagan et al., 1997c; Ponnazhagan et al., 1996). For expression of the transduced neo gene, infected cells were incubated in the presence of 400 µg/ml of active concentration of the drug G418, a neomycin analogue (Sigma Chemical Co., St. Louis, Mo.), and G418-resistant colonies were enumerated 14 days p.i. following staining with methylene blue as previously described (Ghiringhelli and Romanowski, 1994).

In another transduction assay, approximately equivalent numbers of cells were washed once with IMDM and then infected with the recombinant vCMVp-lacZ vector at an infectious particle multiplicity of infection (MOI) of 2 or 4, as indicated. Forty eight h post-infection (p.i.), cells were fixed and stained with X-gal (5-bromo-4-chloro-3-indolyl β-D-galactopyranoside) and the numbers of blue cells were enumerated as previously described (Ponnazhagan et al., 1997C; Ponnazhagan et al., 1996; Ponnazhagan et al., 1997D).

Chemical Toxicity Assay.

Approximately $5 \times 10^5$ HeLa cells were seeded in 12-well dishes and allowed to adhere for 24 h. Cells were then treated with 150 µM genistein, 500 µM tyrphostin 1 or tyrphostin 23 or an equivalent volume of DMSO for 2 h, or 10 mM HU for 16 h at 37° C. followed by washing twice with IMDM and incubation at 37° C. Twenty four h post-treatment, cells were trypsinized and plated into five 10-cm dishes. Twelve days later, cells that led to colony formation were stained with methylene blue and numbers of colonies were enumerated as previously described (Ghiringhelli and Romanowski, 1994).

Preparation of whole cell extracts (WCE)

WCE were prepared according to the method described by Muller (1987). The WCE from the HeLa cells was prepared under the following conditions: 1) cells were maintained either in 10% FBS, or in 0.5% FBS for 14 days, or treated with 80 mM HU for 24 h (Russell et al., 1995) before harvesting the cells; 2) cells were either mock-infected, or infected with the wt AAV at a multiplicity of infection (moi) of 1 or 10, infected with Ad2, or co-infected with wt AAV+Ad2 for 36 h prior to harvesting the cells as previously described (Wang et. al., 1996; Kotin et al., 1990) cells were either mock-transfected, or transfected separately with plasmids pWP-7A (Nahreini et al., 1993), pWP-19 (Nahreini et al., 1993), or pCMV-E4orf6 (Ferrari et al., 1996), using the lipofectamine reagent by the transfection protocol supplied by the vendor (GIBCO-BRL, Gaithersburg, Md.).

In some studies, cells were either mock-treated, or treated with 150 µM genistein (a protein tyrosine kinase inhibitor) or 1 mM sodium ortho-vanadate (NaOV, a protein phosphatase inhibitor) for 2 h. In other studies, WCE were prepared from cells that were either mock-transfected, or transfected separately with plasmids pAdE4orf6 or pKY-4 using the lipofectamine reagent by the transfection protocol supplied by the vendor (Gibco-BRL, Gaithersburg, Md.). For analyses of mouse tissues, individual organs from three C57B 16/EJ animals each were obtained and pulverized separately using the MSK cell homogenizer according to the preparation protocol supplied by the vendor (B. Braun Biotech Inc., Allentown, Pa.). Total protein concentrations of WCE were determined by the Bio-Rad protein assay kit (Bio-Rad Laboratories, Hercules, Calif.), and the extracts were frozen in liquid $N_2$ and stored at −70° C.

Electrophoretic Mobility-shift Assays (EMSA)

EMSA were performed essentially as described previously (Wang et al., 1996; 1997). Briefly, DNA-binding reactions were performed in a volume of 20 µl with 2 µg poly (dI-dC), 2 µg bovine serum albumin (BSA) and 12% glycerol in HEPES buffer (pH 7.9). Ten µg of protein from each WCE were pre-incubated for 10 min at 25° C. followed by the addition of 10,000 cpm of $^{32}P$-labeled D(−)-sequence synthetic oligonucleotide (5'-AGGAACCCCTAGTGATGGAG-3' SEQ ID NO:1) in the reaction mixture. In some studies, EMSA were also carried out with β-labeled double-stranded D(±)-sequence oligonucleotide which was prepared by annealing the complementary D(−) and D(+) sequences (5'-CTCCATCACTAGGGGTTCCT-3' SEQ ID NO:2) followed by purification on 10% polyacrylamide gels as previously described (Wang et al., 1996). The binding reaction was allowed to proceed for 30 min at 25° C. and the bound complexes were separated from the unbound probe on low-ionic strength 4% polyacrylamide gels with recirculating Tris-acetate-EDTA (TAE) buffer (pH 7.9) containing 6.72 mM Tris-HCl, 3.3 mM sodium acetate, and 1 mM EDTA as previously described (Wang et al., 1996; 1997). Gels were dried in vacuuo and autoradiographed at −70° C. The ratio of dephosphorylated to phosphorylated forms of ssD-BP in various cell types was determined using autoradiography.

Autoradiograms were scanned using a Digital imaging system alphaimager (Alpha Innotech, Co., San Leandro, Calif.). In competition studies, increasing concentrations of unlabeled D-sequence, or a non-AAV substitute sequence (S-sequence) (5'-CCAATATTAGATCTGATATCA-3' SEQ ID NO:3) (Wang et al., 1996; Wang et al., 1995), or the AAV-cap sequence (5'-ACCGTGGATACTAATGGCGTG-3' SEQ ID NO:4), were added to the reaction mixtures prior to addition of the radiolabeled D-sequence probe for 10 min; this was followed by incubation with the labeled probe as described above.

Southern Blot Analysis of the Recombinant AAV Genome Integration

Total genomic DNA was isolated from individual neo$^R$ clones by standard methods (Sambrook et al., 1989). Equivalent amounts of DNA samples were digested with various restriction endonucleases under the conditions specified by the supplier (Boehringer Mannheim Biochemicals, Indianapolis, Ind.) and the digested products were electrophoresed on 0.8% agarose gels. Separated DNA fragments were transferred to nitrocellulose filters by the method described by Southern (1975) and hybridized with $^{32}$P-labeled DNA probes specific for the neo gene as previously described (Ponnazhagan et al., 1997a).

EGF-binding Assay

EGF-binding studies were carried out as previously described by Livneh et al. (1986) and Gamou et al. (1987), with the following modifications. Briefly, 5×10$^4$ cells were washed twice with IMDM containing 1% BSA. One ml of IMDM containing 1% BSA was added to all cells either with 0.5 ng/ml $^{125}$I-EGF obtained from Amersham (Arlington Heights, Ill.) alone or with 200-fold excess unlabeled EGF (Sigma Chemical Co., St. Louis, Mo.). Cells were incubated for 90 min at room temp. Following incubation, cells were washed four times with IMDM containing 1% BSA and solubilized with 1 ml 0.5 N NaOH for 30 min at 37° C. Radioactivity of lysates was determined in a Beckman Gamma counter. Specific binding was calculated as the total radioactivity minus the non-specific (cell-associated) radioactivity.

Stable Transfection with the EGF-R Expression Plasmid.

Transfection of 293 cells with pCHCEGFR plasmid DNA was carried out using the Qiagen Superfect reagent according to the protocol provided by the vendor (Qiagen, Valencia, Calif.). Hygromycin was added at a final concentration of 300 mg/ml 48 h post-transfection, and individual hygromycin-resistant 293 cell clones were isolated after 14 days of selection.

In Vitro Phosphorylation Assay.

In vitro phosphorylation assays were carried out as previously described (McGlynn et al., 1992; Weber et al., 1984) with the following modifications. The complete reaction mixture contained 10 ng of the ssD-sequence affinity column-purified dephosphorylated ssD-BP from 293 cells, 20 mM HEPES, 4 mM MgCl$_2$, 10 mM MnCl$_2$, 50 mM NaOV, 200 mM ATP, and 0.8 U EGF-R PTK (CalBiochem) with appropriate controls. The reaction mixtures were incubated at 30° C. for 1 h, and used in EMSA with the radiolabeled D(−) probe as described above.

In Vitro DNA Replication Assay.

The appropriate AAV DNA substrate containing the 3' hairpin structure were prepared and labeled with [g-$^{32}$P] ATP (3,000 Ci/mmol) by using T4 polynucleotides kinase as described previously (Wang et al., 1997). The labeled substrate was boiled, quickly chilled, and used in DNA replication assay in the presence of all four unlabeled dNTPs and the Klenow fragment of E. coli DNA polymerase I. Twenty ng of either the phosphorylated or the dephosphorylated form of the ssD-sequence affinity column-purified ssD-BP was added to the reaction mixture and incubated for 15 min at 25° C. prior to adding the Klenow enzyme to examine the effect of the ssD-BP on AAV DNA replication (second-strand DNA synthesis). The reaction mixtures were electrophoresed on 6% polyacrylamide gels. Gels were dried in vacuuo and autoradiographed at −70° C.

EXAMPLE 2

Figure 1B:
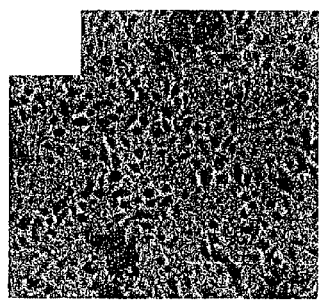
Figure 1C:
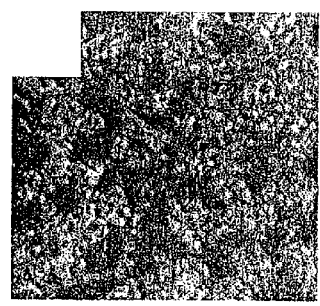
Figure 2:
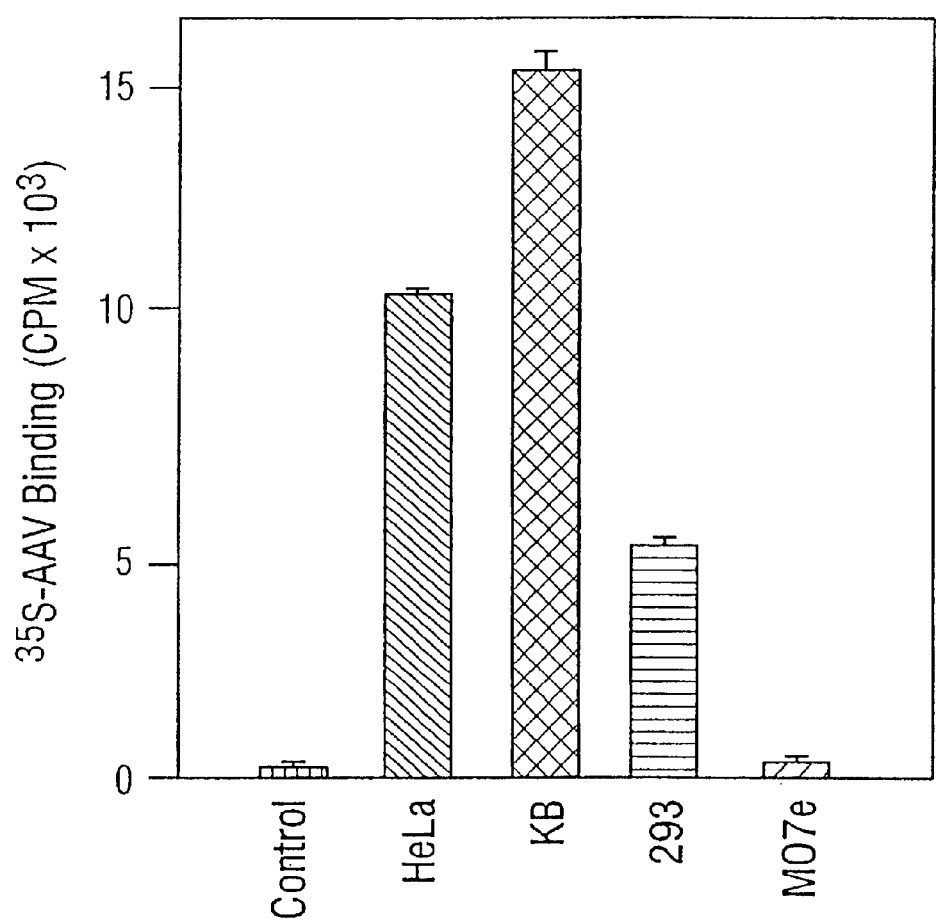
FIG. 2. Analysis of binding of AAV to HeLa, KB, and 293 cells. Equivalent numbers of cells from each cell line, along with a negative (M07e) control, were analyzed in virus-binding assays using $^{35}$S-radiolabeled AAV as described in Example 1.

Dephosphorylation of the D-BP Correlates with the Efficiency of AAV-mediated Transduction in Established and Primary Cells In Vitro In order to investigate the efficiency of AAV-mediated transduction in different cell types, vCMVp-lacZ was used, at an moi of 20, to infect approximately equivalent numbers of human cells from HeLa, KB, and 293 cell lines under identical conditions. Forty-eight h p.i., the numbers of blue cells were enumerated by X-gal staining as described in Example 1. These results are depicted in FIG. 1. It was determined that whereas the recombinant AAV transduction efficiency of HeLa cells was approximately 2% (FIG. 1A), and approximately 11% in KB cells (FIG. 1B), the transduction efficiency was significantly higher, approximately 52%, in 293 cells (FIG. 1C). Although all three cell lines are permissive for AAV infection, it remained possible that the observed differences were due to differential susceptibility of these cells to the virus, presumably because the numbers of the putative membrane receptors for AAV in 293 cells far outnumber those in HeLa and KB cells. This possibility was ruled out by performing virus-binding assays as follows. 35S-labeled AAV particles were used in binding assays with intact HeLa, KB, and 293 cells as described in Example 1. M07e cells, known to be non-permissive for AAV infection (Ponnazhagan et al., 1996), were included in these assays as a negative control. These results are shown in FIG. 2. It is evident that radiolabeled AAV-binding to KB cells was the highest followed by that to HeLa cells. Binding to 293 cells, on the other hand, was the least efficient. No binding to M07e cells occurred, as expected (Ponnazhagan et al., 1997b). Virus-binding was specific, since a 30-fold excess of unlabeled AAV could significantly compete for binding with the radiolabeled virus. Thus, differential susceptibility of infection could not account for the observed differences in the AAV transduction efficiency of these cell types. The inventors hypothesized, therefore, that the observed differences in the recombinant AAV transduction efficiency among these cell lines might be due to functional differences in the host cell D-BP (Qing et al., 1997b).

Figure 3:
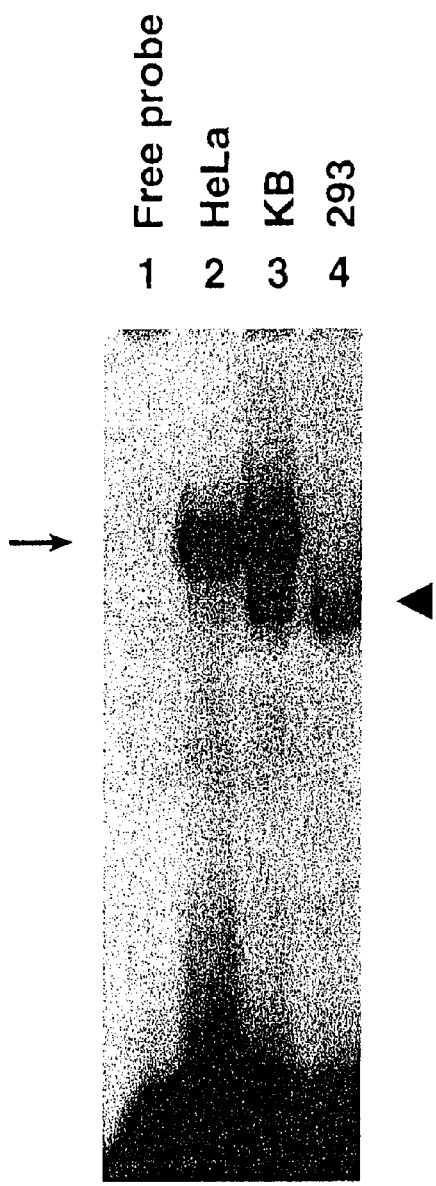
FIG. 3. EMSA with WCE prepared from human HeLa, KB, and 293 cells. Equivalent amounts of WCE prepared from each indicated cell type were used in EMSA with the D(−) probe as described in Example 1. The phosphorylated and the dephosphorylated forms of the D-BP are indicated by the arrow and the arrowhead, respectively.

WCE were prepared from HeLa, KB, and 293 cells under identical conditions and used in EMSA with the D(−) probe, as described previously (Qing et al., 1997b; Wang et al., 1997). These results are shown in FIG. 3. It is interesting to note that whereas KB cells (lane 3) contained roughly the same amounts of both forms of the D-BP (dephosphorylated:phosphorylated ratio, r—1.0), HeLa cells contained predominantly phosphorylated form of the D-BP (lane 2, r—0.3; arrow). 293 cells, on the other hand, contained predominantly dephosphorylated form of the D-BP (lane 4, r—2.4; arrowhead). These data strongly suggest that the extent of AAV-mediated transgene expression correlates with phosphorylation state of the cellular D-BP. In addition, K562 cells, derived from a human erythroleukemia cell line, contained predominantly phosphorylated form of the D-BP (r=0.3, Table 4), and consequently, the efficiency of transgene expression by the same recombinant AAV has previously been shown to be significantly lower in these cells (Ponnazhagan et al., 1996; Srivastava et al., 1996). Thus, it would appear that more dephosphorylated form of the D-BP present in the host cell, higher the efficiency of AAV transduction.

Figures 4A, 4B:
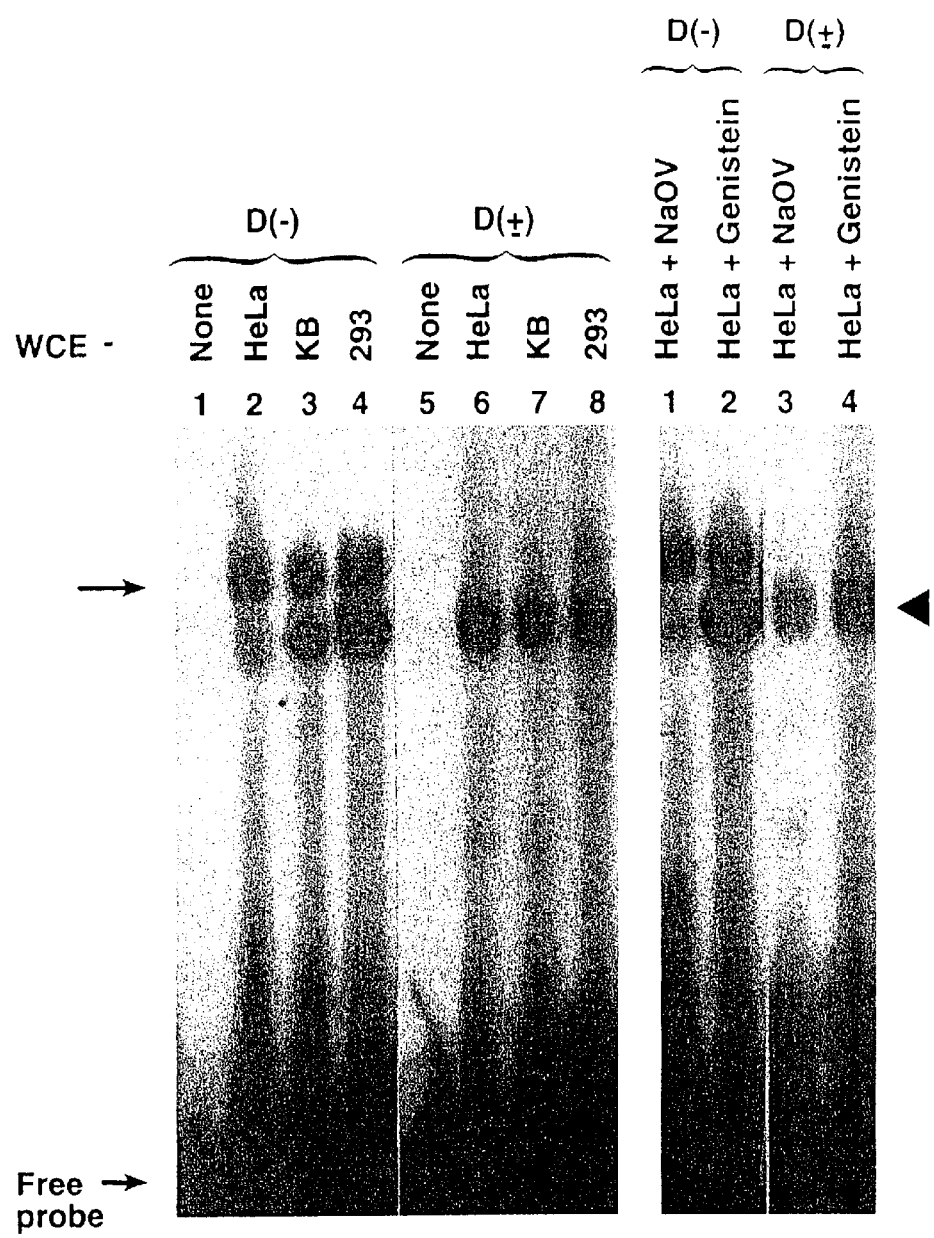
FIG. 4A and FIG. 4B. EMSA with D(−) and D(±) probes, and the effect of treatment of NaOV and genistein on the D-BP.

The inventors further investigated whether the D-BP that interacts with the double-stranded D-sequence [D(±)] probe (Wang et al., 1996) also showed a similar pattern in the three cell types. This was carried out by EMSA with WCE prepared from these cells with D(−) and D(±) probes, respectively, under identical conditions. These results shown in FIG. 4A clearly indicate that whereas roughly the same pattern of distribution of the D-BP was detected in the three cell types, as seen in FIG. 3, when the D(−) probe was used (lanes 2–4), the pattern of the complex formation with the D(+) probe (lanes 6–8) did not appear to be significantly different.

TABLE 4

Comparison of Phosphorylation/Dephosphorylation State of the D-BP in Human and Murine Cells/Tissues

| Cells/Tissues | Ratio of Dephosphorylated:Phosphorylated D-BP[a] |
|---|---|
| Established Cell lines[b]: | |
| 1. HeLa | 0.3 ± 0.1 |
| 2. KB | 1.0 ± 0.2 |
| 3. 293 | 2.4 ± 1.1 |
| 4. K562 | 0.3 ± 0.1 |
| Primary Cells[c]: | |
| 1. Human CD34[+] | 0.1 |
| 2. Mouse Sca-1[+], lin[−] | 8.0 |
| Mouse Tissues[d]: | |
| 1. Brain | 4.0 ± 1.9 |
| 2. Heart | 2.5 ± 1.5 |
| 3. Kidney | 1.4 ± 0.1 |
| 4. Liver | 2.7 ± 1.6 |
| 5. Lung | 2.9 ± 1.4 |
| 6. Muscle | 8.2 ± 1.5 |

[a]These ratios (mean ± standard errors of the means) were derived from densitometric scanning of autoradiograms as described in Example 1.
[b]These data are from three separate studies using three different preparations of WCE.
[c]These data are from one study each due to availability of only limited numbers of these cells.
[d]These data are from three animals each that were sacrificed to obtain these organs but analyzed separately in two independent studies.

Figure 5:
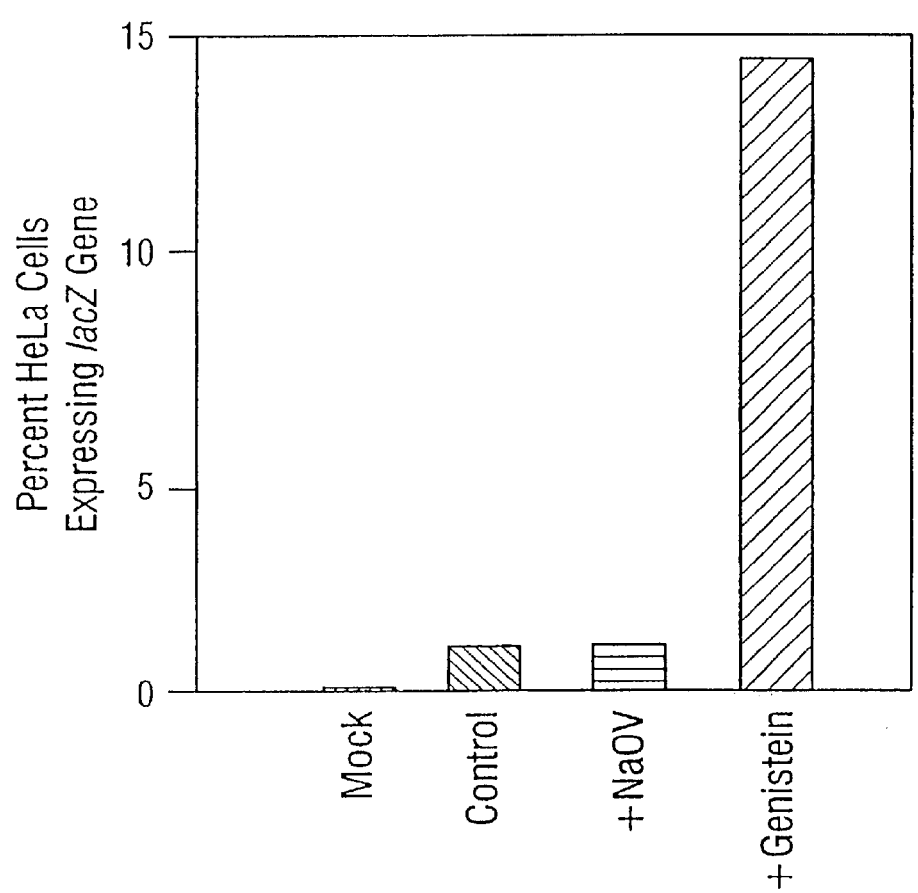
FIG. 5. Transduction efficiency of recombinant vCMVp-lacZ in HeLa cells following treatment with NaOV or genistein. Equivalent numbers of cells were either mock-infected with 4 moi of the recombinant vector following either no treatment (open bar), or treatment with 150 μM genistein for 2 h (closed bar), or 1 mM NaOV for 2 h (stippled bar). Forty eight h post-infection, cells were fixed and the recombinant AAV-mediated transgene expression was detected as described in Example 1.

The inventors also examined whether alteration in the phosphorylation state of the D-BP in HeLa cells correlated with AAV-mediated transgene expression. This was carried out by EMSA with WCE prepared from HeLa cells treated with either genistein, a specific inhibitor of protein tyrosine kinases (Akiyama et al., 1987), or sodium ortho-vanadate (NaOV), a specific inhibitor of protein phosphatases (Qing et al., 1997b). These results shown in FIG. 4B, once again indicate that treatment with genistein (r=1.6), but not with NaOV (r=0.5), resulted in dephosphorylation of the D-BP that interacted with the D(−) probe. Under identical conditions, the D-BP that interacted with the D(±) probe remained unaffected (arrowhead). Interestingly, when replicate HeLa cell cultures that were either mock-treated, or treated with genistein or NaOV, were transduced with vCMVp-lacZ and analyzed for transgene expression 48 h p.i., also indicated that treatment with genistein, but not with NaOV, resulted in a significant increase in the recombinant AAV-mediated transduction efficiency as observed previously (Qing et al., 1997b). These results are shown in FIG. 5. Thus, it is clear that a strong correlation exists between the tyrosine phoshorylation state of the cellular D-BP and the AAV-mediated transduction efficiency.

These analyses were further extended to include human and murine primary hematopoietic stem/progenitor cells. The inventors' recent studies have shown that in CD34[+] cells from approximately 50% of the donors, the efficiency of AAV-mediated transduction ranges between 15–80% (Ponnazhagan et al., 1997b), and when WCE prepared from these cells from one such donor was examined in EMSA with the D(−) probe, predominantly phosphorylated form of the D-BP was detected. In contrast, the inventors have documented a transduction efficiency exceeding 95% of murine Sca-1[+], lin[−] hematopoietic stem/progenitor cells by the same recombinant AAV vector (Ponnazhagan et al., 1997c; 1997d), and consistent with the inventors' hypothesis, when EMSA were carried out under identical conditions, predominantly dephosphorylated form of the D-BP was detected in WCE prepared from these cells. These results are summarized in Table 4 in which the autoradiograms were scanned densitometrically to determine the ratio of dephosphorylated/phosphorylated forms of the D-BP in each cell type. These data indicate that the same or similar D-BPs exist in human and in murine cells, and that once again, the ability of AAV to transduce different cell types strongly correlates with the extent of dephosphorylation of the D-BP that interacts with the D(−) probe.

EXAMPLE 3

Figure 6:
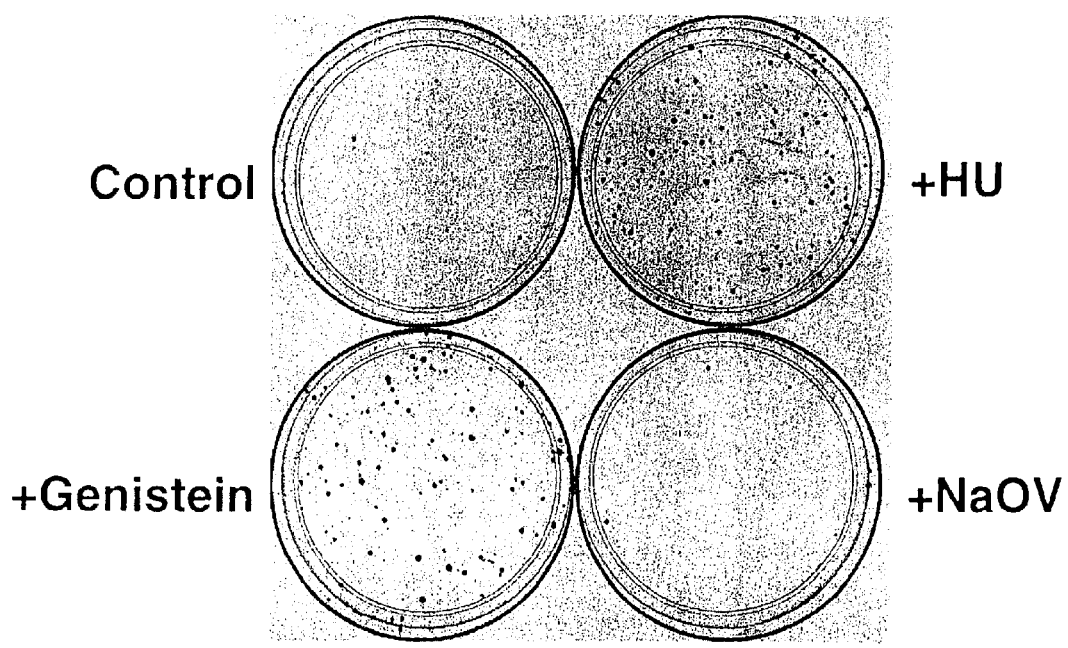
FIG. 6. Transduction efficiency of recombinant vTc-Neo in HeLa cells following treatment with HU, genistein, or NaOV. Equivalent numbers of cells were infected with 20 moi of the recombinant vector following either no treatment, or treatment with the indicated compounds as described in Example 1. Forty eight h post-infection, G418 was added and G418-resistant colonies were enumerated 14 days post-infection following staining with methylene blue as described in Example 1.

Dephosphorylation of the D-BP Also Leads to Increased Stable Integration and Long-term Expression of the AAV-mediated Transgene in Human Cells The inventors explored the possibility whether the efficiency of long-term expression, and stable integration in particular, of AAV-mediated transgene could also be enhanced by dephosphorylation of the D-BP. HeLa cells were treated with genistein as previously described (Qing et al., 1997b), and infected with a recombinant AAV vector containing a gene for resistance to neomycin (vTc-Neo) at an moi of 20. Mock-treated cells, or cells treated with hydroxyurea (HU) known to increase AAV transduction efficiency (Ferrari et al., 1996; Qing et al., 1997b; Russell et al., 1995), or treated with NaOV, were used as appropriate controls. Each treatment was carried out in duplicate. Forty-eight h p.i., cells were exposed to the drug G418, a structural analogue of neomycin, at a final active concentration of 400 μg/ml, and G418-resistant colonies were enumerated 14 days p.i., as described in Example 1. These results are shown in FIG. 6. The numbers of G418-resistant colonies in duplicate from each treatment were as follows: mock-treatment, 7/6; NaOV-treatment, 9/8; genistein-treatment, 96/91; and HU-treatment, 84/90. It is evident that treatment with HU or genistein increased the efficiency of stable transduction by the recombinant AAV to nearly the same extent as that during transient transduction (Qing et al., 1997b).

Figure 7A:
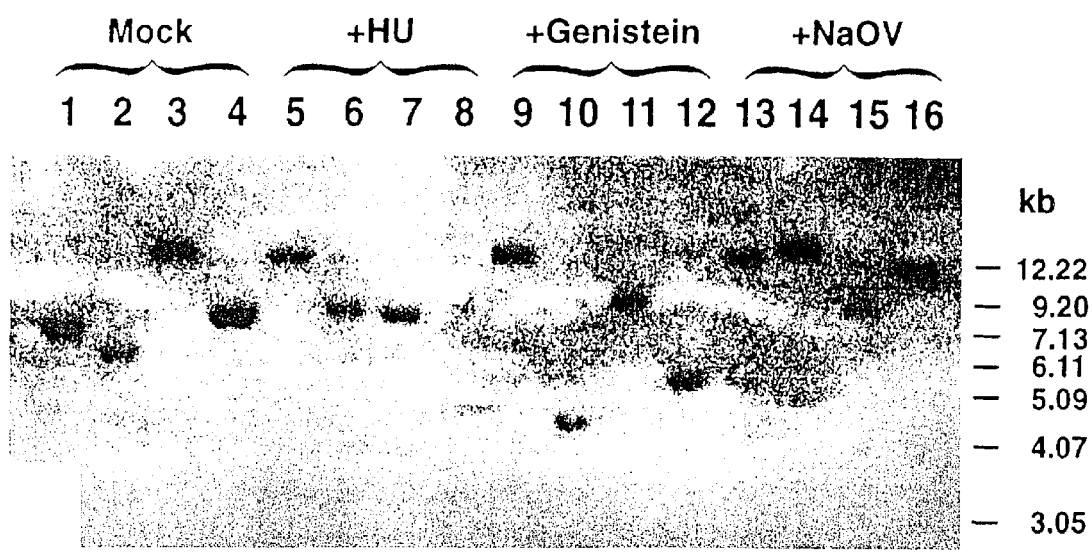
FIG. 7A and FIG. 7B. Southern blot analysis of integration of the recombinant proviral genomes in clonal isolates of HeLa cells. Total genomic DNA samples isolated from four individual clones each treated with the indicated compounds were digested with XbaI (FIG. 7A) or BamHI (FIG. 7B) and analyzed on Southern blots using a neo-specific DNA probe as described in Example 1.
Figure 7B:
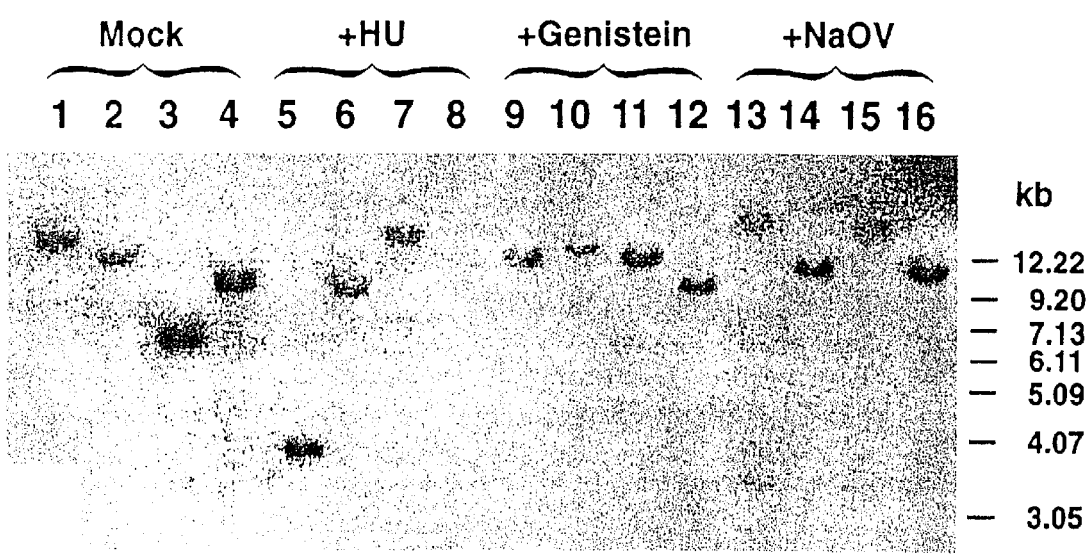
Figure 8A:
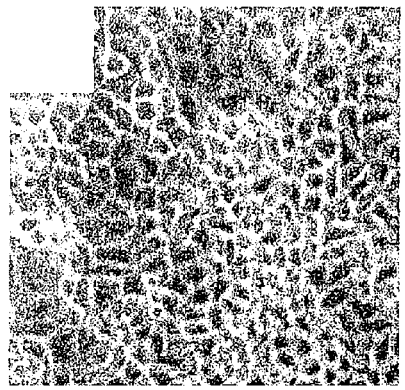
FIG. 8A–FIG. 8D. Comparative analyses of transduction efficiency of vCMVp-lacZ in HeLa cells expressing the AdE4orf6 protein. Approximately equivalent numbers of cells were either mock-infected (FIG. 8A), or infected with 4 moi of vCMVp-lacZ (FIG. 8B), following transfection with plasmid pAdE4orf6 (FIG. 8C), or plasmid pKY-4 (FIG. 8D) under identical conditions. Forty eight h post-infection, cells were fixed, stained with X-gal, and the number of blue cells were enumerated as described in Example 1. Magnification ×100.
Figure 8B:
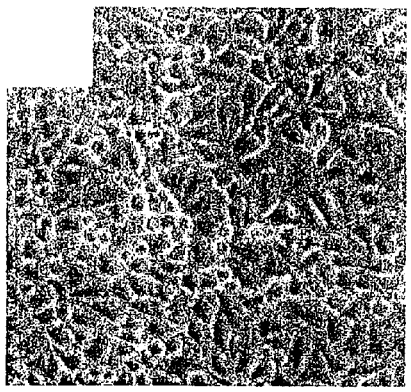
Figure 8C:
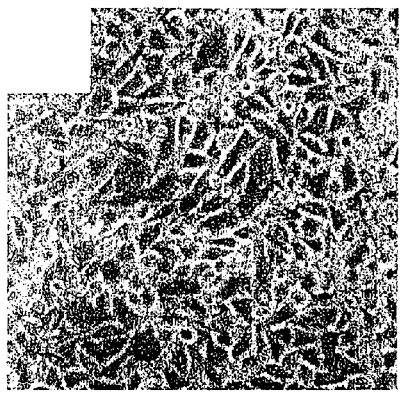
Figure 8D:
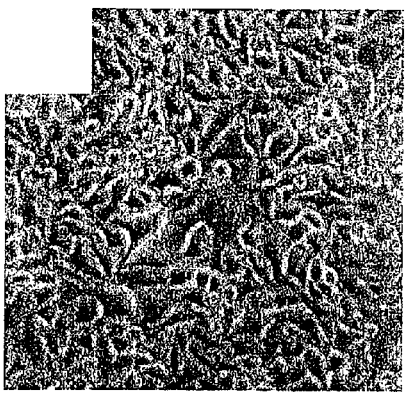

The inventors also examined whether the transduced neo[R] gene was stably integrated into the chromosomal DNA of transduced cells, and whether treatment with HU or genistein altered the integration pattern of the recombinant AAV genome in these cells. Several independently isolated G418-resistant colonies from each treatment group of HeLa cells were amplified separately for 3–4 weeks. Total genomic DNA was isolated from each of the clones, and equivalent amounts were digested with XbaI (no site in the proviral genome) or BamHI (one site in the proviral genome) followed analyses on Southern blots using a $^{32}$P-labeled neo-specific DNA probe as described in Example 1. The results for 4 individual clones of each of the treatment groups are presented in FIG. 7. It is evident that the recombinant AAV genome was stably integrated into the host chromosomal DNA in all clones, and that the integration pattern of the proviral DNA was distinct in each of the clones examined. Using polymerase chain reaction (PCRTM) assays with the neo- and chromosome 19-specific primer-pair (Ponnazhagan et al., 1997a; Qing et al., 1997a; Samulski et al., 1991), the inventors did not observe proviral genomic integration at the chromosome 19 target site previously characterized for the wt AAV genome (Kotin et al., 1991; 1990; Samulski et al., 1991). These results are consistent with previously published reports by the inventors (Ponnazhagan et al., 1997a; Qing et al., 1997a) and others (Kearns et al., 1996) that unlike the wt AAV genome, recombinant AAV genomes integrate randomly in human cells.

EXAMPLE 4

A Deletion Mutation in the AdE4orf6 Gene Fails to Augment AAV-mediated Transgene Expression as Well as Facilitate Dephosphorylation of the D-BP Recent studies from two independent laboratories have documented that the AdE4orf6 gene product catalyzes the synthesis of the AAV second strand DNA leading to significant enhancement in AAV transduction efficiency (Ferrari et al., 1996; Fisher et al., 1996). In order to firmly establish the correlation between AdE4orf6-mediated enhancement of transgene expression and dephosphorylation of the D-BP, the following approach was taken. The inventors have demonstrated that expression of the AdE4orf6 gene product is necessary and sufficient to lead to dephosphorylation of the D-BP in HeLa cells (Qing et al., 1997b). The inventors hypothesized that a deletion mutation in this gene would fail to augment not only AAV-mediated transgene expression, but also to catalyze dephosphorylation of the D-BP. To this end, HeLa cells were either mock-transfected, or transfected with plasmids pAdE4orf6 (containing the gene for the AdE4orf6 protein), or pKY-4 (containing a deletion mutation in the AdE4orf6 gene), and 48 h post-transfection, were either mock-infected or infected with vCMVp-lacZ at an moi of 4 under identical conditions. The number of blue cells were enumerated using X-gal 48 h post-infection as described in Example 1. These results are depicted in FIG. 8. It is evident that whereas the recombinant AAV transduction efficiency in HeLa cells increased to approximately 18% (FIG. 8C) following transfection with pAdE4orf6, compared with 2% in mock-transfected cells (FIG. 8B), the transduction efficiency following transfection with pKY-4 was only 3% (FIG. 8D), nearly the same as that of mock-transfected HeLa cells. These results corroborate that expression of the AdE4orf6 protein, known to facilitate the second-strand viral DNA synthesis in AAV-infected cells, increases AAV-mediated transgene expression, and that a deletion mutation in the AdE4orf6 gene abolishes this function.

Figure 9:
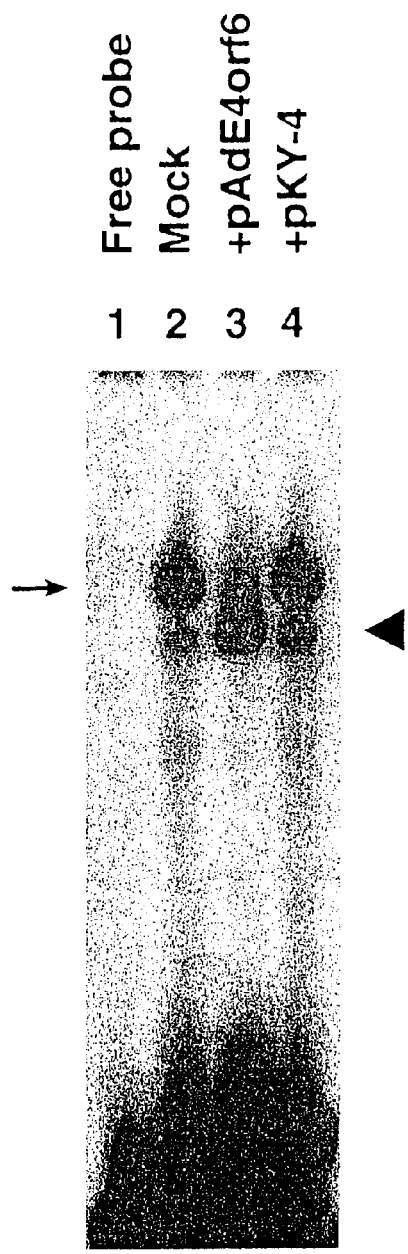
FIG. 9. EMSA with WCE prepared from HeLa cells expressing the AdE4orf6 protein. Equivalent amounts of WCE prepared from mock-transfected (lane 2), or transfected with plasmid pAdE4orf6 (lane 3), or plasmid pKY-4 (lane 4) were used in EMSA with the D(−) probe as described in Example 1. The phosphorylated and the dephosphorylated forms of the D-BP are indicated by the arrow and the arrowhead, respectively.

The inventors next examined whether this deletion mutation in the AdE4orf6 gene also abrogated the ability of this gene product, either directly or indirectly, to dephosphorylate the D-BP. WCE prepared from replicate cultures of HeLa cells that were either mock-transfected, or transfected with plasmids pAdE4orf6, or pKY-4, respectively, as described above, were used in EMSA with the D(−) probe. These results of are presented in FIG. 9. As expected, the ratio of dephosphorylated/phosphorylated forms of the D-BP was low in mock-transfected HeLa cells (lane 2, r=0.3; arrow), dephosphorylation of the D-BP correlated well with expression of the AdE4orf6 protein in these cells (lane 3, r=4.6; arrowhead). A deletion mutation in this gene indeed failed to catalyze dephosphorylation of the D-BP (lane 4, r=0.5; arrow). Taken together, these data establish a strong correlation between AAV-mediated transgene expression and the phosphorylation state of the cellular D-BP in vitro.

EXAMPLE 5

The Efficiency of Transduction by Recombinant AAV Correlates with the Extent of Dephosphorylated State of the D-BP in Murine Tissues In Vivo The correlation between AAV transduction efficiency and phosphorylation state of the cellular D-BP in intact organs/tissues in vivo was also examined. This is of particular interest since a number of investigators have identified specific organs or tissues, such as muscle (Kessler et al., 1996; Xiao et al., 1996), brain (Kaplitt et al., 1994; McCown et al., 1996), liver (Koeberl et al., 1997; Ponnazhagan et al., 1997c), lung (Carter and Flotte, 1996; Flotte et al., 1993), and heart (Kaplitt et al., 1996; Ping et al., 1996), to exhibit high-efficiency transduction by recombinant AAV vectors, although the precise mechanism underlying this phenomenon remains unknown. Since the D-BPs detected in WCE prepared from murine Sca-1$^+$, lin$^−$ hematopoietic cells appeared to be indistinguishable from those detected in WCE prepared from human cells, the inventors systematically analyzed various murine organs or tissues obtained from three animals each, prepared protein extracts and used in EMSA with the D(−) probe under identical conditions to those described for human and murine cells. The ratio of dephosphorylated/phosphorylated forms of the D-BP for each of the organs/tissues from EMSA autoradiograms was determined by densitometric scanning. These results are summarized in Table 4. As compared with EMSA carried out with WCE prepared from either human or murine cells, D-BPs, either in phosphorylated form, or in dephosphorylated form, or both, could be readily detected in most of murine organs or tissues analyzed. Interestingly, however, the most striking observation was that the ratio of dephosphorylated/phosphorylated D-BP was highest in murine skeletal muscle tissues followed by that in brain, lung, liver, and heart; and these organs/tissues have been shown, roughly in that order, to allow high-efficiency AAV-mediated transduction in vivo. Kidney also showed a higher ratio, indicating these tissues contain predominantly dephosphorylated form of the D-BP, and, therefore, would be expected to exhibit a reasonably high efficiency of AAV-mediated transduction. Other organs, such as spleen and thymus, contained more of phosphorylated form of the D-BP, and thus far, it has been difficult to document AAV-mediated transgene expression in these tissues (Ponnazhagan et al., 1997c; Ponnazhagan et al., 1997d). Thus, these results establish a strong correlation between AAV transduction efficiency and dephosphorylated state of the cellular D-BP in vivo as well.

EXAMPLE 6

Figure 10:
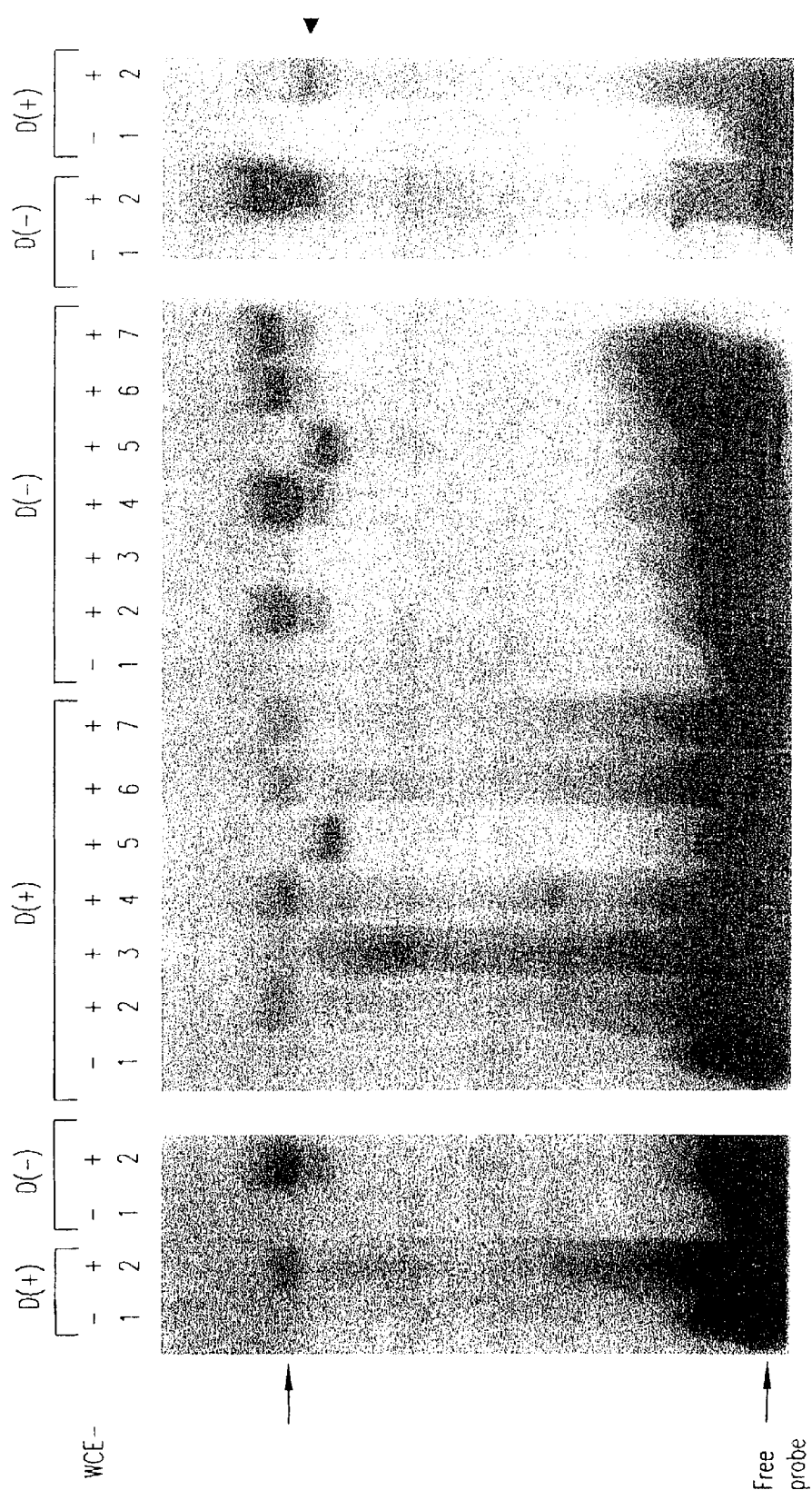
FIG. 10A, FIG. 10B and FIG. 10C. Differential interaction of the D-BP with the D(−) and D(+) sequences in the AAV-ITRs. Electrophoretic mobility-shift assays (EMSA) were carried out with D(−) or D(+) 20 nucleotide synthetic oligonucleotides (FIG. 10A) as previously described (Wang et al., 1997). Various indicated unlabeled single- or double-stranded oligonucleotides representing the D-sequence, a non-AAV substitute (S)-sequence, and AAV capsid (cap) gene sequences were used in competition studies (FIG. 10B). Comparative analysis of D-BP interaction with the single-stranded D(−) sequence versus the double-stranded D±sequence (FIG. 10C). The arrow indicates the single-stranded D-BP, and the arrowhead indicates the double-stranded D-BP.

The D-BP Interacts Specifically and Preferentially with the Single-stranded D-sequence in the AAV-ITR at the 3'-end of the Viral Genome WCE were prepared from HeLa cells and EMSA were carried out with each of the two single-stranded D-sequence synthetic oligonucleotides, D(+) and D(−), respectively, under identical conditions (Wang et al., 1997). These results are shown in FIG. 10. The D(−) sequence was at least three-fold more efficient in forming a complex (arrow) with the D-BP compared with the D(+) sequence (FIG. 10A, lanes 2) as determined by densitometric scanning of autoradiographs. Each of the complex formation was specific since the binding could be competed with the respective unlabeled oligonucleotides (FIG. 10B, lanes 3). The binding could not be competed with the double-stranded [D(±)] sequence, or with a non-AAV, substitute S(−) sequence, or with an AAV-cap sequence (FIG. 10B, lanes 4, 6 and 7). In cross-competition studies, both D(−) and D(+) oligonucleotides yielded a DNA-protein complex which migrated faster (FIG. 10B, lanes 5) suggesting that either the same D-BP interacted differently with single-stranded and with double-stranded D-sequences, or that two different D-BPs interacted with single-stranded versus double-stranded D-sequences, respectively. This was further confirmed by carrying out EMSA with D(−) and D(±) oligonucleotides under identical conditions (FIG. 10C). Again, the D-BP interacting with double-stranded D-sequence migrated faster than that with single-stranded D-sequence (arrowhead).

EXAMPLE 7

Figure 11:
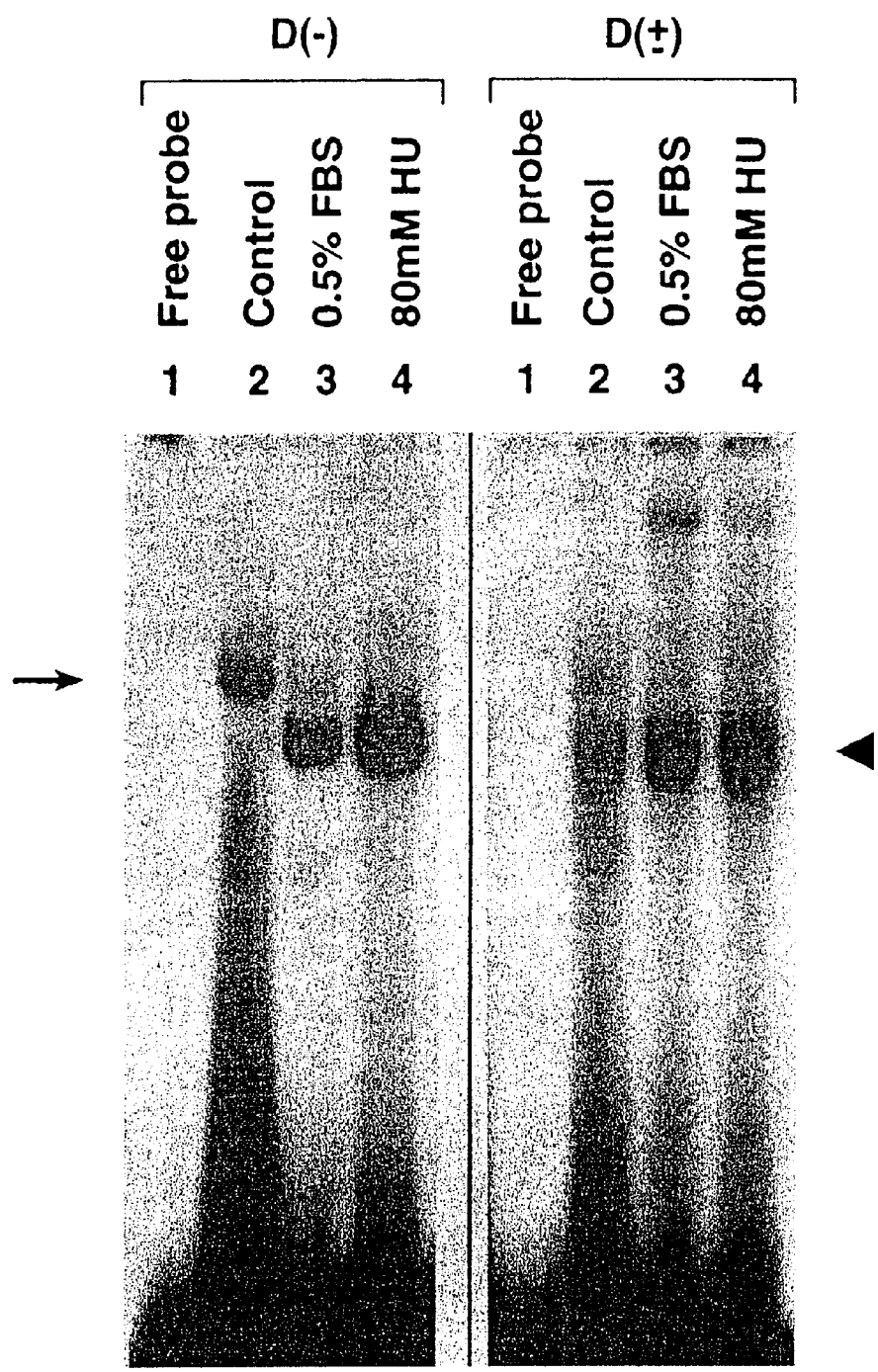
FIG. 11. The D-BP undergoes modification following growth-arrest of HeLa cells. EMSA were carried out with WCE prepared under different conditions as described in the text. D(−) or D± probes were used under identical conditions as described in the legend to FIG. 10.

The D-BP that Binds to Single-stranded D-sequence is Phosphorylated, and Undergoes Dephosphorylation During Cell Cycle In an attempt to distinguish between the two possibilities that two different D-BPs were involved or that the same D-BP, depending upon some unknown modification(s), was involved in interacting with the single- versus the double-stranded D-sequences, WCE prepared from HeLa cells that were maintained either in 10% FBS or in 0.5% FBS for 14 days. WCE were also prepared from HeLa cells treated with 80 mM hydroxyurea (HU) for 24 h since HU-treatment has been shown to enhance AAV transduction efficiency (Ferrari et al., 1996; Russell et al., 1995). The results of EMSA carried out under these conditions are shown in FIG. 11. Once again, the D(−) probe detected the same D-BP in WCE prepared from untreated cells as before (arrow). It is interesting to note, however, that under identical conditions, the same D(−) sequence interacted with the D-BP in WCE prepared from growth-inhibited cells that migrated faster, which appeared to be indistinguishable from that which interacted with the D(±) probe (arrowhead). These results suggest that the same D-BP that binds to single-stranded D-sequence undergoes some type of modification (subsequently determined to be phosphorylation at tyrosine residues) during cell cycle, and there appear to be two forms of D-BP, one interacts with the single-stranded and the other interacts with the double-stranded D-sequences, respectively.

Because HU-treatment has been shown to enhance AAV transduction efficiency (Ferrari et al., 1996; Russell et al., 1995), it was of interest to investigate whether co-infection with Ad2, or expression of the AdE4orf6 protein, recently shown to be necessary and sufficient to catalyze the second strand synthesis (Ferrari et al., 1996), also correlated with this modification. The inventors hypothesized that among other possible post-translational modifications, the D-BP from HeLa cells grown in 10% FBS that interacted with the D(−) probe was a phosphorylated protein, and that various treatments led to dephosphorylation of the D-BP. This hypothesis was experimentally tested, as will be described later.

Figure 12A:
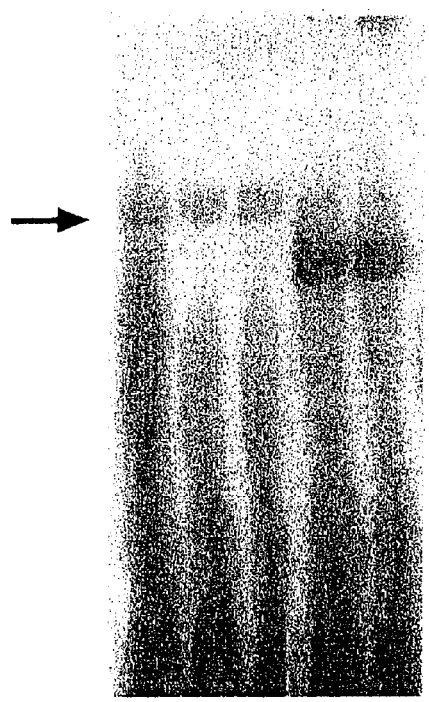
FIG. 12A and FIG. 12B. Ad2 infection or the AdE4orf6 protein expression leads to the D-BP modification. Cells were either mock-infected, or infected with the wt AAV, Ad2, or co-infected with AAV+Ad2 at the indicated moi, and WCE prepared from these cells were used in EMSA with the D(−) probe (FIG. 12A). EMSA were also carried out with WCE prepared from cells transfected with the indicated plasmids (FIG. 12B).
Figure 12B:
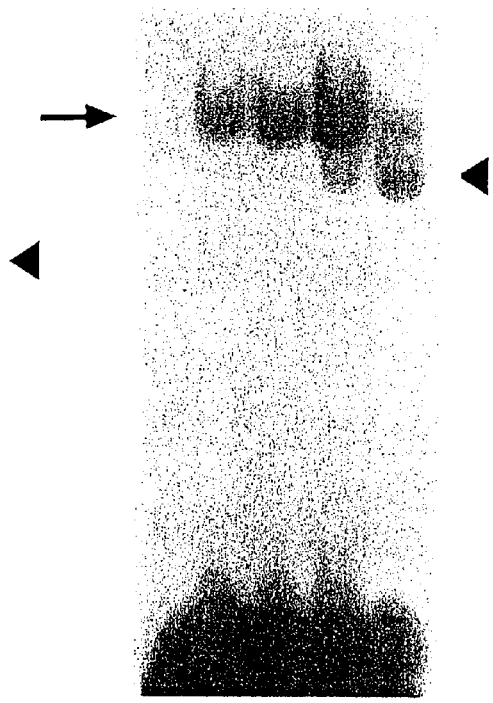

WCE were prepared from mock-infected, AAV-infected, Ad2-infected, or 5 AAV+Ad2 co-infected HeLa cells, as well as from cells that were mock-transfected, or transfected with plasmids pWP-7A (containing the $Tc^R$ gene), pWP-19 (containing the $neo^R$ gene), or pCMV-AdE4orf6 (containing the AdE4orf6 gene), respectively. The results of EMSA carried out with these WCE and the D(−) probe are shown in FIG. 12. It is noteworthy that the D(−) sequence formed a complex with a phosphorylated form of the 10 D-BP (FIG. 12A, arrow), and infection with AAV alone, at an moi of 1 or 10, had no effect. The same probe formed another complex with the D-BP that was dephosphorylated in Ad2-infected or AAV+Ad2 co-infected cells (arrowhead). Remarkably, the AdE4orf6 protein alone, known to facilitate the second-strand DNA synthesis, was also sufficient to dephosphorylate the D-BP (FIG. 12B).

Figure 13:
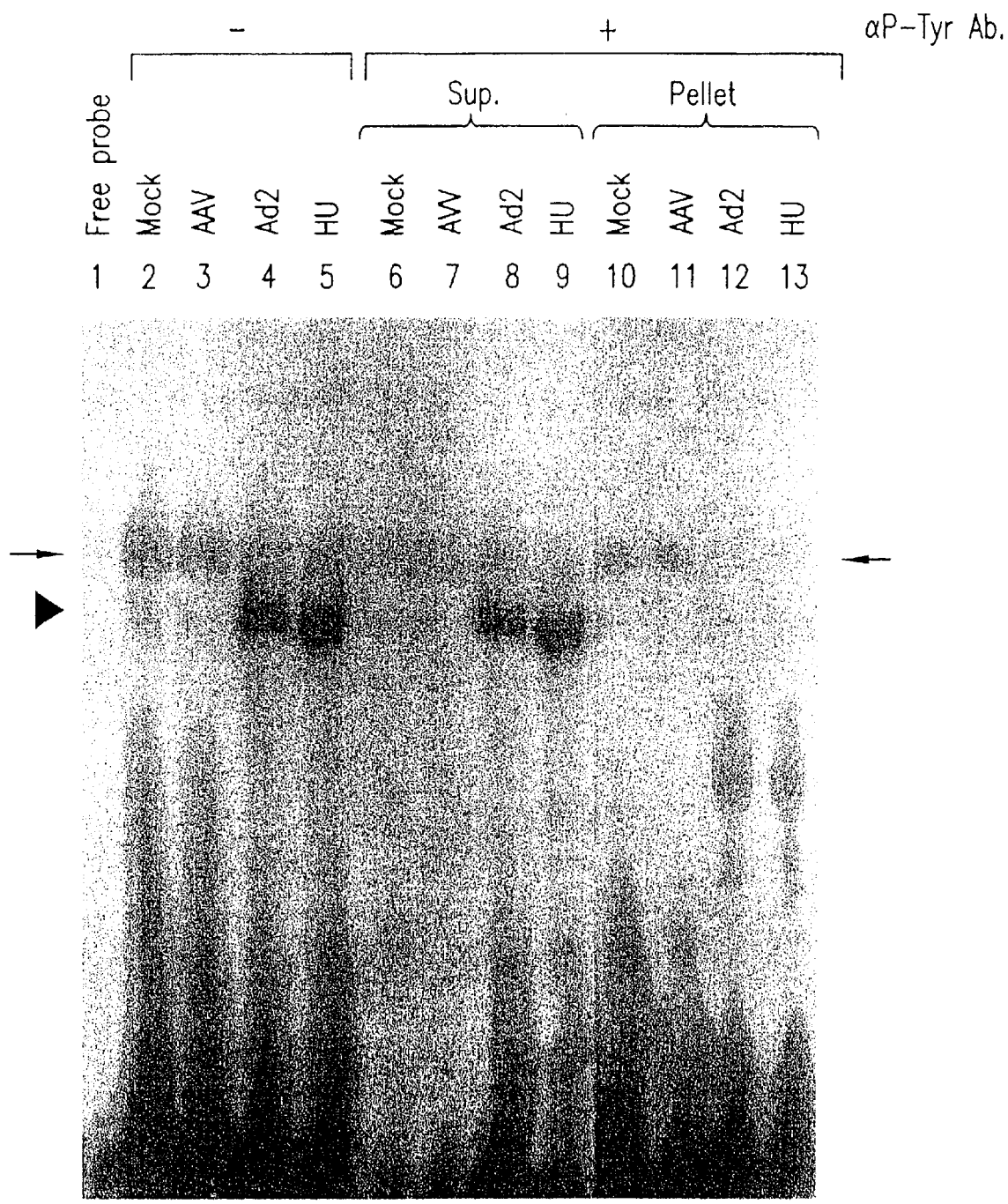
FIG. 13. The D-BP is phosphorylated at tyrosine residues. The D-BP was immunoprecipitated from equivalent amounts of WCE prepared from cells following mock-infection, or infection with AAV, or with Ad2, or treatment with HU, with the anti-phosphotyrosine antibody (αP-Tyr Ab), followed by precipitation with protein A agarose beads as previously described (Piwnica-Worms, 1987; Tokiwa et al., 1996; Kumagai and Dunphy, 1996; Dudek et al., 1996). Supernatants were collected, and immuno-precipitates were washed with PBS and dissolved in EMSA reaction buffer. Ten μl of each of the supernatants (Sup.) and resuspended pellet solution (Pellet) were used for EMSA with the D(−) oligonucleotide probe.
Figure 14A:
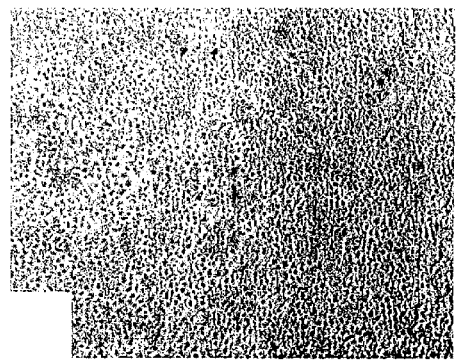
FIG. 14A–FIG. 14D. Inhibition of protein tyrosine kinases leads to increased transduction efficiency of recombinant AAV. HeLa cells were infected with 20 moi of vCMVp-lacZ following either no treatment (FIG. 14A), or treatment with 10 mM HU for 24 h (FIG. 14B), 150 μM genistein for 2 h (FIG. 14C), or 1 mM NaOV for 2 h (FIG. 14D). Forty eight h post-infection, cells were fixed and the recombinant AAV-mediated transgene expression was detected as previously described (Ponnazhagan et al., 1996; 1997a).
Figure 14B:
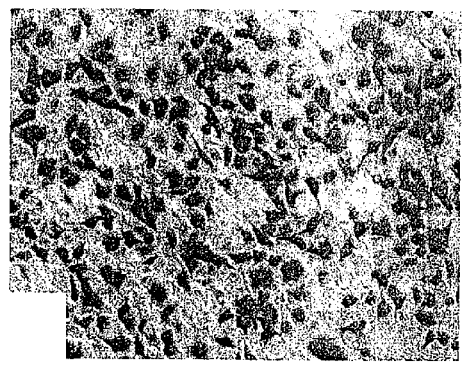
Figure 14C:
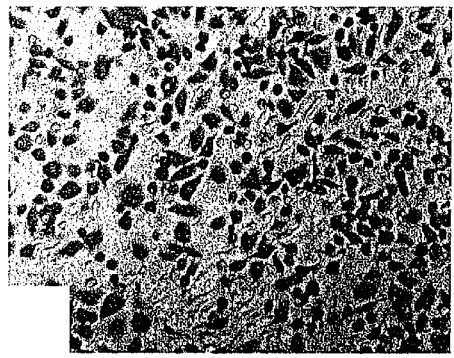
Figure 14D:
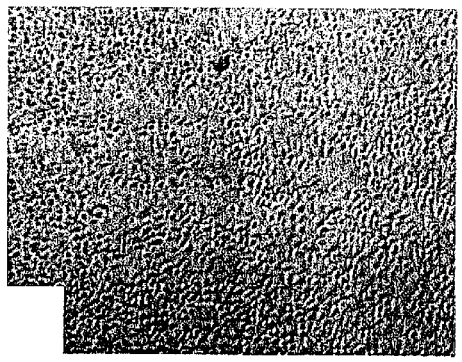

Using the anti-phosphotyrosine antibody, the inventors have determined that the slow-migrating D-BP is indeed the phosphorylated protein which specifically interacts with the D(−) sequence, whereas the faster-migrating D-BP is de-phosphorylated. These data are shown in FIG. 13. It is interesting to note that the complexes formed with WCE prepared from mock-infected, or AAV-infected cells (left arrow), but not from Ad-infected, or HU-treated cells (arrowhead), could be immuno-precipitated with the anti-phosphotyrosine antibody. The phosphorylated D-BP could also be recovered from the immuno-precipitate and shown to interact with the D(−) sequence (right arrow).

EXAMPLE 8

Inhibition of Phosphorylation of the D-BP Leads to Enhancement in the Transduction Efficiency of Recombinant AAV, and Autonomous Replication of the wt AAV Genome The inventors next explored the possibility whether AAV transduction efficiency could be enhanced by simply inhibiting tyrosine phosphorylation of the D-BP. HeLa cells were treated for 2 h with 150 μM genistein, a specific inhibitor of protein tyrosine kinases (Akiyama et al., 1987), and infected with a recombinant AAV vector containing the cytomegalovirus (CMV) promoter-driven lacZ gene (vCMVp-lacZ) at an moi of 20, and the number of blue cells were enumerated using X-Gal 48 h post-infection as previously described (Ponnazhagan et al., 1996; 1997). Mock-treated cells, or cells treated with HU, or treated with NaOV, a known protein phosphatase inhibitor (Kumagai and Dunphy, 1996; Dudek et al., 1996), were used as appropriate controls. These results are shown in FIG. 14. It is evident that whereas AAV transduction efficiency of HeLa cells following mock-treatment or treatment with NaOV was approximately 3%, the transduction efficiency increased to approximately 60% following treatment of HeLa cells with HU or genistein.

Figure 15:
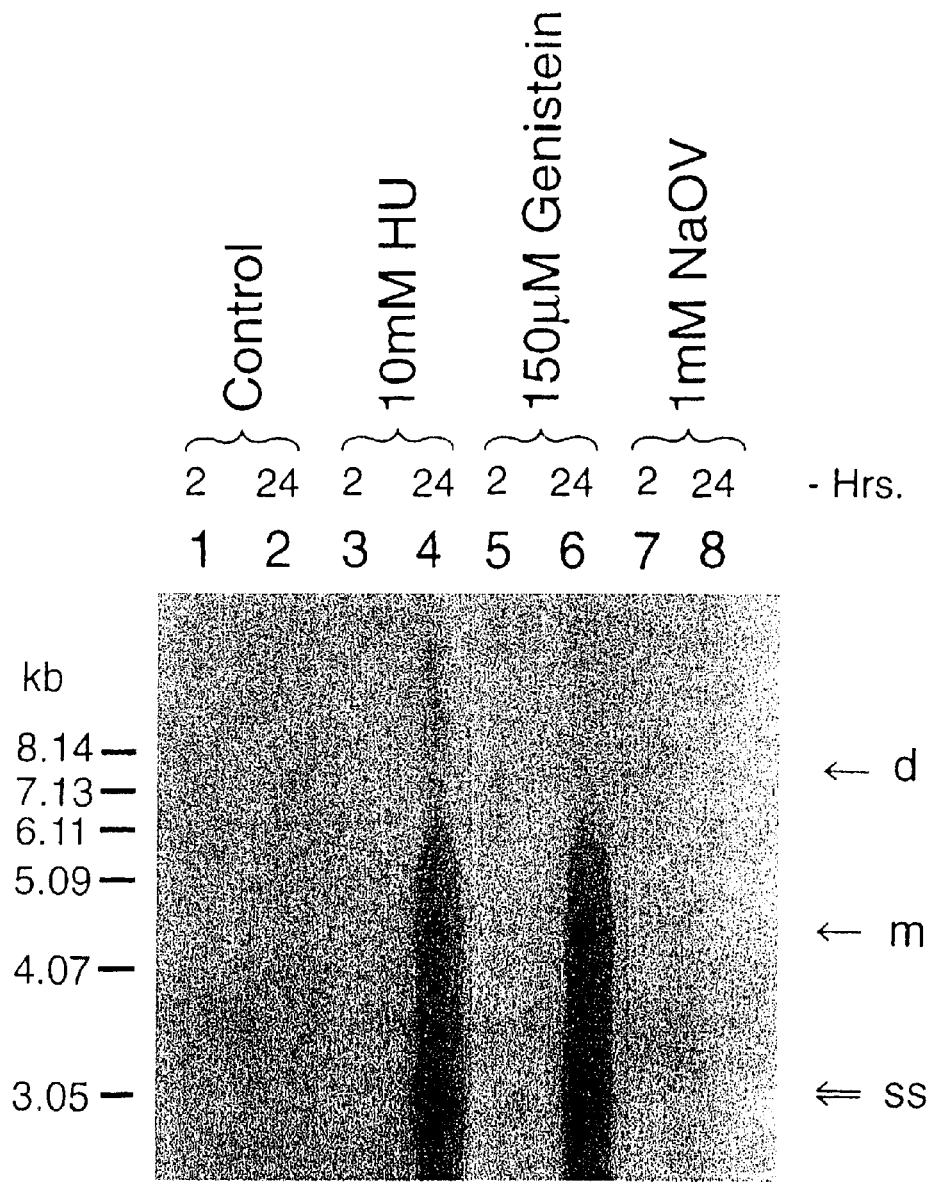
FIG. 15. Inhibition of cellular protein tyrosine kinases leads to autonomous replication of the wt AAV genome. Cells were infected with the wt AAV at an moi of 2 following either no treatment, or treatment with HU, genistein, or NaOV, and low $M_r$ DNA samples isolated at various indicated times post-infection were analyzed on Southern blots using an AAV-specific DNA probe. d, m, and ss denote the dimeric and monomeric replicative DNA intermediates and single-stranded progeny AAV genomes, respectively.
Figure 16:
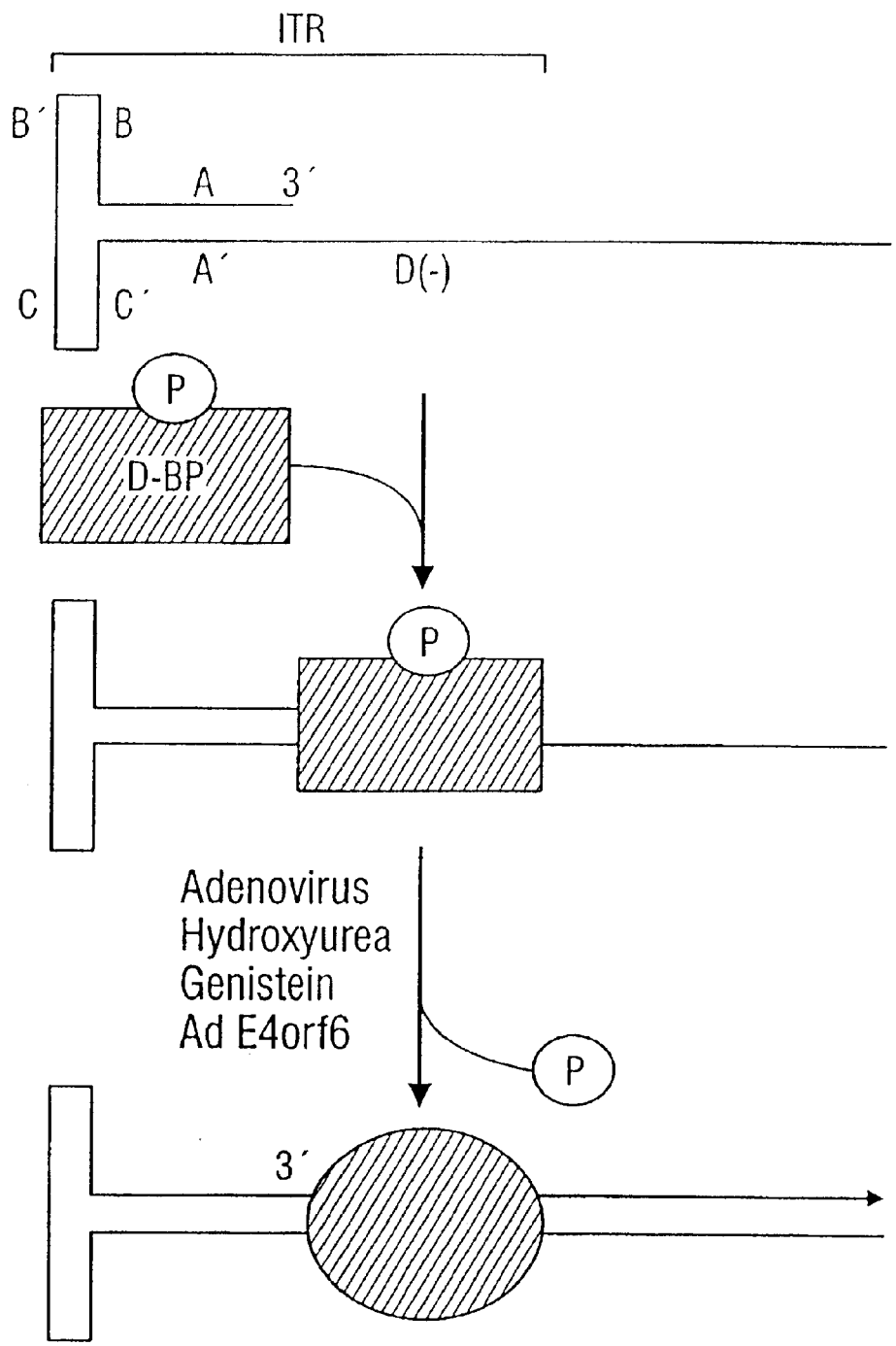
FIG. 16. A model for the role of the tyrosine-phosphorylated D-BP in AAV-mediated transgene expression. The phosphorylated form of D-BP preferentially complexes with the D(−) sequence in the AAV-ITR, and blocks initiation of DNA replication from the 3'-OH end. Various indicated treatments cause dephosphorylation of the D-BP leading to some type of conformational change resulting in accessibility of the 3'-OH end as a primer for the second strand DNA synthesis followed by gene expression.
Figure 17G:
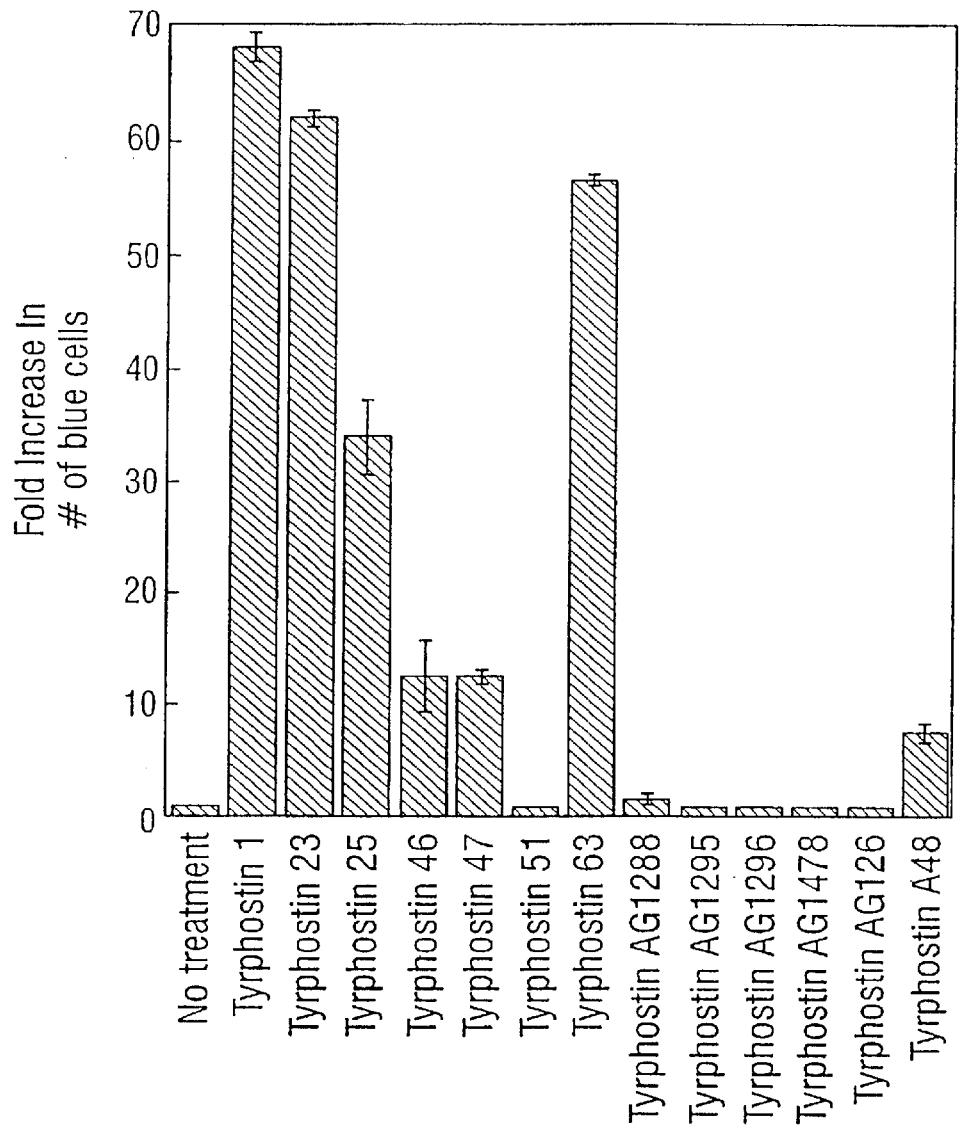

The inventors also wished to examine whether dephosphorylation of the D-BP leads to autonomous replication of the wt AAV genome. HeLa cells were either mock-treated, or treated with HU, genistein, or NaOV as described in the Example 1, and infected with 2 moi of wt AAV. Low $M_r$ DNA samples were isolated and analyzed on Southern blots using an AAV-specific DNA probe (Wang et al., 1996; 1995). It is evident that the inhibition of protein tyrosine kinases by genistein leads to autonomous replication of the wt AAV genome, the extent of which is comparable to that following treatment with HU (FIG. 15). These results provide strong evidence that the phosphorylation state of the D-BP plays a crucial role in the life cycle of AAV.

EXAMPLE 9

Inhibitors of EGF-R PTK Increase the Transduction Efficiency of Recombinant AAV

In the studies detailed above, the inventors showed that inhibition of tyrosine phosphorylation of the ssD-BP by genistein, a specific inhibitor for all protein tyrosine kinases (Akiyama et al., 1987; Barnes and Peterson, 1995; Carlo-Stella et al., 1996; Constantinou and Huberman, 1995), increased transduction efficiency by recombinant AAV (Qing et al., 1997b).

To investigate which kinase may be responsible for tyrosine phosphorylation of the ssD-BP, the effects of various kinase inhibitors on the transduction efficiency of recombinant AAV were studied. HeLa cells were treated with 100 nM–1 mM herbimycin A (Fukazawa et al., 1991), 100 nM–1 mM staurosporine (Couldwell et al., 1994), 50–200 mM LY294002 (Vlahos et al., 1994), 500 nM–10 mM wortmannin (Okada et al., 1994), 1–500 mM apigenin (Kuo and Yang, 1995), 1–200 mM tyrphostin A48 (Gazit et al., 1989), and 150 mM genistein for 2 h at 37° C. Following treatment, cells were infected with vCMVp-lacZ at an MOI of 2. Cells were then stained with X-gal 48 h p.i. The results are summarized in Table 5. It is evident that, in addition to genistein, treatment with tyrphostin A48, a specific inhibitor for EGF-R PTK, caused an increase in the numbers of blue cells. These results suggest that EGF-R PTK is involved in recombinant AAV-mediated transgene expression.

TABLE 5

Effect of cellular protein kinase inhibitors on AAV-mediated transgene expression.

| Inhibitor[a] | Target[b] | Fold-increase in AAV transduction[c] |
|---|---|---|
| 1. Apigenin | MAP kinase | 0 |
| 2. Genistein | Tyrosine kinases, PK-A, PK-C | 5.4 |
| 3. Herbimycin A | pp60[c-src] | 0 |
| 4. LY294002 | PI 3 kinase | 0 |
| 5. Staurosporine | CaM kinase, MLC kinase, PK-A, PK-C PK-G | 0 |
| 6. Tyrphostin A48 | EGF-R tyrosine kinase | 8.1 |
| 7. Wortmannin | MAP kinase, MLC kinase, PI-3 kinase, PI 4-kinase | 0 |

[a]HeLa cells were treated with the indicated compounds at 37°C. for 2 h at concentrations detailed in the text.
[b]Abbreviations: MAP kinase, mitogen-activated protein kinase; PK-A, protein kinase A; PK-C, protein kinase C; PK-G, protein kinase G; PI 3-kinase, phosphatidylinositol 3 kinase; PI 4-kinase, phosphatidylinositol 4 kinase; CaM kinase, calmodulin-dependent protein kinase; MLC kinase; myosin light chain kinase; and EGF-R tyrosine kinase, epidermal growth factor receptor tyrosine kinase.
[c]Equivalent numbers of HeLa cells were either mock-treated or treated with the highest concentration of the indicated compounds separately followed by infection with the vCMVp-lacZ vector at an MOI of 2, and percentage of cells expressing the transgene were determined 48 h p.i. as described in Example 1.

To further investigate the role of EGF-R PTK in recombinant AAV transduction, specific inhibitors for EGF-R PTK, tyrphostin 1, 23, 25, 46, 47, 51, 63, and AG1478 (Gazit et al., 1989; Levitzki, 1990; Levitzki et al., 1991; Lyall et al., 1989; Yaish et al., 1988), in addition to tyrphostin A48, were tested for their effects on recombinant AAV transduction. Specific inhibitors for tumor necrosis factor a (TNF-α) production, AG126; TNF-α cytotoxicity, AG1288 (Novogrodsky et al., 1994); platelet-derived growth factor receptor protein tyrosine kinase (PDGF-R PTK), AG1295 and AG1296 (Kovalenko et al., 1994) were used as controls.

Figure 18:
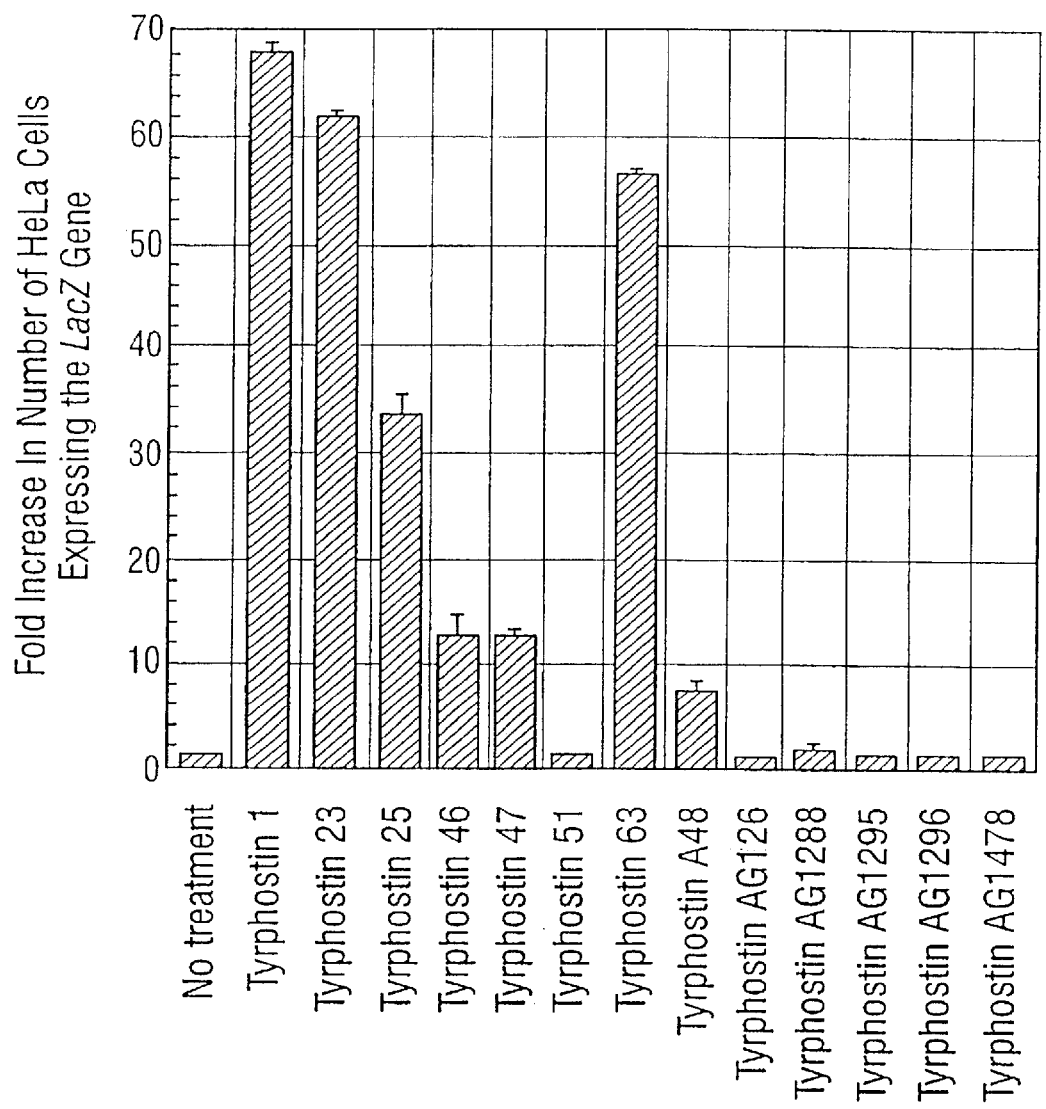
FIG. 18. Comparative analyses of transduction efficiency of vCMVp-lacZ in HeLa cells treated with 500 mM of various tyrphostin. Approximately equivalent numbers of HeLa cells were treated with each of the indicated compounds separately for 2 h and infected with 2 MOI of vCMVp-lacZ under identical conditions. Forty eight h post infection, cells were fixed, stained with X-gal, and the number of blue cells were enumerated as described in Example 1.

HeLa cells were treated for 2 h with 1–800 mM of each tyrphostin followed by infection with vCMVp-lacZ at an MOI of 2, as described above. The results are shown in FIG. 18. These results demonstrate that, among all specific inhibitors tested, treatment with tyrphostin 1 resulted in the greatest increase in recombinant AAV-mediated transgene expression at the optimal concentration (without causing significant cytotoxicity) of 500 mM, followed by tyrphostin 23, 63, 25, 46, and 47. These results again emphasize the role the EGF-R PTK plays in AAV-mediated transgene expression. The varying degrees to which tyrphostin specific for EGF-R PTK affect AAV transduction efficiency may be due to the possible different mechanisms by which each compound inhibits the EGF-R PTK.

It is interesting to note that there also was an increase in recombinant AAV transduction efficiency with as little as 100 mM of tyrphostin 1, even though the $IC_{50}$ of tyrphostin 1 for EGF-R PTK is 1250 mM. In addition, treatment either with tyrphostin I or tyrphostin 23 consistently increased recombinant AAV transduction efficiency in many other cell lines, such as A431, K562, 293, and KB. Tyrphostin AG126 and AG1288, which are specific inhibitors for TNF-α production and TNF-α cytotoxicity, respectively, and tyrphostin AG1295 and AG1296, both of which are specific inhibitors of the PDGF-R PTK, had no effect.

EXAMPLE 9

Figure 19:
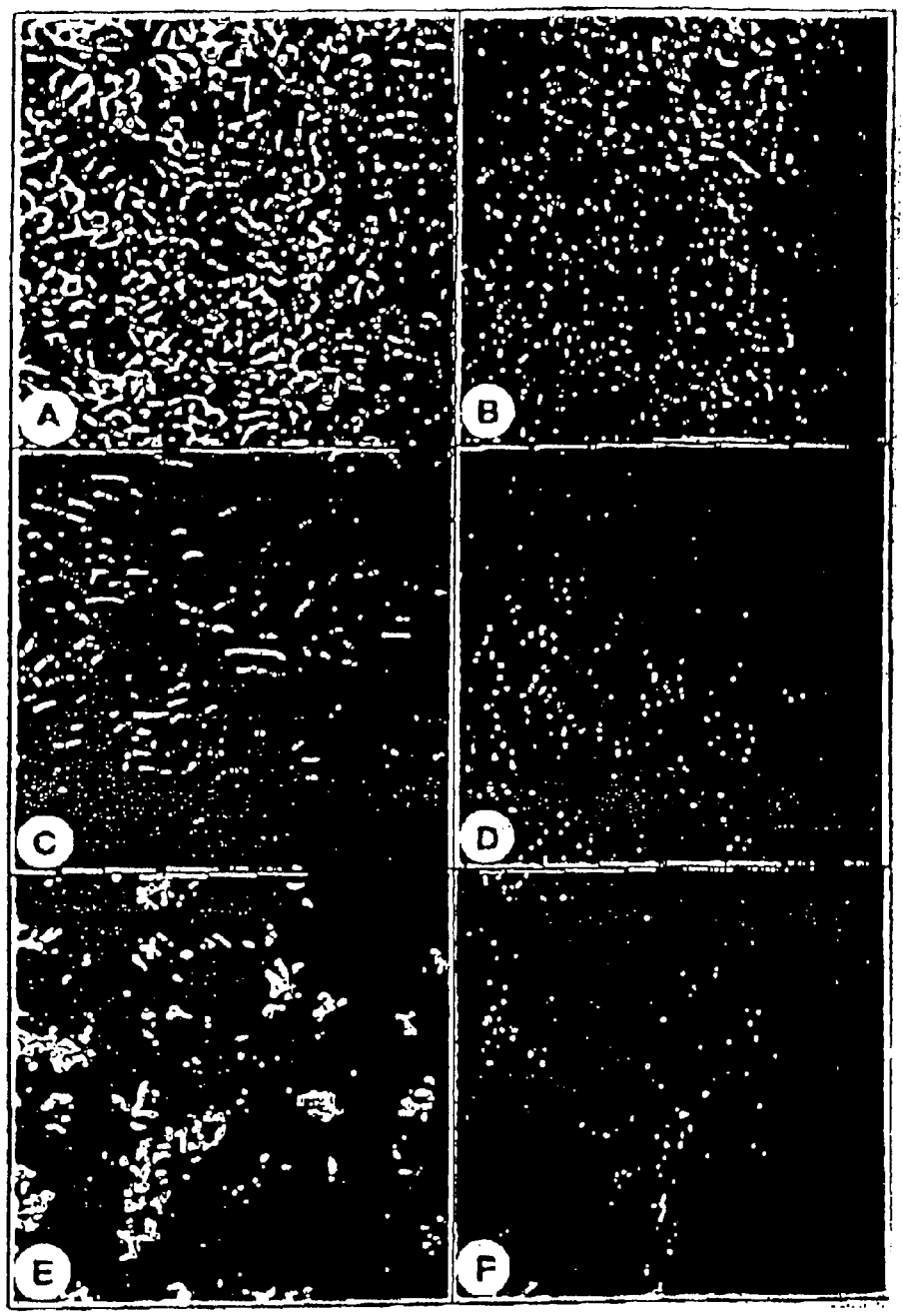
FIG. 19A–FIG. 19F. Comparative analyses of transduction efficiency of vCMVp-lacZ in HeLa cells (FIG. 19A) either following mock-treatment (FIG. 19B), or treatment with HU (FIG. 19C), genistein (FIG. 19D), tyrphostin 1 (FIG. 19E), or tyrphostin 23 (FIG. 19F). Approximately equivalent numbers of HeLa cells were either mock-treated or treated with the indicated compounds for 2 h and infected with 2 MOI of the vCMVp-lacZ vector under identical conditions. Forty eight h post infection, cells were fixed, stained with X-gal and photographed using a Nikon inverted light microscope. Magnification ×100.

Tyrphostin 1 and Tyrphostin 23 are More Effective and Less Toxic than HU and Genistein Treatment of cells with compounds such as genistein (Qing et al., 1998a; Qing et al., 1997b) or HU (Ferrari et al., 1996; Russell et al., 1995) has previously been shown to increase recombinant AAV transduction efficiency. To compare the effects of these compounds with that of tyrphostin, HeLa cells were either mock-treated or treated with 150 mM genistein, 10 mM HU, 500 mM tyrphostin 1, or 500 mM tyrphostin 23, followed by infection with vCMVp-lacZ at an MOI of 2 as described above. The results are shown in FIG. 19. It is evident that treatment with either tyrphostin 1 or tyrphostin 23 resulted in a much greater increase in recombinant AAV transduction efficiency than treatment with either genistein or HU.

Figure 20:
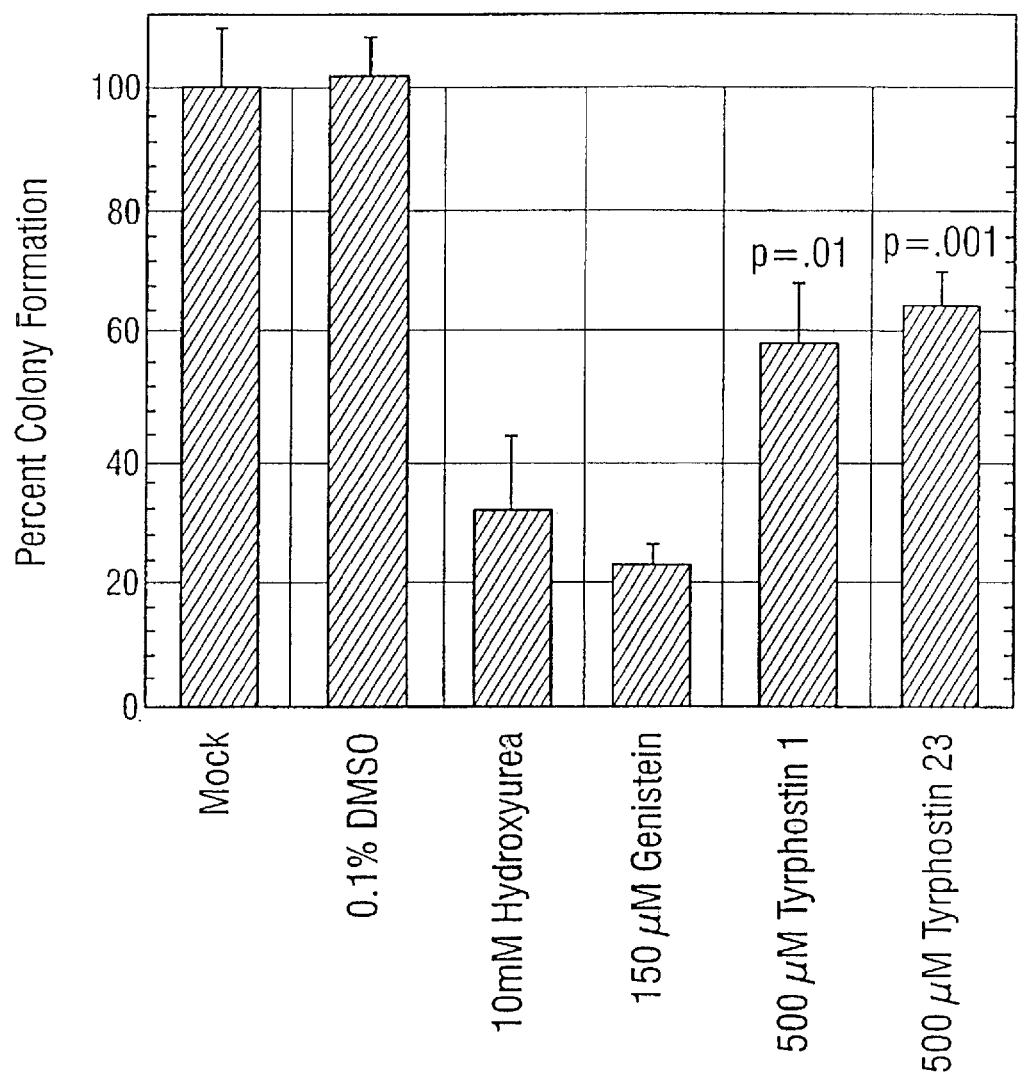
FIG. 20. Effect of DMSO, HU, genistein, and tyrphostin on cell-viability. Cytotoxicity assays with equivalent numbers of HeLa cells at optimal concentrations of each compound were performed under identical conditions as described in Example 1. The p values for tyrphostin treatments compared with treatments with HU and genistein are indicated.

In order to compare the relative toxicity of tyrphostin with that of HU or genistein, HeLa cells were treated with 500 mM tyrphostin 1 or tyrphostin 23, 150 mM genistein, or an equivalent volume of DMSO, for 2 h or 10 mM HU for 16 h, respectively. Following treatments, the numbers of viable cell colonies were enumerated as described in Example 1. The results are shown in FIG. 20. It is evident that with reference to the mock-treated or DMSO-treated controls, both tyrphostin 1 and tyrphostin 23 are far less toxic than either genistein or HU. Tyrphostin 23, in particular, is the least toxic of the four treatments for HeLa cells. Thus, the tyrphostin-treatment of primary cells may offer a physiological means to augment AAV transduction efficiency without causing a deleterious effect.

EXAMPLE 11

Tyrphostin-treatment Affects the Phosphorylation State of the ssD-BP

The data above demonstrate that recombinant AAV transduction efficiency correlates well with the phosphorylation state of the cellular ssD-BP (see also Qing et al., 1998a). For example, HeLa cells, which are not readily transduced by recombinant AAV vectors, contain predominantly the phosphorylated form of the ssD-BP. In 293 cells, on the other hand, the ssD-BP is present predominantly in the dephosphorylated form, and these cells can be efficiently transduced by recombinant AAV vectors. The inventors, therefore, next examined the effects of tyrphostin 1 and tyrphostin 23 on the phosphorylation state of the ssD-BP in HeLa cells, Tyrphostin 51, which had little effect on AAV transduction (FIG. 18), was included as an appropriate control. Similarly, the effect of EGF on the phosphorylation state of the ssD-BP in 293 cells was also examined.

Figure 21:
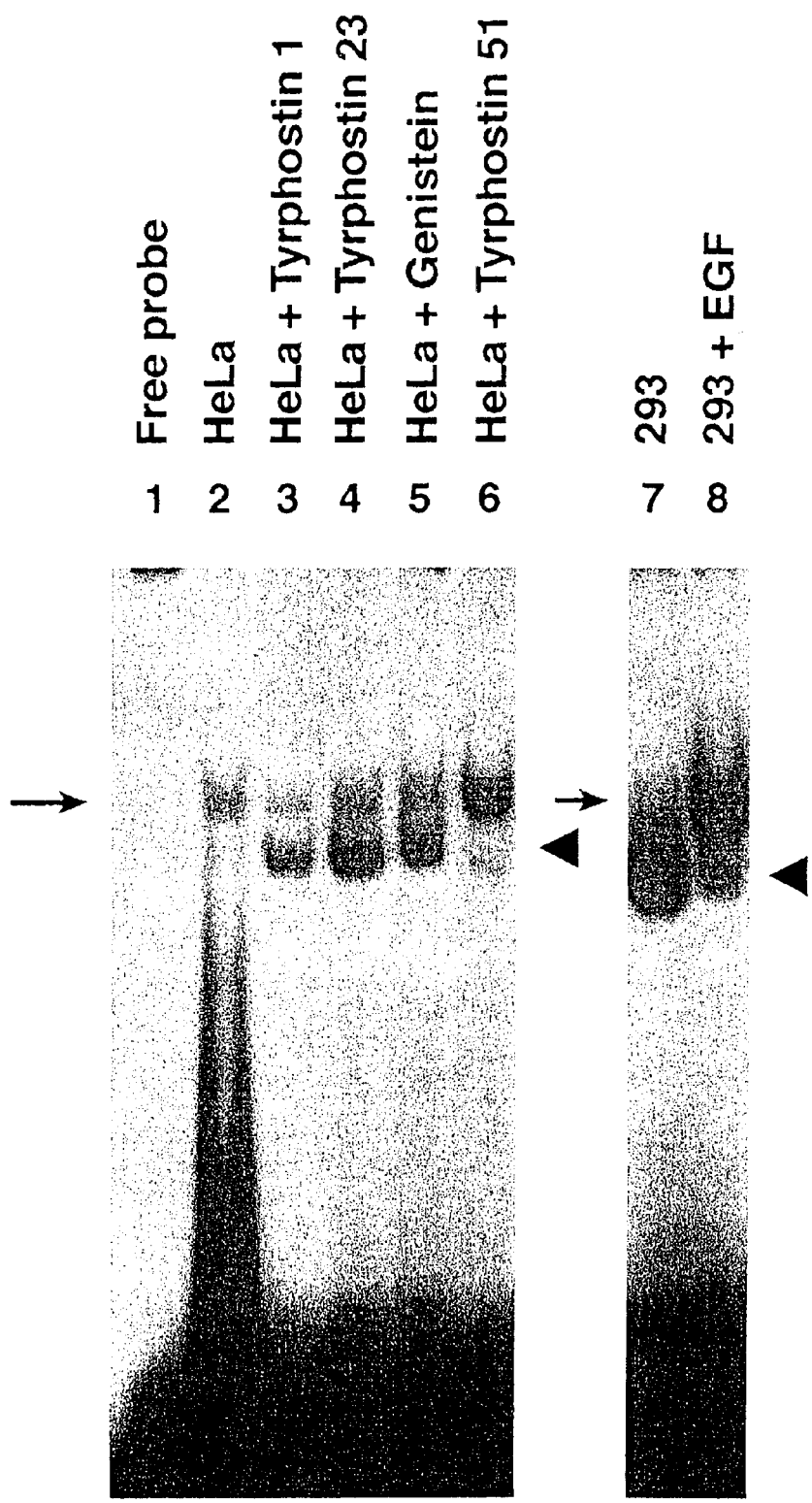
FIG. 21. EMSA with WCE prepared from human HeLa, and 293 cells. Equivalent amounts of WCE prepared from each indicated cell type were used in EMSA with the D(−) probe as described in the text. The phosphorylated and dephosphorylated forms of the ssD-BP are indicated by the arrow and the arrowhead, respectively.

In the first set of studies, HeLa cells were treated separately with tyrphostin 1, tyrphostin 23, or tyrphostin 51 (500 mM each) and genistein (150 mM) for 2 h, followed by preparation of WCEs. WCEs were then analyzed by EMSA utilizing the D(−) probe. FIG. 21 demonstrates that with the exception of tyrphostin 51, all treatments caused a significant increase in the amount of dephosphorylated form of the ssD-BP in HeLa cells. For example, the ratio (r) of dephosphorylated:phosphorylated forms of the ssD-BP in HeLa cells following each treatment, determined by densitometric analyses of autoradiographs, was as follows: mock, 0.4±0.2; tyrphostin 1,2.1±0.7; tyrphostin 23, 1.7±0.5; genistein, 1.5±0.5; and tyrphostin 51, 0.7±0.2. Thus, consistent with the above data the amount of dephosphorylated ssD-BP for each treatment corresponded with the level of increase in transduction efficiency for each of the compounds (Qing et al., 1998a).

In the second set of studies, 293 cells were either mock-treated or treated with 100 ng/ml EGF in IMDM for 1 h at 37° C. immediately followed by preparation of WCEs. WCEs were then analyzed by EMSA utilizing the D(−) probe. The ssD-BP in 293 cells was present mostly in the dephosphorylated form in mock-treated 293 cells as observed previously (Qing et al., 1998a), and the EGF-treatment resulted in a significant increase in the phosphorylation of the ssD-BP. Taken together, these results provide strong evidence that the EGF-R PTK plays a direct role in catalyzing the phosphorylation of the ssD-BP.

EXAMPLE 12

Recombinant AAV Transduction Efficiency Correlates Inversely with the EGF-R Expression The inventors reasoned that if EGF-R PTK is responsible for phosphorylating the ssD-BP, the efficiency of AAV-mediated transgene expression would be expected to be significantly lower in cells which express higher numbers of the EGF-R (A431 cells) than those which express fewer numbers of the EGF-R (H69 cells). Thus, AAV transduction efficiency would inversely correlate with the extent of the EGF-R expression. That is, the lower the level of EGF-R expression, the higher the transduction efficiency. This hypothesis was tested by using A431 and H69 cells, known to express very high and low numbers of the EGF-R, respectively. In addition, HeLa and 293 cells were infected with the vCMVp-lacZ vector at an MOI of 4 under identical conditions. Forty-eight h p.i., the cells were stained with X-gal.

It was determined that, consistent with the above data, the transduction efficiency in HeLa and 293 cells was approximately 4% and 20%, respectively, and less than 1% in A431 cells, as expected (Qing et al., 1998a). However, contrary to the expectation, little transduction (<1%) in H69 was observed. This apparent paradox was addressed by carrying out radiolabeled EGF and AAV binding assays. These data are shown in FIG. 22. It is clear that A431 cells bound the highest amounts of EGF (Fabricant et al., 1977; Giard et al., 1973), followed by HeLa and 293 cells (FIG. 22A). EGF binding to H69 cells was negligibly small (Gamou et al, 1987). The possibility that H69 cells do not express the receptor for AAV, was substantiated by AAV binding assays, the results of which are shown in FIG. 22B. H69 cells fail to bind AAV, an observation consistent with that in M07e cells, an AAV receptor-negative cell line (Ponnazhagan et al., 1996). A431 cells, on the other hand, express far greater numbers of the AAV receptor than HeLa or 293 cells. Thus, the low-level of AAV-mediated transduction in A431 cells cannot be attributed to a lack of expression of AAV receptors in these cells.

EXAMPLE 13

Phosphorylation State of the ssD-BP in A431 and H69 Cells is Insensitive to EGF-treatment Since the EGF-R PTK appeared to catalyze phosphorylation of the ssD-BP, the inventors next examined the effects of EGF as well as tyrphostin- and genistein-treatments on A431 and H69 cells. The rationale for these studies was that EGF-treatment would have no effect on the phosphorylation state of the ssD-BP in either cell type because high-levels of expression of the EGF-R in A431 cells would ensure that the ssD-BP would be present in its phosphorylated form, and H69 cells would fail to respond to EGF since little expression of the EGF-R occurs in these cells. Equivalent numbers of cells were either mock-treated or treated with 100 ng/ml EGF for 1 h at 37° C. immediately followed by preparation of WCEs, and analyzed by EMSA utilizing the D(−) probe. As shown in FIG. 23, EGF-treatment had no significant effect on the phosphorylation state of the ssD-BP in both cell types. In A431 cells, the ssD-BP was present predominantly in phosphorylated form due to high-levels of expression of the EGF-R PTK. In H69 cells, on the other hand, both phosphorylated and dephosphorylated forms of the ssD-BP were detected. Interestingly, however, treatment with tyrphostin or genistein, led to conversion to dephosphorylated form of the ssD-BP resulting in increased transduction in A431 cells. Under identical condition, however, these treatments had no effect on the phosphorylation state of the ssD-BP in H69 cells, and these cells could not be transduced by AAV since they lack the cell surface receptor for AAV. Although it is not readily apparent which of the cellular protein kinases phosphorylate the ssD-BP in H69 cells, these results are consistent with the conclusion that phosphorylation of the ssD-BP in A431 cells is catalyzed by the EGF-R PTK.

EXAMPLE 14

Stable Transfection of EGF-R cDNA Into 293 Cells Causes Phosphorylation of the ssD-BP and Results in Inhibition of AAV-mediated Transgene Expression 293 cells can be efficiently transduced by recombinant AAV vectors since they contain predominantly dephosphorylated form of the ssD-BP (see examples above and Qing et al., 1998a). The inventors examined whether deliberate over-expression of the EGF-R PTK in 293 cells would cause phosphorylation of this protein, and consequently, lead to inhibition of AAV-mediated transgene expression in these cells. 293 cells were transfected with the EGF-R expression plasmid DNA, and a number of stably-transfected clones were isolated as described in Example 1.

WCEs prepared from individual 293 cell clones were used in EMSAs to determine the ratios of dephosphorylated/phosphorylated ssD-BPs and compared with that in control, untransfected 293 cells. Replicate cultures were also evaluated for the efficiency of the recombinant vCMVp-lacZ vector-mediated transduction, with or without prior treatment with tyrphostin 1, under identical conditions. These results are shown in Table 6. It is interesting to note that in each of the transfected 293 cell clones, the ratio of dephosphorylated/phosphorylated ssD-BPs was reduced to an average of 0.45 from more than 3.5 in the control 293 cells, which also led to a significant decrease in AAV transduction efficiency from approximately 18% in control 293 cells to an average of about 2% in EGF-R-transfected 293 cell clones. Treatment with tyrphostin 1, on the other hand, resulted in an increase in AAV transduction efficiency to an average of approximately 22.5% in EGF-R-transfected 293 cell clones. These data provide strong evidence that the EGF-R-ssD-BP interaction plays a crucial role in AAV-mediated transgene expression.

TABLE 6

Effect of stable transfection of the EGF-R cDNA on the phosphorylation state of the ssD-BP and AAV-mediated transgene expression in 293 cells.

| Cells/ clones[a] | Ratio of dephosphorylated/ phosphorylated ssD-BP[b] | Efficiency of AAV-mediated transgene expression[c] | |
|---|---|---|---|
| | | −Tyrphostin 1 | +Tyrphostin 1 |
| 1. 293 | 3.5 ± 1.8 | 18.1 ± 2.4 | 33.8 ± 6.8 |
| 2. 293-4 | 0.31 | 1.3 ± 0.2 | 17.7 ± 2.9 |
| 3. 293-5 | 0.45 | 2.1 ± 1.1 | 12.6 ± 0.9 |
| 4. 293-6 | 0.36 | 2.1 ± 0.3 | 19.7 ± 5.1 |
| 5. 293-8 | 0.51 | 2.2 ± 0.7 | 24.6 ± 6.5 |
| 6. 293-12 | 0.64 | 2.5 ± 1.0 | 37.8 ± 4.4 |

[a]293 cells were either used directly (#1), or transfected with plasmid pCH-CEGFR and individual clones (#2–6) were obtained following selection with 300 mg/ml of hygromycin for 14 days.
[b]Autoradiographic images of EMSA gels were scanned densitometrically and the ratios of dephosphorylated/phosphorylated ssD-BPs were determined as previously described (40). $p < 0.005$.
[c]Equivalent numbers of mock-transfected 293 cells or 293 cell clones transfected with pCHCEGFR plasmid were infected with vCMVp-lacZ vector at an MOI of 2, and percentage of cells expressing the transgene, with and without prior treatment with 500 mM tyrphostin 1, were determined 48 h p.i. as described in Example 1.

EXAMPLE 15

Phosphorylation of the ssD-BP is Mediated by the EGF-R PTK

Figure 24:
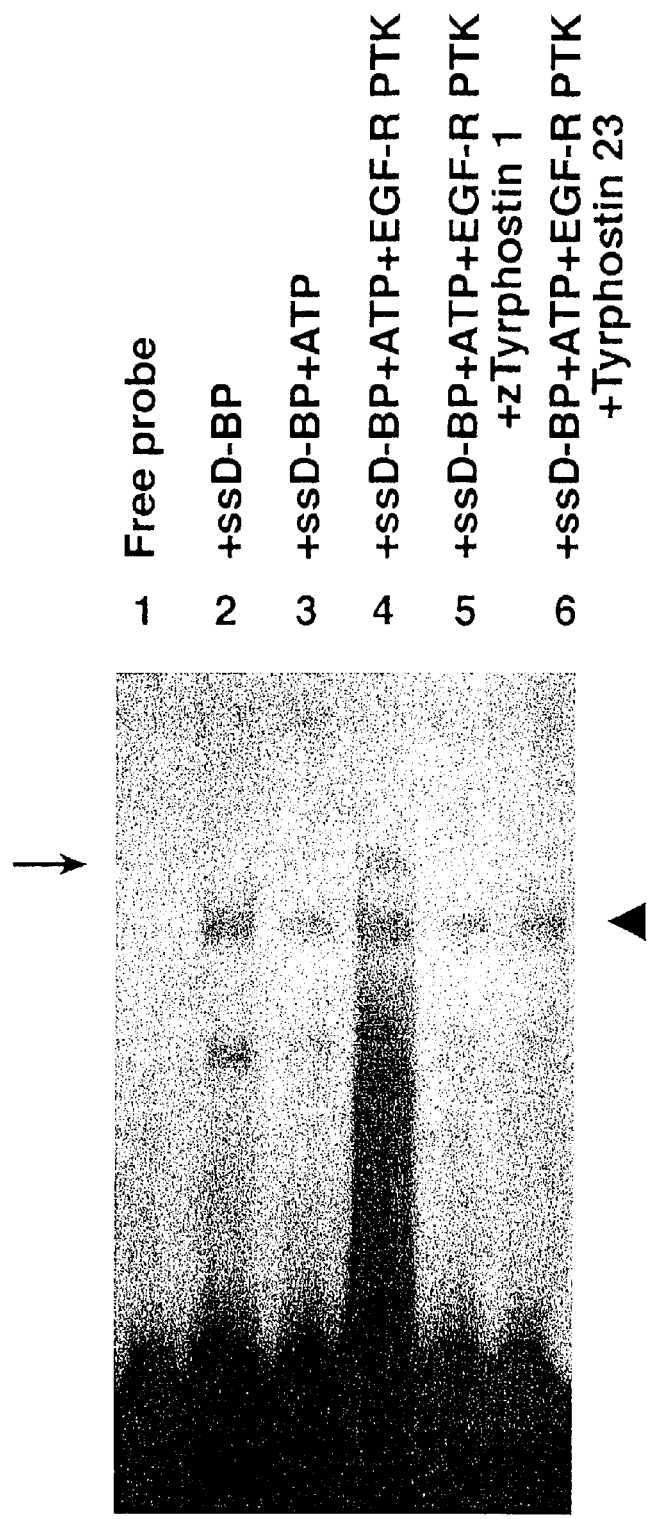
FIG. 24. In vitro phosphorylation of the ssD-BP by the EGF-R PTK. Equivalent amounts of the ssD-sequence affinity column-purified ssD-BP from 293 cells were incubated either in the absence (lane 2), or in the presence of ATP (lane 3), or in the presence of ATP+EGF-R PTK (lane 4), or in the presence of ATP+EGF-R PTK+tyrphostin 1 (lane 5), or in the presence of ATP+EGF-R PTK+tyrphostin 23 (lane 6), followed by EMSA with the D(−) probe as described in Example 1. The phosphorylated and dephosphorylated forms of the ssD-BP are indicated by the arrow and the arrowhead, respectively.

In order to unequivocally establish that tyrosine phosphorylation of the ssD-BP is indeed carried out by the EGFR-PTK, in vitro phosphorylation assays were performed with the commercially available purified EGF-R PTK using a ssD-sequence affinity column-purified dephosphorylated form of the ssD-BP from 293 cells followed by EMSA as described in Example 1. The results of these studies are shown in FIG. 24. As is evident, incubation of the ssD-BP with the purified EGF-R PTK resulted in phosphorylation of this protein whereas incubation in the presence of ATP alone had no effect. More interestingly, in vitro phosphorylation of the ssD-BP by the EGF-R PTK was abrogated in the presence of tyrphostin 1 and tyrphostin 23. These results provide direct evidence that the ssD-BP is a downstream target of the EGF-R PTK.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

Akiyama et al., *J. Biol. Chem.*, 262:5592–5595, 1987.
Alexander et al., *Hum. Gene Ther.*, 7:841–850, 1996.
Arap et al., *Cancer Res.*, 55:1351–1354, 1995.
Baichwal and Sugden, In: *Gene Transfer*, Kucherlapati R, ed., New York, Plenum Press, pp. 117–148, 1986.
Barany and Merrifield, In: *The Peptides*, Gross and Meienhofer, eds., Academic Press, New York, pp. 1–284, 1979.
Barnes and Peterson, *Soc. Exp. Biol. Med.*, 280:103–109, 1995.
Bedzyk et al., *J. Biol. Chem.*, 265:18615, 1990.
Benvenisty and Neshif, *Proc. Nat. Acad. Sci. USA*, 83:9551–9555, 1986.
Berns and Bohenzky, *Adv. Virus Res.*, 32:243–307, 1987.
Berns and Giraud, *Curr. Top. Microbiol. Immunol.*, 218:1–23, 1996.
Bertran et al., *J Virol.*, 70 (10) 6759–6766, 1996.
Boonstra et al., *Cell Biol. Intl.*, 19:413–430, 1995
Burgess and Kelly, *Annu Rev Cell Biol* 3:243–293, 1987.
Bussemakers et al., *Cancer Res.*, 52:2916–2922, 1992.
Caldas et al., *Nat. Genet.*, 8:27–32, 1994.
Campbell et al., *J. Mol. Biol.*, 180:1–19, 1984.
Capaldi et al., *Biochem. Biophys. Res. Comm.*, 76:425, 1977
Carlo-Stella et al., *Br. J. Haematol.*, 93:551–557, 1996
Carter and Flotte, *Curr. Top. Microbiol. Immunol.*, 218:119–144, 1996.
Carter, *Curr. Opin. Biotechnol.*, 3:533–539, 1992.
Casey et al, *Oncogene*, 6:1791–1797, 1991.
Chang, et al., *J. Virol.*, 70:4150–4156, 1996.
Chatterjee and Wong Jr., *Curr. Top. Microbiol. Immunol.*, 218:61–73, 1996.
Chatterjee, et al., *Ann. N.Y. Acad Sci.*, 770:79–90, 1995.
Chaudhary et al., *Proc. Natl. Acad. Sci.*, 87:9491, 1990.
Chavez et al., In: *Methods in Cell Biology*, Roth, M., Ed. New York, Academic Press, 43:263–288, 1994.
Chen and Okayama, *Mol. Cell Biol.*, 7:2745–2752, 1987.
Cheng et al., *Cancer Res.*, 54:5547–5551, 1994.
Cheung et al., *Biochem. J.*, 295:427–435, 1993c.
Cheung et al., *J. Biol. Chem.*, 268:24303–24310, 1993a.
Cheung et al., *J. Biol. Chem.*, 268:6139–6146, 1993b.
Chodosh, In: *Current Protocols in Molecular Biology*, Ausubel, F. M., Brent, R., Kingston, R. E., Moore, D. D., Seidman, J. G., Smith, J. A. and Struhl, K., eds., (John Wiley and Sons, Inc., Boston, Mass.), Vol. 2, pp. 12.5.1–12.5.8, 1995.
Christensen, et al., *J. Virol.*, 71:1405–1416, 1997.
Coffin, In: *Virology*, Fields B N, Knipe D M, ed., New York: Raven Press, pp. 1437–1500, 1990.
Constantinou, and Huberman, *Soc. Exp. Biol. Med.*, 203:109–115, 1995.
Couldwell et al., *FEBS Lett.*, 345:43–46, 1994.
Dobner et al., *Science*, 272:1470–1473, 1996.

Dubensky et al., *Proc. Nat. Acad Sci. USA*, 81:7529–7533, 1984.
Dudek, et al., *Science*, 275:661–664, 1996.
Dvir et al., *J. Cell Biol.*, 113:857–865, 1991.
Edelman and Crossin, *Annu. Rev. Biochem.*, 60:155–190, 1991
Edelman, *Annu. Rev. Biochem.*, 54:135–169, 1985.
Faaland et al., *Mol. Cell. Biol.*, 11:2697–2703, 1991.
Faaland et al., *Mol. Cell Biol.*, 11(5):2697–2703, 1991.
Fabricant et al., *Proc. Natl. Acad. Sci. USA*, 74:565–569, 1977.
Fechheimer et al., *Proc. Natl. Acad. Sci. USA*, 84:8463–8467, 1987.
Ferber et al., *Mol Endocrinol.* 5(3):319–26, 1991.
Ferkol et al., *FASEB J.*, 7:1081–1091, 1993.
Ferrari et al., *J. Virol.*, 70:3227–3234, 1996.
Fisher et al., *Nat. Med.*, 3:306–312, 1997
Fisher et al, *J. Virol.*, 70:520–532, 1996.
Flotte and Carter, *Gene Ther.*, 2:357–362, 1995.
Flotte et al., *Proc. Natl. Acad Sci. USA*, 90:10613–10617, 1993.
Fraley et al., *Proc. Natl. Acad. Sci. USA*, 76:3348–3352, 1979.
Freshner, *In: Animal Cell Culture: a Practical Approach*, Second Edition, Oxford/New York, IRL Press, Oxford University Press, 1992.
Freshner, *In: Animal Cell Culture: a Practical Approach*, Second Edition, Oxford/New York, IRL Press, Oxford University Press, 1992.
Frix et al., *J. Cell Biol.*, 113:173–185, 1991.
Fukazawa et al., *Biochem. Pharmacol.*, 42:1661–1671, 1991.
Gamou et al., *Cancer Res.*, 47:2668–2673, 1987.
Gazit et al., *J. Med Chem.*, 32:2344–2352, 1989.
Gefter et al., *Somatic Cell Genet.*, 3:231–236, 1977.
Ghiringhelli and Romanowski, *Biotechniques*, 17:464–465, 1994.
Ghosh and Bachhawat, *In: Liver diseases, targeted diagnosis and therapy using specific receptors and ligands*, Wu G, Wu C ed., New York: Marcel Dekker, pp. 87–104, 1991.
Giancotti and Ruoslahti, *Cell*, 60:849–859, 1990.
Giard et al., *J. Natl. Cancer Inst.*, 51:1417–1423, 1973.
Goding, *In: Monoclonal Antibodies: Principles and Practice*, 2d ed., Academic Press, Orlando, Fla., pp. 60–61, and 71–74, 1986.
Goodman et al., *Blood*, 84:1492–1500, 1994.
Gopal, *Mol. Cell Biol.*, 5:1188–1190, 1985.
Graham and Van Der Eb, *Virology*, 52:456–467, 1973.
Harland and Weintraub, *J. Cell Biol.*, 101:1094–1099, 1985.
Harlow and Lane, *In: Antibodies: A Laboratory Manual*, Cold Spring Harbor Laboratory, Cold Spring Harbor, N.Y., 1988
Hirt, *J. Mol. Biol.*, 26:365–369, 1967.
Hollestein et al., *Science*, 253:49–53 1991.
Hussussian et al., *Nature Genetics*, 15–21, 1994.
Johnson et al., *In: Biotechnology And Pharmacy*, Pezzuto et al., eds., Chapman and Hall, New York, 1993.
Kamb et al., *Nature Genetics*, 8:22–26, 1994.
Kamb et al., *Science*, 2674:436–440, 1994.
Kaneda et al., *Science*, 243:375–378, 1989.
Kaplitt, et al., *Nat. Genet.*, 8:148–153, 1994.
Kaplitt, et al., *Arm. Thor. Surg.*, 62:1669–1676, 1996.
Kato et al., *J. Biol Chem.*, 266:3361–3364, 1991.
Kaur, *Anti-Cancer Drugs* 5:213–222, 1994.
Kearns et al, *Gene Ther.*, 3:748–755, 1996.
Kessler et al., *Proc. Natl. Acad Sci. USA*, 93:14082–14087, 1996.
Klein et al., *Nature*, 327:70–73, 1987.
Koeberl et al., *Proc. Natl. Acad. Sci. USA*, 94:1426–1431, 1997.
Kohler and Milstein, *Eur. J. Immunol.*, 6:511–519, 1976.
Kohler and Milstein, *Nature*, 256:495–497, 1975.
Kotin et al, *Genomics*, 10:831–834, 1991.
Kotin et al., *Proc. Natl. Acad Sci. USA*, 87:2211–2215, 1990.
Kovalenko et al., *Cancer Res.* 54:6106–6114, 1994.
Kube and Srivastava, *Nucl. Acids Res.*, 25:3375–3376, 1997.
Kube et al., *J. Virol.*, 71:7361–7371, 1997.
Kumagai and Dunphy, *Science*, 273:1377–1380, 1996.
Kuo and Yang, *Biochem. Biophys. Res. Comm.*, 212:767–75, 1995.
Kusov et al., *J. Virol.* 70:1890–1897, 1996.
Kyte and Doolittle, *J. Mol. Biol.*, 157(1): 105–132, 1982.
Levitzki et al., *Meth. Enzymol.*, 201:347–361. 1991.
Levitzki, *Biochem. Pharmacol.*, 40:913–918, 1990.
Lim and Hauschka, *J. Cell. Biol.*, 98:739–747, 1984.
Lin and Guidotti, *J. Biol. Chem.*, 264:14408–14414, 1989.
Livneh et al., *J. Biol. Chem.*, 261:12490–12497, 1986.
Lyall et al., *J. Biol. Chem.*, 264:14503–14509, 1989.
Macejak and Sarnow, *Nature*, 353:90–94, 1991.
Mains et al., *Mol. Endocrinol.*, 9:(1)3–13, 1995.
Mannetal., *Cell*, 33:153–159, 1983.
Markovits et al., *Biochem. Pharm.*, 48(3):549–560, 1994
Matsura et al., *Brit. J. Cancer*, 66:1122–1130, 1992.
McCown et al., *Brain Res.*, 713:99–107, 1996.
McGlynn et al., *Eur. J. Biochem.*, 207:265–275, 1992.
Mercer, *Critic. Rev. Eukar. Gene Express.*, 2:251–263, 1992.
Merrifield, *Science*, 232:341–347, 1986.
Miller et al., *Cell Growth Diff.*, 5:1263–1274, 1994.
Mizukami et al., *Virology*, 217:124–130, 1996.
Montenarh, *Crit. Rev. Oncogen*, 3:233–256, 1992.
Mori et al., *Cancer Res.*, 54:3396–3397, 1994.
Muller, *J. Virol.*, 61:858–865, 1987.
Muzyczka, *Curr. Top. Microbiol. Immunol.*, 158:97–129, 1992.
Myers, EPO 0273085.
Nahreini et al., *Gene*, 124:257–262, 1993.
Nicolas and Rubenstein, *In: Vectors: A survey of molecular cloning vectors and their uses*, Rodriguez and Denhardt (eds.), Stoneham: Butterworth, pp. 493–513, 1988.
Nicolau and Sene, *Biochim. Biophys. Acta*, 721:185–190, 1982.
Nicolau et al, *Methods Enzymol.*, 149:157–176, 1987.
Nobri et al, *Nature (London)*, 368:753–756, 1995.
Novogrodsky et al., *Science*, 264:1319–1322, 1994.
Obrink, *BioEssays.*, 13:227–233, 1991.
Odin and Obrink, *Exp. Cell Res.*, 171:1–15, 1987.
Ohmichi et al., *Biochemistry*, 32:4650–4658, 1993.
Okada et al., *J. Biol. Chem.*, 269:3563–3567, 1994
Okamoto et al., *Proc. Natl. Acad. Sci. USA*, 91:11045–11049, 1994.
Orlow et al, *Cancer Res.*, 54:2848–2851, 1994.
Pelletier and Sonenberg, *Nature*, 334:320–325, 1988.
Perales et al., *Proc. Natl. Acad. Sci.* 91:4086–4090, 1994.
Perri and Ganem, *J. Virol.*, 70:6803–6809, 1996.
Ping et al, *Microcirculation*, 3:225–228, 1996.
Piwnica-Worms, Saunders, Roberts, Smith, Cheng, *Cell*, 49:75–82, 1987.
Ponnazhagan et al., *Gene*, 190:203–210, 1997c.
Ponnazhagan et al., *J. Virol.*, 71:8262–8267, 1997d.
Ponnazhagan et al., *Hum. Gene Ther.*, 8:275–284. 1997a.
Ponnazhagan et al., *J. Virol.*, 71:3098–3104, 1997b.
Ponnazhagan et al., *J. Gen. Virol.*, 77:1111–1122, 1996.
Potter et al., *Proc. Nat. Acad. Sci. USA*, 81:7161–7165, 1984.

Qing et al., *J. Virol.*, 72:1593–1599, 1998.
Qing et al., *J. Virol.*, 71:5663–5667, 1997a.
Qing et al, *Proc. Natl. Acad. Sci. USA*, 94:10879–10884, 1997b.
Ridgeway, In: *Vectors: A survey of molecular cloning vectors and their uses*, Rodriguez R L, Denhardt D T, ed., Stoneham: Butterworth, pp.467–492, 1988.
Rippe et al, *Mol. Cell Biol.*, 10:689–695, 1990.
Rosenberg, *Duodecim.*, 106:(14) 1027–1029, 1990.
Russell et al, *Proc. Natl. Acad. Sci. USA*, 91:8915–8919, 1994.
Russell et al, *Proc. Natl. Acad. Sci. USA*, 92:5719–5723, 1995.
Sambrook et al., In: *Molecular Cloning: A Laboratory Manual*, Cold Spring Harbor Laboratory Press, Cold Spring Harbor, N.Y., 1989.
Samulski et al., *J. Virol.*, 36:3822–3828, 1989.
Samulski et al., *EMBO J.*, 10:3941–3950, 1991.
Samulski et al., *J. Virol.* 61(10):3096–3101, 1987.
Serrano et al., *Nature*, 366:704–707, 1993.
Serrano et al., *Science*, 267:249–252, 1995.
Southern, *J. Mol. Biol.*, 98:503–517, 1975.
Srivastava et al., *Curr. Top. Microbiol. Immunol.*, 218:93–117, 1996.
Srivastava et al., Cancer *Genet Cytogenet.*, 35:(1)61–71, 1988.
Srivastava et al., *J. Virol.*, 45:555–564, 1983.
Stewart and Young, In: *Solid Phase Peptide Synthesis*, 2d. ed., Pierce Chemical Co., 1984.
Styren et al., *Brain Res.*, 615:181–190, 1993.
Takahashi et al., *Cancer Res.*, 52:2340–2342, 1992.
Tam et al., *J. Am. Chem. Soc.*, 105:6442, 1983.
Temin, In: *Gene Transfer*, Kucherlapati (ed.), New York: Plenum Press, pp. 149–188, 1986.
Tokiwa et al., *Science*, 273:792–794, 1996.
Tur-Kaspaet al., *Mol. Cell Biol.*, 6:716–718, 1986.
U.S. Pat. No. 4,554,101.
U.S. Pat. No. 4,933,294.
U.S. Pat. No. 4,943,533.
U.S. Pat. No. 5,183,884.
U.S. Pat. No. 5,359,046.
U.S. Pat. No. 5,378,809.
U.S. Pat. No. 5,480,968.
U.S. Pat. No. 5,487,979.
U.S. Pat. No. 5,554,519.
U.S. Pat. No. 5,558,864.
U.S. Pat. No. 5,587,459.
U.S. Pat. No. 5,610,018.
U.S. Pat. No. 5,610,288.
U.S. Pat. No. 5,614,488.
U.S. Pat. No. 5,654,307.
U.S. Pat. No. 5,674,753.
U.S. Pat. No. 5,679,683.
U.S. Pat. No. 5,708,156.
U.S. Pat. No. 5,717,067.
U.S. Pat. No. 5,763,198.
U.S. Pat. No. 5,773,476.
U.S. Pat. No. 5,789,427.
Umbas et al., *Cancer Res.*, 52:5104–5109, 1992.
Vlahos et al., *J. Biol. Chem.*, 269:5241–5248, 1994
Wagner et al., *Proc. Natl. Acad. Sci.* 87(9):3410–3414, 1990.
Walsh et al., *J. Clin. Invest.*, 94:1440–1448, 1994.
Wang et al., *J. Virol.*, 72:5472–5480, 1998.
Wang et al., *J. Virol.*, 71:3077–3082, 1997.
Wang et al., *J. Virol.*, 70:1668–1677, 1996.
Wang et al., *J. Mol. Biol.*, 250:573–580, 1995.
Weber et al., *J. Biol. Chem.*, 259:14631–14636, 1984.
Weinberg, *Science*, 254:1138–1146, 1991.
Williams and Chase, In: *The Biology of Non-specific DNA Protein Interactions*, Rezvin, A. ed., (CRC Press, Boca Raton, Fla.), pp. 197–227, 1990.
Wong et al., *Gene*, 10:87–94, 1980.
Wu and Wu, *Biochemistry*, 27:887–892, 1988.
Wu and Wu, *J. Biol. Chem.*, 262:4429–4432, 1987.
Wu and Wu, *Adv. Drug Delivery Rev.*, 12:159–167, 1993.
Xiao et al., *J. Virol.*, 70:8098–8108, 1996.
Yaish et al., *Science*, 242:933–935, 1988.
Yang et al., *Proc. Natl. Acad. Sci USA*, 87:9568–9572, 1990.
Zelenin et al., *FEBS Lett.*, 280:94–96, 1991.
Zhou et al., *Gene Ther.*, 3:223–229, 1996.

---

What is claimed is:

1. A method for increasing the transcription of a selected nucleic acid from an adeno-associated viral (AAV) vector in a host cell comprising the steps of:
   (i) providing an AAV vector comprising an expression cassette comprising said selected nucleic acid and a promoter active in eukaryotic cells, wherein said selected nucleic acid is operably linked to said promoter;
   (ii) contacting said vector with said host cell under conditions permitting uptake of said vector by said host cell; and
   (iii) inhibiting the function of D sequence binding protein (D-BP) in said host cell,
whereby the transcription of said selected nucleic acid is increased relative to the transcription of said selected nucleic acid in a cell where D-BP is not inhibited.

2. The method of claim 1, wherein said inhibiting comprises reducing the expression of D-BP in said host cell.

3. The method of claim 1, wherein said inhibiting comprises reducing the D sequence binding activity of said D-BP in said host cell.

4. The method of claim 1, wherein said host cell is in a mammal.

5. The method of claim 2, wherein the agent that reduces the expression of D-BP is an antibody or a small molecule inhibitor.

6. The method of claim 2, wherein said agent is AdE4orf6.

7. The method of claim 5, wherein the antibody is a single chain antibody.

8. The method of claim 5, wherein said antibody is a monoclonal antibody.

9. The method of claim 5, wherein reducing the binding activity of D-BP is achieved by contacting said cell with an oligonucleotide that mimics AAV D-sequences.

10. The method of claim 3, wherein reducing the binding activity is achieved by inhibiting the tyrosine phosphorylation of D-BP.

11. The method of claim 10, wherein inhibiting the phosphorylation is achieved by contacting said host cell with a D-BP peptide containing a tyrosine residue.

12. The method of claim 10, wherein inhibiting the phosphorylation is achieved by contacting said host cell with an agent that inhibits tyrosine kinase.

13. The method of claim 10, wherein inhibiting the phosphorylation is achieved by contacting said host cell with a nucleic acid encoding a phosphatase.

14. The method of claim 12, wherein said tyrosine kinase is an EGF-R tyrosine kinase.

15. The method of claim 12, wherein said agent is selected from the group consisting of hydroxyurea, genistein, tyrphostin 1, tyrphostin 23, tyrphostin 63, tyrphostin 25, tyrphostin 46, and tyrphostin 47.

16. The method of claim 14, wherein said agent is an inhibitor of EGF-R that reduces the expression of EGF-R protein kinase.

17. The method of claim 14, wherein the inhibitor of EGF-R protein kinase is an agent that binds to and inactivates EGF-R protein kinase.

18. The method of claim 14, wherein the inhibitor of EGF-R protein kinase inhibits the interaction of EGF-R with a D-BP.

19. The method of claim 16, wherein the agent that reduces the expression of EGF-R protein kinase is an antisense construct.

20. The method of claim 17, wherein the agent that binds to and inactivates EGF-R protein kinase is an antibody or a small molecule inhibitor.

21. The method of claim 20, wherein the antibody is a single chain antibody.

22. The method of claim 20, wherein said antibody is a monoclonal antibody.

23. The method of claim 4, wherein said mammal is a human.

24. The method of claim 23, wherein said host cell is a tumor cell.

25. A method for promoting the replication of an adeno-associated viral (AAV) vector in a host cell comprising the steps of:

(i) providing an AAV vector;

(ii) contacting said vector with said host cell under conditions permitting uptake of said vector by said host cell; and (iii) inhibiting the function of D sequence binding protein (D-BP) in said host cell, whereby the replication of said vector is promoted relative to the replication of said vector in a cell where D-BP is not inhibited.

26. The method of claim 25, wherein said AAV vector comprises an expression cassette comprising a selected nucleic acid and a promoter active in eukaryotic cells, wherein said selected nucleic acid is operably linked to said promoter.

27. The method of claim 25, further comprising inhibiting EGF-R protein kinase activity, expression or function.

28. A method for increasing the expression of a selected nucleic acid from an adeno-associated viral (AAV) vector in a host cell comprising the steps of:

(i) providing an AAV vector;

(ii) contacting said vector with said host cell under conditions permitting uptake of said vector by said host cell; and (iii) inhibiting the function of D sequence binding protein (D-BP) in said host cell, whereby the expression of said selected nucleic acid is increased relative to the expression of said selected nucleic acid in a cell where D-BP is not inhibited.

29. The method of claim 28, wherein said AAV vector comprises an expression cassette comprising said selected nucleic acid and a promoter active in eukaryotic cells, wherein said selected nucleic acid is operably linked to said promoter.

30. The method of claim 28, further comprising inhibiting EGF-R protein kinase activity, expression or function.

31. A method for treating a disease in a subject comprising the steps of:

(i) providing an adeno-associated virus (AAV) vector comprising an expression cassette comprising a therapeutic nucleic acid and a promoter active in eukaryotic cells, wherein said therapeutic nucleic acid is operably linked to said promoter;

(ii) contacting said vector with said host cell under conditions permitting uptake of said vector by said host cell; and (iii) inhibiting the function of D sequence binding protein (D-BP) in said host cell, whereby the therapeutic nucleic acid is transcribed in said cell and effects a treatment of said disease.

32. The method of claim 31, wherein said disease is cancer.

33. The method of claim 31, further comprising inhibiting EGF-R protein kinase activity, expression or function.

34. The method of claim 31, wherein said therapeutic nucleic acid encodes a polypeptide.

35. The method of claim 31, wherein said therapeutic nucleic acid encodes an antisense mRNA.

* * * * *